US012668601B2

(12) United States Patent
Stoessel

(10) Patent No.: US 12,668,601 B2
(45) Date of Patent: Jun. 30, 2026

(54) POLYCYCLIC COMPOUNDS FOR ORGANIC ELECTROLUMINESCENT DEVICES

(71) Applicant: UDC IRELAND LIMITED, Dublin (IE)

(72) Inventor: Philipp Stoessel, Darmstadt (DE)

(73) Assignee: UDC IRELAND LIMITED, Dublin (IE)

(*) Notice: Subject to any disclaimer, the term of this patent is extended or adjusted under 35 U.S.C. 154(b) by 938 days.

(21) Appl. No.: 17/917,005

(22) PCT Filed: Apr. 1, 2021

(86) PCT No.: PCT/EP2021/058563

§ 371 (c)(1),
(2) Date: Oct. 5, 2022

(87) PCT Pub. No.: WO2021/204646

PCT Pub. Date: Oct. 14, 2021

(65) Prior Publication Data

US 2023/0183269 A1 Jun. 15, 2023

(30) Foreign Application Priority Data

Apr. 6, 2020 (EP) .................................... 20168237

(51) Int. Cl.

| | |
|---|---|
| ***H10K 85/30*** | (2023.01) |
| ***C07D 471/22*** | (2006.01) |
| ***C07F 5/02*** | (2006.01) |
| ***H10K 85/60*** | (2023.01) |

(52) U.S. Cl.

CPC ............ *C07F 5/027* (2013.01); *C07D 471/22* (2013.01); *H10K 85/322* (2023.02); *H10K 85/6572* (2023.02)

(58) Field of Classification Search

None

See application file for complete search history.

(56) References Cited

U.S. PATENT DOCUMENTS

| | | | | |
|---|---|---|---|---|
| 2011/0278556 | A1 | 11/2011 | Kottas et al. | |
| 2014/0091265 | A1 | 4/2014 | Stoessel et al. | |
| 2019/0119291 | A1* | 4/2019 | Saito | H10K 85/6572 |
| 2020/0020866 | A1 | 1/2020 | Sakamoto et al. | |
| 2020/0216475 | A1 | 7/2020 | Yoon et al. | |

FOREIGN PATENT DOCUMENTS

| | | | | |
|---|---|---|---|---|
| CN | 106467553 | A | 3/2017 | |
| CN | 110590790 | A | 12/2019 | |
| CN | 117886837 | A * | 4/2024 | H10K 85/322 |
| EP | 3109253 | A1 | 12/2016 | |
| JP | 2011-184430 | A | 9/2011 | |
| JP | 2013-526548 | A | 6/2013 | |
| JP | 2014-520096 | A | 8/2014 | |
| WO | 2010/104047 | A1 | 9/2010 | |
| WO | 2011/099331 | A1 | 8/2011 | |
| WO | 2015/102118 | A1 | 7/2015 | |
| WO | 2019/132506 | A1 | 7/2019 | |

OTHER PUBLICATIONS

Nagamatsu, Kentaro, et al. "Reactions of 8-(triphenylphosphoimino) quinoline with aryl aldehydes and aryl isocyanates: formation of 2-aryl-4H-imidazo [4, 5, 1-ij] quinolines and related systems." Heterocycles 69 (2006): 167-178. (Year: 2006).*

International Search Report and Written Opinion received for PCT Patent Application No. PCT/EP2021/058563, mailed on Jun. 7, 2021, 15 pages (6 pages of English Translation and 9 pages of Original Document).

Wang et al., "Exploration of pyrazine-embedded antiaromatic polycyclic hydrocarbons generated by solution and on-surface azomethine ylide homocoupling," Nature Communications, vol. 8, No. 1948, Dec. 5, 2017, pp. 1-7.

* cited by examiner

*Primary Examiner* — Robert S Loewe
(74) *Attorney, Agent, or Firm* — DUANE MORRIS LLP

(57) ABSTRACT

The present invention relates to polycyclic compounds suitable for use in electronic devices, and to electronic devices, especially organic electroluminescent devices, comprising these compounds.

20 Claims, No Drawings

POLYCYCLIC COMPOUNDS FOR ORGANIC ELECTROLUMINESCENT DEVICES

CROSS-REFERENCE TO RELATED APPLICATIONS

This application is a national stage application (under 35 U.S.C. § 371) of PCT/EP2021/058563, filed Apr. 1, 2021, which claims benefit of European Application No. 20168237.4, filed Apr. 6, 2020, both of which are incorporated herein by reference in their entirety.

The present invention relates to polycyclic compounds for use in electronic devices, especially in organic electroluminescent devices, and to electronic devices, especially organic electroluminescent devices comprising these heterocyclic compounds.

Emitting materials used in organic electroluminescent devices are frequently phosphorescent organometallic complexes or fluorescent compounds. There is generally still a need for improvement in electroluminescent devices.

WO 2010/104047 A1 and WO 2019/132506 A1 disclose polycyclic compounds that can be used in organic electroluminescent devices. There is no disclosure of compounds according to the present invention. In addition, antiaromatic properties of compounds are examined by Wang et al., in Nature Communications|8: 1948. However, there is no description of the use of these compounds in organic electroluminescent devices by Wang et al.

In general terms, there is still a need for improvement in these heterocyclic compounds, for example for use as emitters, especially as fluorescent emitters, particularly in relation to lifetime and color purity, but also in relation to the efficiency and operating voltage of the device.

It is therefore an object of the present invention to provide compounds which are suitable for use in an organic electronic device, especially in an organic electroluminescent device, and which lead to good device properties when used in this device, and to provide the corresponding electronic device.

More particularly, the problem addressed by the present invention is that of providing compounds which lead to a high lifetime, good efficiency and low operating voltage.

In addition, the compounds should have excellent processability, and the compounds should especially show good solubility.

A further problem addressed by the present invention can be considered that of providing compounds suitable for use in a phosphorescent or fluorescent electroluminescent devices, especially as emitter. More particularly, a problem addressed by the present invention is that of providing emitters suitable for red, green or blue electroluminescent devices.

In addition, the compounds, especially when they are used as emitters in organic electroluminescent devices, should lead to devices having excellent color purity.

A further problem addressed by the present invention can be considered that of providing compounds suitable for use in phosphorescent or fluorescent electroluminescent devices, especially as a matrix material.

More particularly, a problem addressed by the present invention is that of providing matrix materials suitable for red-, yellow- and blue-phosphorescing electroluminescent devices.

In addition, the compounds, especially when they are used as matrix materials, as hole transport materials or as electron transport materials in organic electroluminescent devices, should lead to devices having excellent color purity.

A further problem can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, this object is achieved by particular compounds described in detail below that are of very good suitability for use in preferably electroluminescent devices and lead to organic electroluminescent devices that show very good properties, especially in relation to lifetime, color purity, efficiency and operating voltage. The present invention therefore provides these compounds and electronic devices, especially organic electroluminescent devices, comprising such compounds.

The present invention provides a compound comprising at least one structure of the formula (I), preferably a compound of the formula (I), Formula (I)

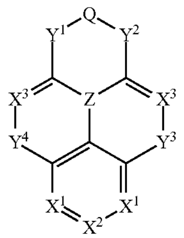

where the symbols and indices used are as follows:

Z is the same or different at each instance and is N or B;

Q is the same or different at each instance and is C═O, C(═O)—C(═O), $(R^d)_2C—C(R^d)_2$, $(R^d)_2C═C(R^d)$ or an aromatic or heteroaromatic ring system which has 5 to 60 aromatic ring atoms and binds to the $Y^1$ and $Y^2$ groups via two adjacent and mutually bonded carbon atoms and may be substituted in each case by one or more $R^d$ radicals;

$Y^1$, $Y^2$ is the same or different at each instance and is N(Ar), N(R), B(Ar), B(R), Al(Ar) or Al(R), preferably N(Ar), N(R), B(Ar) or B(R);

$Y^3$, $Y^4$ is the same or different at each instance and is N(Ar), N(R), P(Ar), P(R), P(═O)Ar, P(═O)R, P(═S)Ar, P(═S)R, B(Ar), B(R), Al(Ar), Al(R), Ga(Ar), Ga(R), C═O, $C(R)_2$, $Si(R)_2$, C═NR, C═NAr, $C═C(R)_2$, O, S, Se, S═O, or $SO_2$, preferably N(Ar), N(R), B(Ar), B(R), P(═O)R, P(═O)Ar, C═O, $C(R)_2$, $Si(R)_2$, O, S, Se, S═O, or $SO_2$, more preferably C═O, N(Ar) or B(Ar);

Ar is the same or different at each instance and is an aromatic or heteroaromatic ring system which has 5 to 60 aromatic ring atoms and may be substituted by one or more R radicals; the Ar group here may form a ring system with an Ar or R radical or a further group;

$X^1$ is the same or different at each instance and is N, $CR^a$, CAr, or C if a ring system is formed by a bond to an Ar or R radical or a further group, preferably $CR^a$ or C, with the proviso that not more than two of the $X^1$, $X^2$ groups in one cycle are N;

$X^2$ is the same or different at each instance and is N, $CR^b$ or CAr, preferably $CR^b$, with the proviso that not more than two of the $X^1$, $X^2$ groups in one cycle are N;

$X^3$ is the same or different at each instance and is N, $CR^c$, CAr, or C if a ring system is formed by a bond to an Ar or R radical or a further group, preferably $CR^c$ or C;

R, $R^a$, $R^b$, $R^c$, $R^d$ is the same or different at each instance and is H, D, OH, F, Cl, Br, I, CN, $NO_2$, $N(Ar')_2$, $N(R^1)_2$, C(═O)OAr, C(═O)$OR^1$, C(═O)$N(Ar')_2$, C(═O)$N(R^1)_2$, $C(Ar')_3$, $C(R^1)_3$, $Si(Ar')_3$, $Si(R^1)_3$, $B(Ar')_2$, $B(R^1)_2$, C(═O)Ar', C(═O)$R^1$, P(═O)$(Ar')_2$, P(═O)$(R^1)_2$, $P(Ar')_2$, $P(R^1)_2$, S(═O)Ar, S(═O)$R^1$, S(═O)$_2$Ar', S(═O)$_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C$═$CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —Se—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R, $R^a$, $R^b$, $R^c$, $R^d$ radicals may also form a ring system together or with a further group;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R)_2$, $Si(R)_2$, C═O, C═$NR^1$, C═$C(R)_2$, O, S, S═O, $SO_2$, $N(R^1)$, $P(R^1)$ and P(═O)$R^1$;

$R^1$ is the same or different at each instance and is H, D, F, Cl, Br, I, CN, $NO_2$, $N(Ar'')_2$, $N(R^2)_2$, C(═O)OAr', C(═O)$OR^2$, C(═O)Ar'', C(═O)$R^2$, P(═O)$(Ar')_2$, $P(Ar')_2$, $B(Ar'')_2$, $B(R^2)_2$, C(Ar')s, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by —$R^2C$═$CR^2$—, —C≡C—, $Si(R^2)_2$, C═O, C═S, C═Se, C═$NR^2$, —C(═O)O—, —C(═O)$NR^2$—, $NR^2$, P(═O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent, $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C═O, C═$NR^2$, C═$C(R^2)_2$, O, S, S═O, $SO_2$, $N(R^2)$, $P(R^2)$ and P(═O)$R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, preferably adjacent substituents $R^2$ together may form a ring system.

An aryl group in the context of this invention contains 6 to 60 carbon atoms, preferably 6 to 40 carbon atoms; a heteroaryl group in the context of this invention contains 2 to 60 carbon atoms, preferably 2 to 40 carbon atoms, and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatics joined to one another by a single bond, for example biphenyl, by contrast, are not referred to as an aryl or heteroaryl group but as an aromatic ring system.

An electron-deficient heteroaryl group in the context of the present invention is a heteroaryl group having at least one heteroaromatic six-membered ring having at least one nitrogen atom. Further aromatic or heteroaromatic five-membered or six-membered rings may be fused onto this six-membered ring. Examples of electron-deficient heteroaryl groups are pyridine, pyrimidine, pyrazine, pyridazine, triazine, quinoline, quinazoline or quinoxaline.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a non-aromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 40 carbon atoms, preferably 1 to 20 carbon atoms, and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 or 5-40 aromatic ring atoms and may also be substituted in each case by the abovementioned radicals and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

The wording that two or more radicals together may form a ring, in the context of the present description, should be understood to mean, inter alia, that the two radicals are joined to one another by a chemical bond with formal elimination of two hydrogen atoms. This is illustrated by the following scheme:

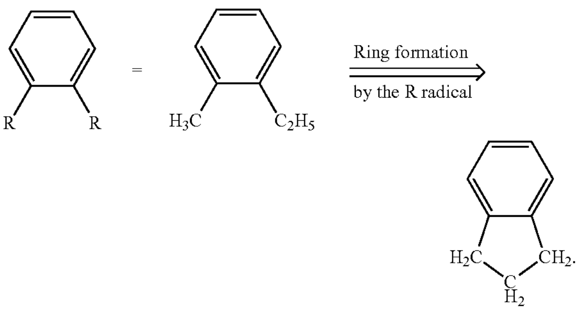

In addition, however, the abovementioned wording shall also be understood to mean that, if one of the two radicals is hydrogen, the second radical binds to the position to which the hydrogen atom was bonded, forming a ring. This will be illustrated by the following scheme:

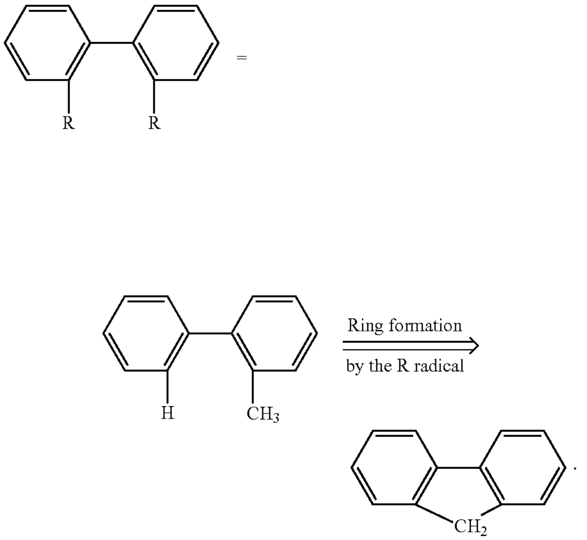

It may preferably be the case that, in formula (I), not more than four, preferably not more than two, $X^1$, $X^2$ and $X^3$ groups are N; more preferably, all $X^1$, $X^2$ and $X^3$ groups are $CR^a$, $CR^b$, $CR^c$, or C if an R or Ar group forms a ring system via a bond.

In a preferred configuration, the compounds of the invention may comprise at least one structure of the formula (II); more preferably, the compounds of the invention may be selected from the compounds of the formula (II):

Formula (II)

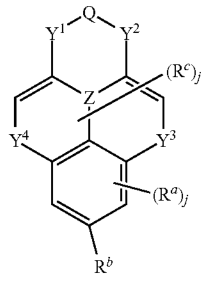

where $Y^1$, $Y^2$, $Y^3$, $Y^4$, Z, Q, $R^a$, $R^b$ and $R^c$ have the definitions given above, especially formula (I), and the index j is 0, 1 or 2, preferably 0 or 1, where the sum total of the indices j is preferably 0, 1 or 2.

In a preferred configuration, in formula (I) and/or (II), it may be the case that the Q group is the same or different at each instance and is selected from C═O, C(═O)—C(═O), $(R^d)_2C$═$C(R^d)$ or phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, isoquinoline, quinazoline, quinoxaline, phenanthrene or triphenylene, each of which binds to the $Y^1$ and $Y^2$ groups via two adjacent and mutually bonded carbon atoms and may be substituted by one or more $R^d$ radicals.

In a further preferred embodiment, it may be the case that the compounds of the invention comprise a structure of the formulae (IIIa) to (IIIk), where the compounds of the invention may more preferably be selected from the compounds of the formulae (IIIa) to (IIIk)

Formula (IIIa)

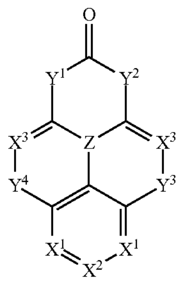

Formula (IIIb)

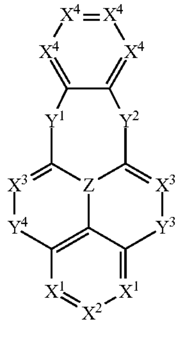

-continued

Formula (IIIc)

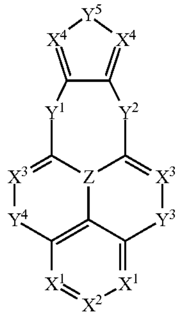

Formula (IIId)

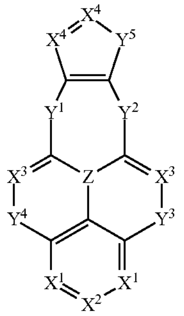

Formula (IIIe)

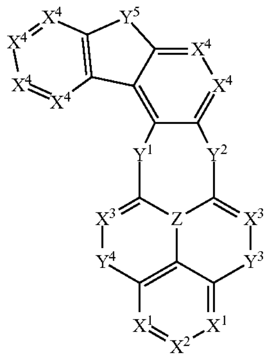

Formula (IIIf)

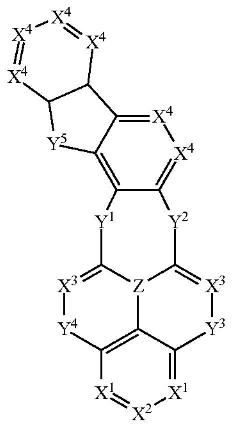

-continued

Formula (IIIg)

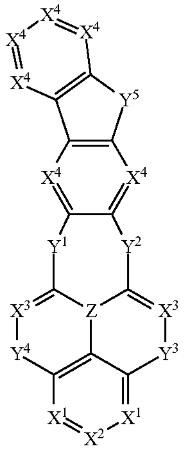

Formula (IIIh)

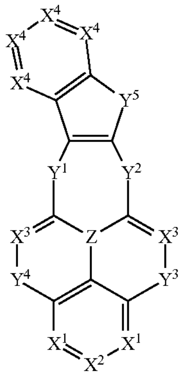

Formula (IIIi)

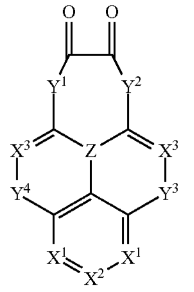

Formula (IIIj)

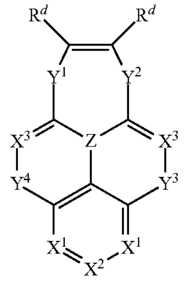

-continued

Formula (IIIk)

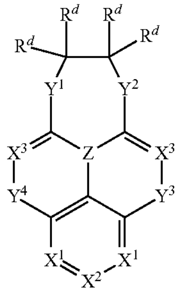

where the symbols $Y^1$, $Y^2$, $Y^3$, $Y^4$, $X^1$, $X^2$, $X^3$, $R^d$ and Z have the definitions given above, especially for formula (I), $X^4$ is the same or different at each instance and is N, $CR^d$, or C if a ring system is formed by a bond to an Ar or R radical or a further group, preferably $CR^d$ or C, and $Y^5$ is $C(R)_2$, NR, NA, BR, BA, O or S, preferably $C(R)_2$, NAr' or O, where R and Ar' have the definitions given above, especially for formula (I).

In this context, structures of the formulae (IIIa) to (IIIj) are preferred, structures of the formulae (IIIa) and (IIIb) are particularly preferred, and structures of the formula (IIIa) are especially preferred.

It may preferably be the case that, in formulae (IIIa) to (IIIk), not more than four, preferably not more than two, $X^1$, $X^2$, $X^3$, $X^4$ groups are N; more preferably, all $X^1$, $X^2$, $X^3$, $X^4$ groups are $CR^a$, $CR^b$, $CR^c$, $CR^d$, or C if an R or Ar group forms a ring system via a bond.

In a further-preferred embodiment, it may be the case that the compounds of the invention comprise a structure of the formula (IVa) to (IVn), where the compounds of the invention may more preferably be selected from the compounds of the formulae (IVa) to (IVn):

Formula (IVa)

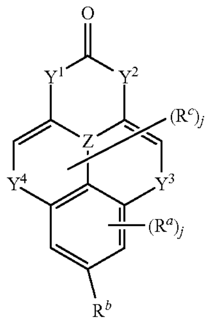

Formula (IVb)

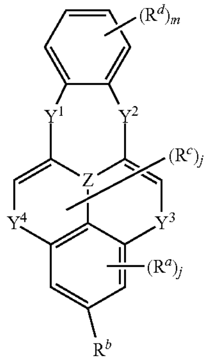

-continued
Formula (IVc)
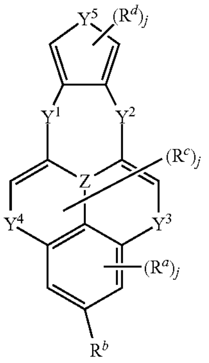
Formula (IVd)
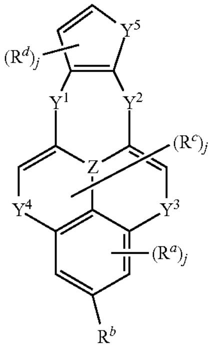
Formula (IVe)
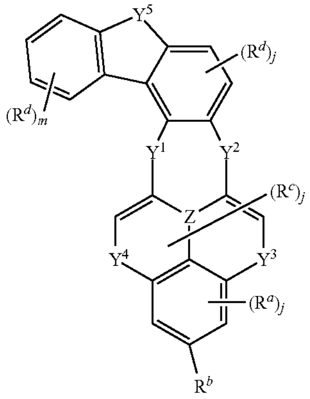
Formula (IVf)
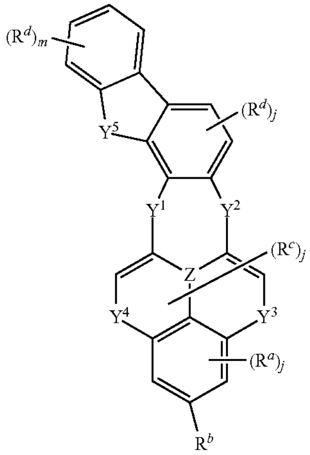
-continued
Formula (IVg)
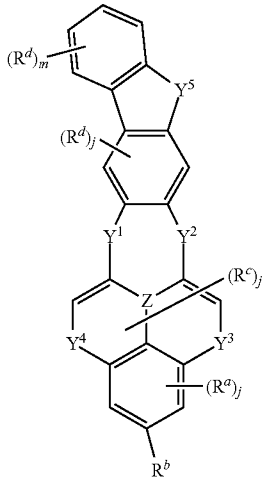
Formula (IVh)
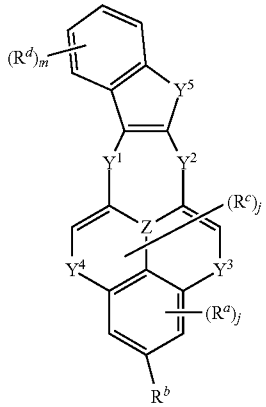
Formula (IVi)
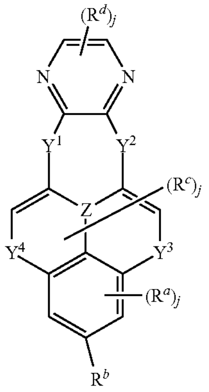

-continued

Formula (IVj)

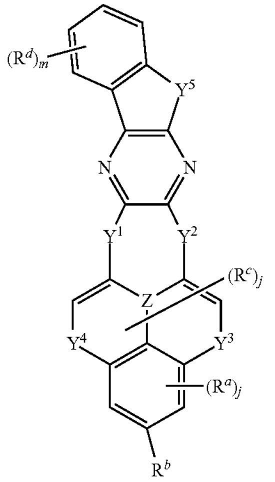

Formula (IVk)

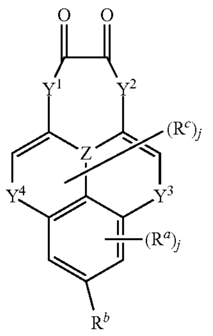

Formula (IVm)

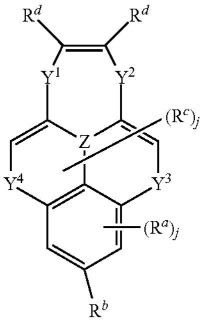

Formula (IVn)

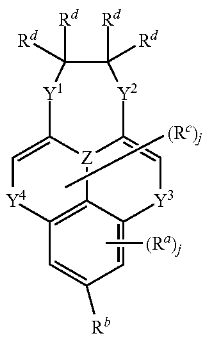

where the symbols $Y^1$, $Y^2$, $Y^3$, $Y^4$, Z, $R^a$, $R^b$, $R^c$ and $R^d$ have the definitions given above, especially for formula (I), the index j is 0, 1 or 2, preferably 0 or 1, the index m is 0, 1, 2, 3 or 4, preferably 0, 1 or 2, and $Y^5$ is $C(R)_2$, NR, NAr', BR, BAr, O or S, preferably $C(R)_2$, NAr' or O, where R and Ar' have the definitions given above, especially for formula (I).

In this context, structures/compounds of the formulae (IVa) to (IVm) are preferred, structures/compounds of the formulae (IVa) and (IVb) are particularly preferred, and structures/compounds of the formula (IVa) are especially preferred.

The sum total of the indices j and m in structures/compounds of the formulae (IVa) to (IVn) is preferably not more than 8, especially preferably not more than 6 and more preferably not more than 4.

In addition, in formulae (I), (II), (IIIa) to (IIIk), (IVa) to (IVn) and/or the preferred embodiments of these formulae shown below, inter alia, it may be the case that Z is N and at least one, preferably two, of the $Y^1$, $Y^2$ groups is/are B(Ar), B(R), Al(Ar), or Al(R), preferably B(Ar) or B(R).

Configurations in which Z is N and at least one, preferably two, of the $Y^1$, $Y^2$ groups is/are B(Ar), B(R), Al(Ar), or Al(R), preferably B(Ar) or B(R), may advantageously be used as emitter.

Moreover, in formulae (I), (II), (IIIa) to (IIIk), (IVa) to (IVn) and/or the preferred embodiments of these formulae shown below, inter alia, it may be the case that Z is N and at least one, preferably two, of the $Y^1$, $Y^2$ groups is/are N(Ar) or N(R), preferably N(Ar).

Embodiments in which Z is N and at least one, preferably two, of the $Y^1$, $Y^2$ groups is/are N(Ar) or N(R), preferably N(Ar), may advantageously be used especially as hole conductor material.

In a further configuration, in formulae (I), (II), (IIIa) to (IIIk), (IVa) to (IVn) and/or the preferred embodiments of these formulae set out hereinafter, inter alia, it may be the case that at least one, preferably two, of the $Y^1$, $Y^2$ groups represent(s) N(Ar) or N(R) and at least one, preferably two, of the $Y^3$, $Y^4$ groups are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar). Configurations in which at least one, preferably two, of the $Y^1$, $Y^2$ groups represent(s) N(Ar) or N(R) and at least one, preferably two, of the $Y^3$, $Y^4$ groups are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar), may advantageously be used as emitter.

In a further configuration, in formulae (I), (II), (IIIa) to (IIIk), (IVa) to (IVn) and/or the preferred embodiments of these formulae set out hereinafter, inter alia, it may be the case that at least one, preferably two, of the $Y^1$, $Y^2$ groups represent(s) N(Ar) or N(R) and at least one, preferably two, of the $Y^3$, $Y^4$ groups is/are N(Ar), N(R), P(Ar), P(R), O, S or Se, preferably N(Ar), N(R), O or S, more preferably N(Ar).

Embodiments in which at least one, preferably two, of the $Y^1$, $Y^2$ groups represent(s) N(Ar) or N(R) and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used especially as hole conductor material.

Moreover, in formulae (I), (II), (IIIa) to (IIIk), (IVa) to (IVn) and/or the preferred embodiments of these formulae shown below, inter alia, it may be the case that Z is B and at least one, preferably two, of the $Y^1$, $Y^2$ groups is/are N(Ar) or N(R), preferably N(Ar). Configurations in which Z is B and at least one, preferably two, of the $Y^1$, $Y^2$ groups is/are N(Ar) or N(R), preferably N(Ar), may advantageously be used as emitter.

In addition, in formulae (I), (II), (IIIa) to (IIIk), (IVa) to (IVn) and/or the preferred embodiments of these formulae shown below, inter alia, it may be the case that Z is B and at least one, preferably two, of the $Y^1$, $Y^2$ groups is/are B(Ar), B(R), Al(Ar), or Al(R), preferably B(Ar) or B(R).

Embodiments in which Z is N and at least one, preferably two, of the $Y^1$, $Y^2$ groups is/are B(Ar), B(R), Al(Ar), or Al(R), preferably B(Ar) or B(R), may advantageously be used especially as electron transport material.

In a further configuration, in formulae (I), (II), (IIIa) to (IIIk), (IVa) to (IVn) and/or the preferred embodiments of these formulae set out hereinafter, inter alia, it may be the case that at least one, preferably two, of the $Y^1$, $Y^2$ groups represent(s) B(Ar), B(R), Al(Ar) or Al(R), preferably B(Ar) or B(R), more preferably B(Ar), and at least one, preferably two, of the $Y^3$, $Y^4$ groups is/are N(Ar), N(R), P(Ar), P(R), O, S or Se, preferably N(Ar), N(R), O or S, more preferably N(Ar). Configurations in which at least one, preferably two, of the $Y^1$, $Y^2$ groups represent(s) B(Ar), B(R), Al(Ar) or Al(R), preferably B(Ar) or B(R), more preferably B(Ar), and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used as emitter.

In a further configuration, in formulae (I), (II), (IIIa) to (IIIk), (IVa) to (IVn) and/or the preferred embodiments of these formulae set out hereinafter, inter alia, it may be the case that at least one, preferably two, of the $Y^1$, $Y^2$ groups represent(s) B(Ar), B(R), Al(Ar) or Al(R), preferably B(Ar) or B(R), more preferably B(Ar), and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar).

Embodiments in which at least one, preferably two, of the $Y^1$, $Y^2$ groups represent(s) B(Ar), B(R), Al(Ar) or Al(R), preferably B(Ar) or B(R), more preferably B(Ar), and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar), may advantageously be used especially as electron transport material.

More preferably, the compounds comprise at least one structure of the formulae (Va) to (Vk); more preferably, the compounds are selected from compounds of the formulae (Va) to (Vk):

Formula (Va)

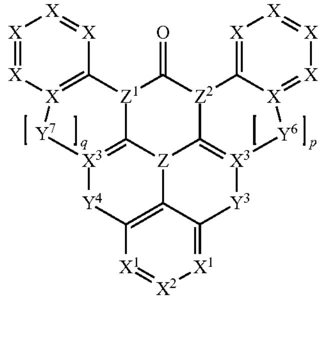

-continued

Formula (Vb)

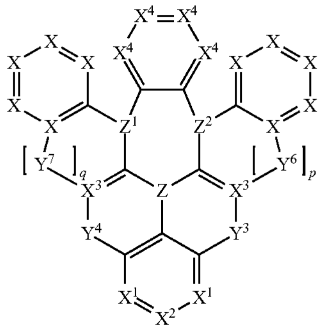

Formula (Vc)

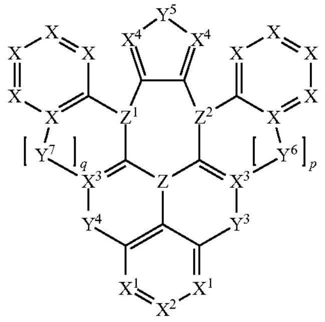

Formula (Vd)

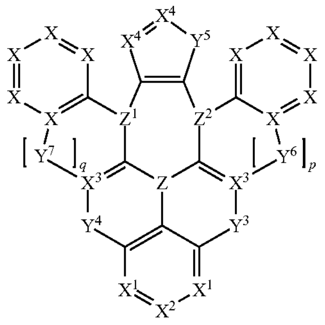

Formula (Ve)

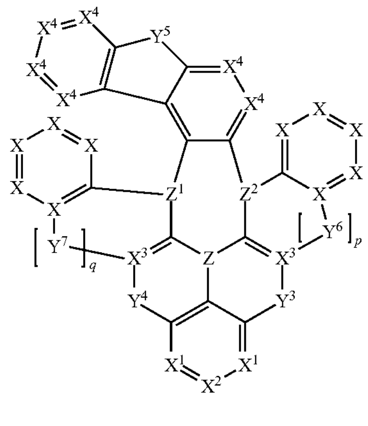

-continued

Formula (Vf)

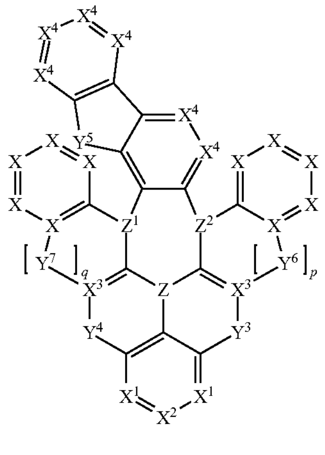

Formula (Vg)

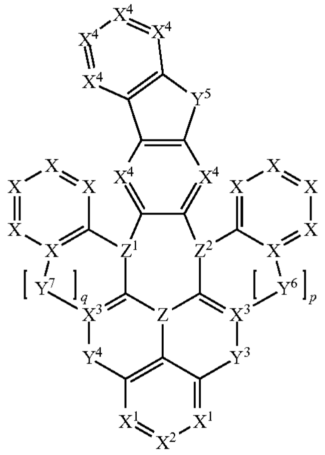

Formula (Vh)

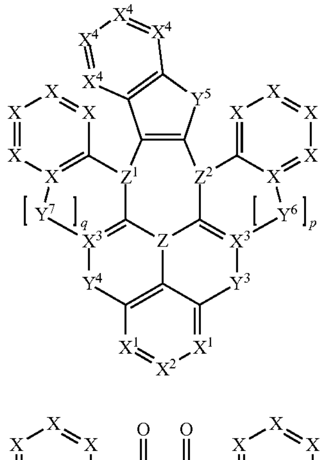

Formula (Vi)

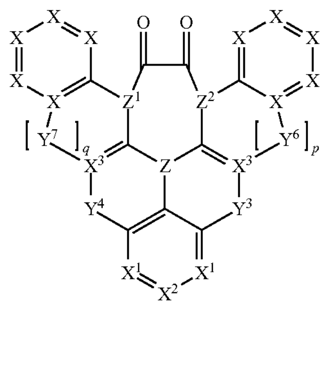

-continued

Formula (Vj)

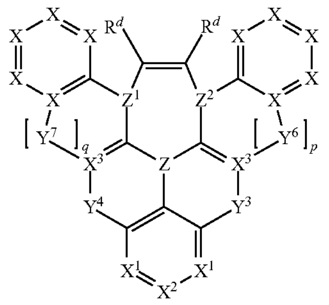

Formula (Vk)

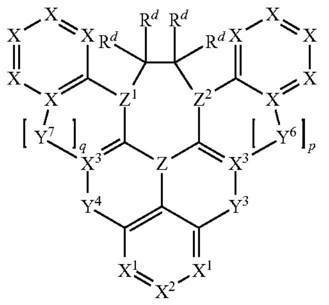

where the symbol $Y^3$, $Y^4$, $X^1$, $X^2$, $X^3$ and Z have the definitions given above, especially for formula (I), the symbols $X^4$ and $Y^5$ have the definitions given above, especially for formula (IIIa) to (IIIk), and the further symbols are defined as follows:

$Z^1$, $Z^2$ is the same or different at each instance and is N, B or Al, preferably N or B;

x is the same or different at each instance and is N, CR, or C if a ring system is formed by a bond to an $X^3$ radical or a further group, preferably CR or C, with the proviso that not more than two of the X groups in one cycle are N, where R is as defined above, especially for formula (I);

$Y^6$, $Y^7$ is the same or different at each instance and is a bond, N(Ar'), N(R), P(Ar'), P(R), P(=O)Ar', P(=O)R, P(=S)Ar', P(=S)R, B(Ar'), B(R), Al(Ar'), Al(R), Ga(Ar'), Ga(R), C=O, $C(R)_2$, $Si(R)_2$, C=NR, C=NAr', $C=C(R)_2$, O, S, Se, S=O, or $SO_2$, preferably a bond, N(Ar'), N(R), B(Ar'), B(R), P(=O)R, P(=O)Ar, C=O, $C(R)_2$, $Si(R)_2$, O, S, Se, S=O, or $SO_2$, more preferably a bond, where R and Ar' have the definitions given above, especially for formula (I);

p, q is the same or different at each instance and is 0 or 1, where 0 means that the corresponding group is absent.

In this context, structures/compounds of the formulae (Va) to (Vj) are preferred, structures/compounds of the formulae (Va) and (Vb) are particularly preferred, and structures/compounds of the formula (Va) are especially preferred.

It may further be the case that, in formulae (Va) to (Vk), not more than four, preferably not more than two, X, $X^1$, $X^2$, $X^3$, $X^4$ groups are N; more preferably, all X, $X^1$, $X^2$, $X^3$, $X^4$ groups are CR, $CR^a$, $CR^b$, $CR^c$, $CR^d$, or C if a ring system is formed by a bond.

More preferably, the compounds comprise at least one structure of the formulae (VI-1) to (VI-39); more preferably, the compounds are selected from compounds of the formulae (VI-1) to (VI-39):

-continued
Formula (VI-1)
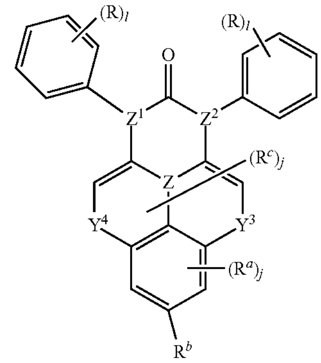
Formula (VI-2)
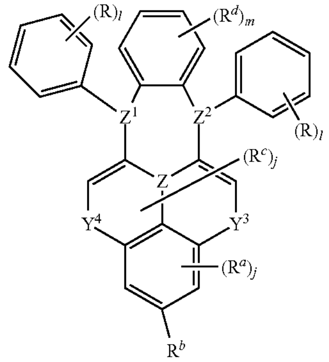
Formula (VI-3)
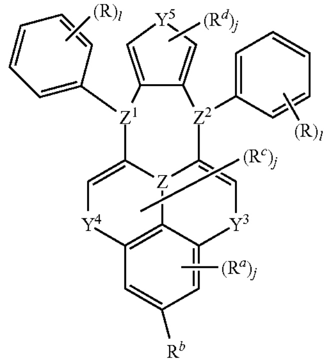
Formula (VI-4)
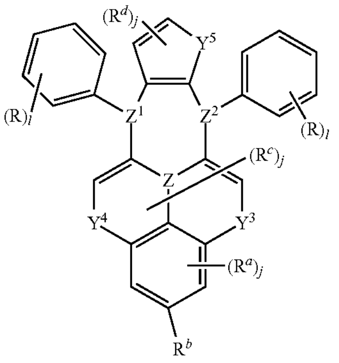
Formula (VI-5)
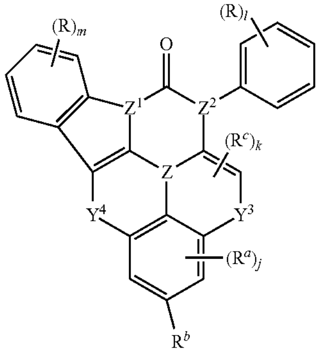
Formula (VI-6)
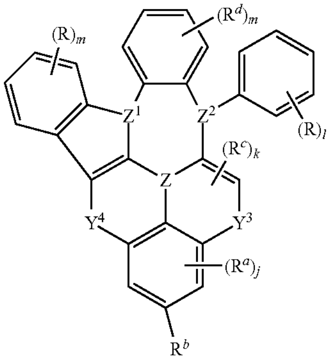
Formula (VI-7)
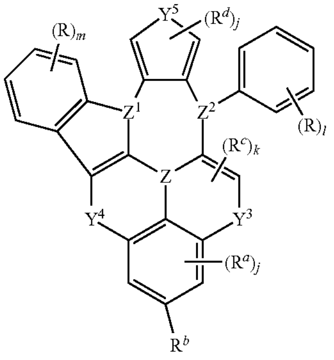
Formula (VI-8)
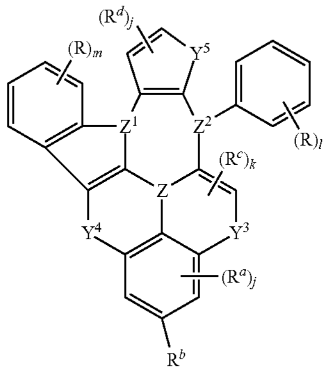

-continued
Formula (VI-9)
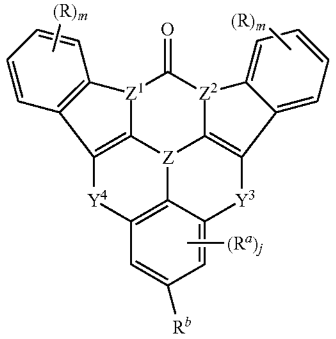
Formula (VI-10)
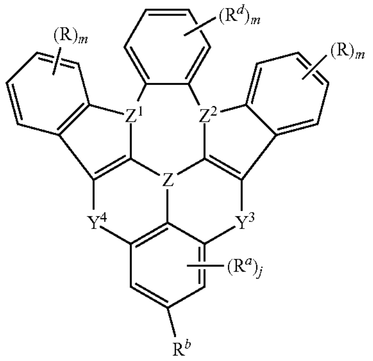
Formula (VI-11)
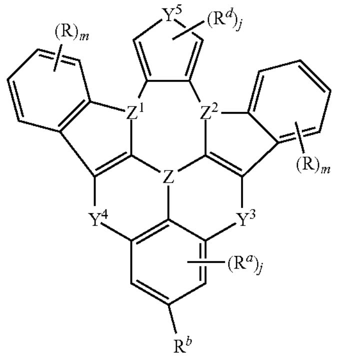
Formula (VI-12)
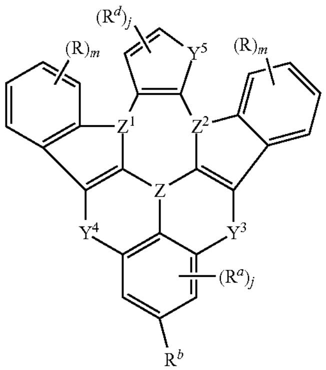
-continued
Formula (VI-13)
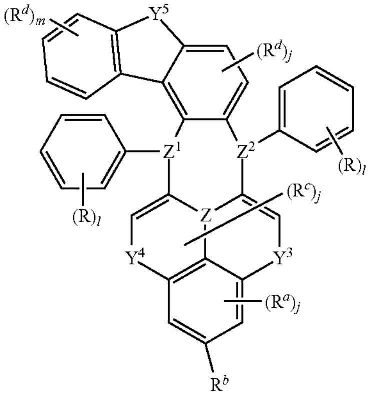
Formula (VI-14)
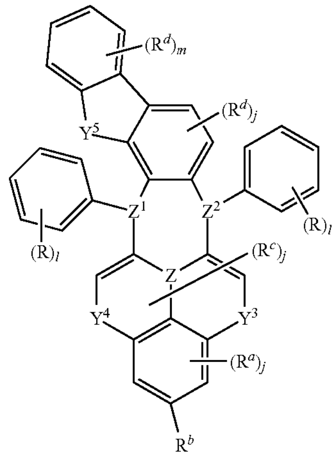
Formula (VI-15)
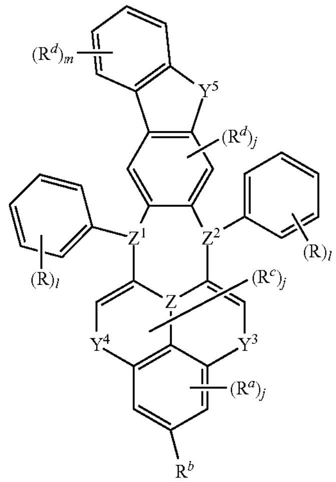

-continued
Formula (VI-16)
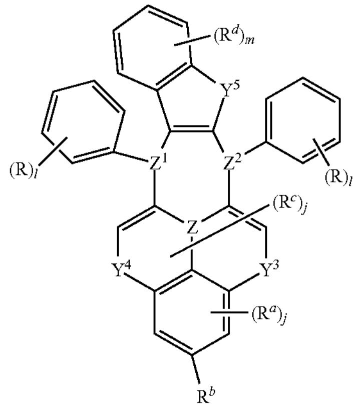
Formula (VI-17)
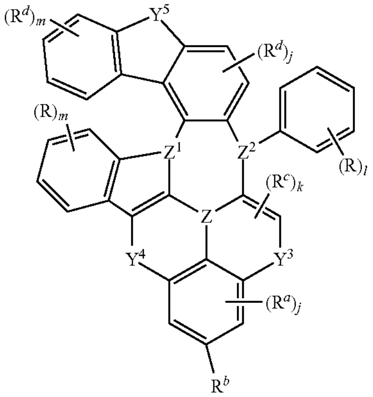
Formula (VI-18)
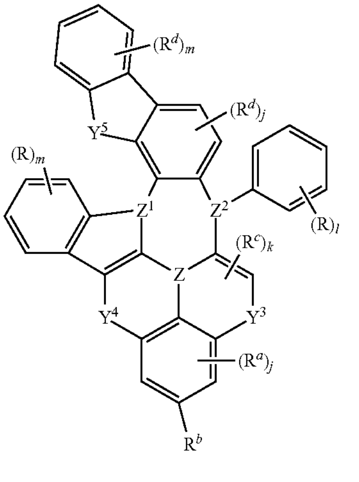
-continued
Formula (VI-19)
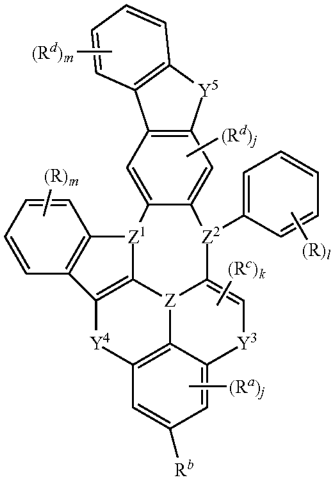
Formula (VI-20)
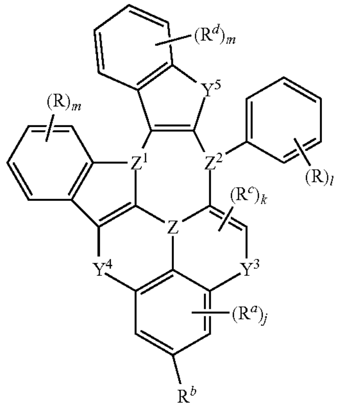
Formula (VI-21)
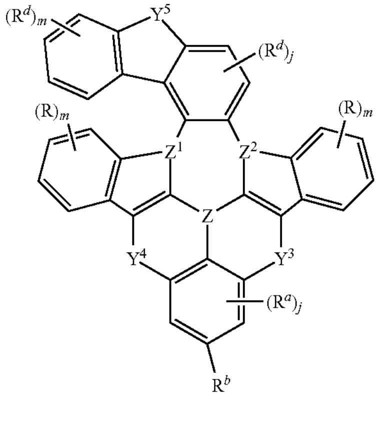

-continued
Formula (VI-22)
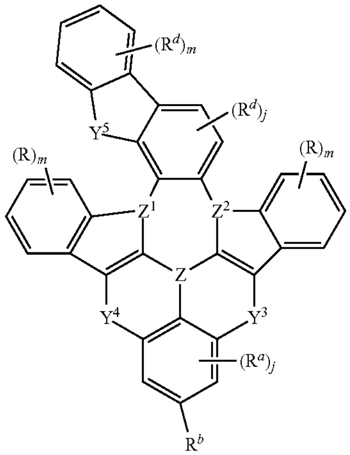
Formula (VI-23)
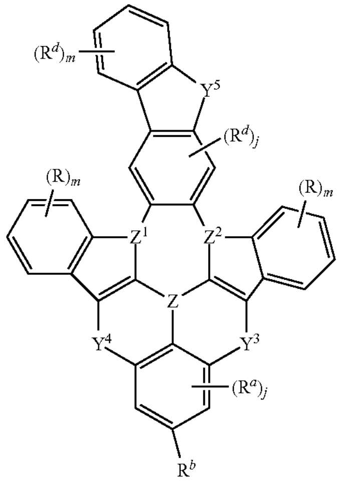
Formula (VI-24)
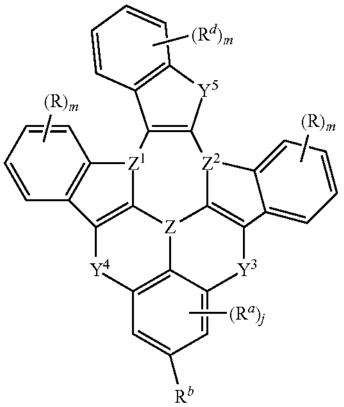
-continued
Formula (VI-25)
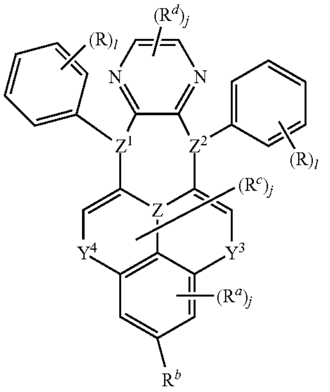
Formula (VI-26)
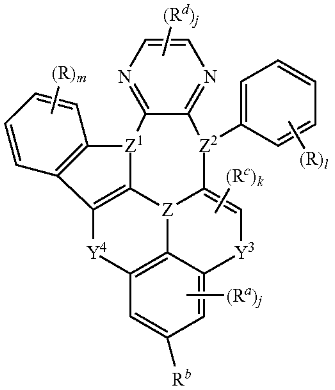
Formula (VI-27)
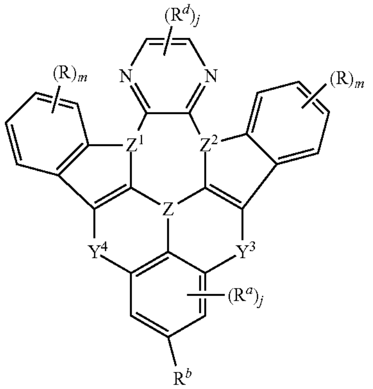

-continued
Formula (VI-28)
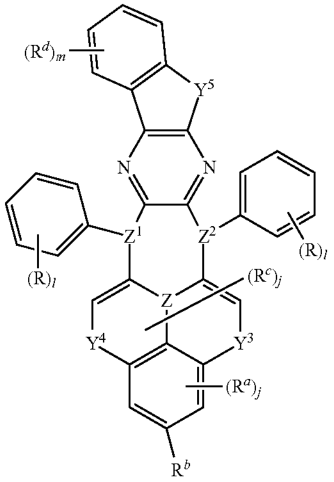
Formula (VI-29)
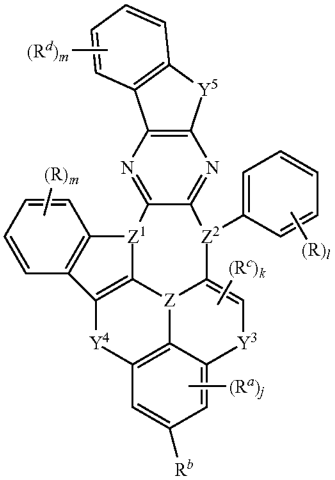
Formula (VI-30)
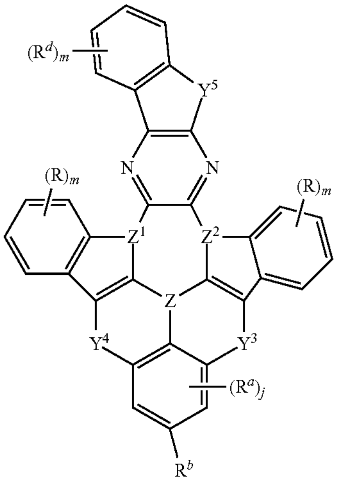
-continued
Formula (VI-31)
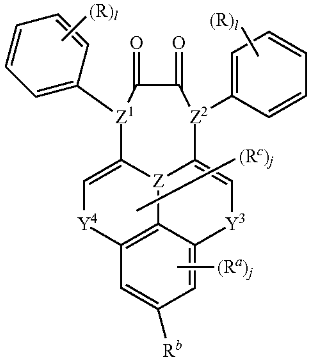
Formula (VI-32)
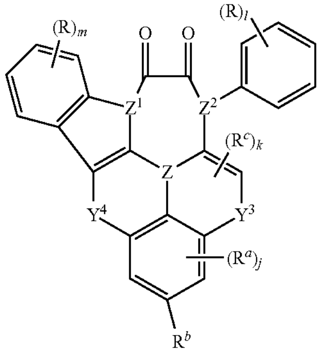
Formula (VI-33)
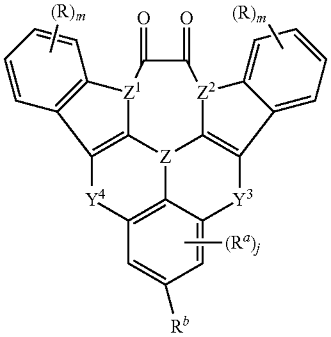
Formula (VI-34)
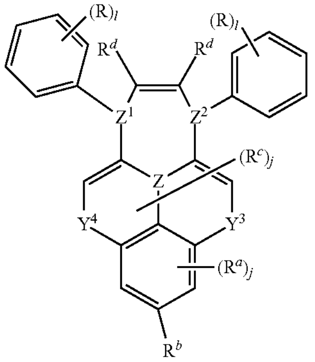

-continued

Formula (VI-35)

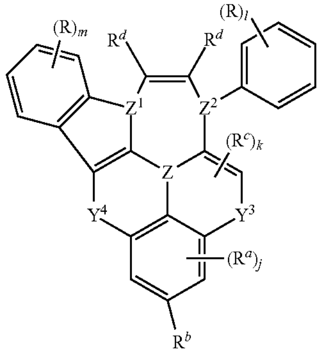

Formula (VI-36)

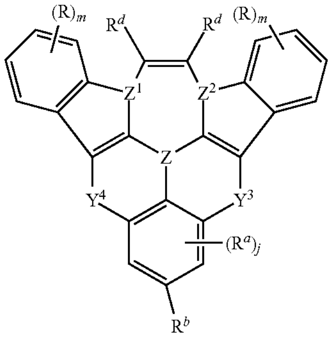

Formula (VI-37)

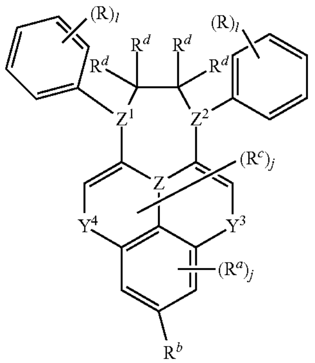

Formula (VI-38)

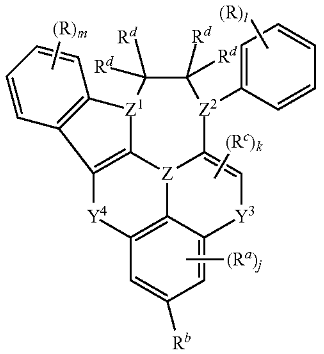

-continued

Formula (VI-39)

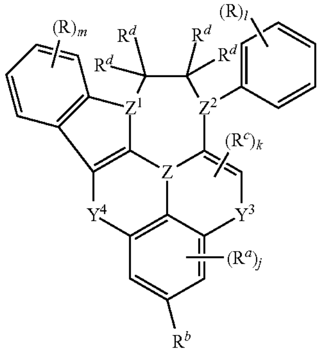

where $Y^3$, $Y^4$, Z, R, $R^a$, $R^b$, $R^c$ and $R^d$ have the definitions given above, especially for formula (I), and the further symbols have the following definition:

$Z^1$, $Z^2$ is the same or different at each instance and is N, B or Al, preferably N or B;

l is 0, 1, 2, 3, 4 or 5, preferably 0, 1 or 2;

m is 0, 1, 2, 3 or 4, preferably 0, 1 or 2;

j is 0, 1 or 2, preferably 0 or 1;

k is 0 or 1; and $Y^5$ is $C(R)_2$, NR, NA, BR, BAr', O or S, preferably $C(R)_2$, NAr' or O, where R and Ar' have the definitions given above, especially for formula (I).

Preference is given here to structures/compounds of the formulae (VI-1), (VI-2), (VI-5), (VI-6), (VI-9) and (VI-10), particular preference to structures/compounds of the formulae (VI-1), (VI-5) and (VI-9).

In structures of the formulae (VI-1) to (VI-39), it may be the case that the sum total of the indices j, k, l and m is preferably not more than 8, especially preferably not more than 6 and more preferably not more than 4.

In addition, in formulae (IIIa) to (IIIk), (IVa) to (IVn), (Va) to (Vk), (VI-1) to (VI-39) and/or the preferred embodiments of these formulae detailed below, inter alia, it may be the case that the two $Y^5$ groups are the same.

Furthermore, in formulae (IIIa) to (IIIk), (IVa) to (IVn), (Va) to (Vk), (VI-1) to (VI-39) and/or the preferred embodiments of these formulae detailed below, inter alia, it may be the case that the two $Y^5$ groups are different.

In addition, in formulae (I), (II), (IIIa) to (IIIk), (IVa) to (IVn), (Va) to (Vk), (VI-1) to (VI-39) and/or the preferred embodiments of these formulae set out hereinafter, inter alia, it may be the case that Z is N and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar). Configurations in which Z is N and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$ may advantageously be used as emitter.

Moreover, in formulae (I), (II), (IIIa) to (IIIk), (IVa) to (IVn), (Va) to (Vk), (VI-1) to (VI-39) and/or the preferred embodiments of these formulae shown below, inter alia, it may be the case that Z is N and at least one, preferably two, of the $Y^3$, $Y^4$ groups is/are N(Ar), N(R), P(Ar), P(R), O, S or Se, preferably N(Ar), N(R), O or S, more preferably N(Ar).

Embodiments in which Z is N and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used especially as hole conductor material.

In addition, in formulae (Va) to (Vk), (VI-1) to (VI-39) and/or the preferred embodiments of these formulae shown below, inter alia, it may be the case that Z is N and at least one, preferably two, of the $Z^1$, $Z^2$ groups is/are B or Al, preferably B. Configurations in which Z is N and at least one, preferably two, of the $Z^1$, $Z^2$ groups is/are B or Al, preferably B, may advantageously be used as emitter.

Moreover, in formulae (Va) to (Vk), (VI-1) to (VI-39) and/or the preferred embodiments of these formulae detailed below inter alia, it may be the case that Z is N and at least one, preferably two, of the $Z^1$, $Z^2$ groups is/are N.

Embodiments in which Z is N and at least one, preferably two, of the $Z^1$, $Z^2$ groups is/are N may advantageously be used especially as hole conductor material.

In a further configuration, in formulae (I), (II), (IIIa) to (IIIk), (IVa) to (IVn), (Va) to (Vk), (VI-1) to (VI-39) and/or the preferred embodiments of these formulae shown below, inter alia, it may be the case that Z is B and at least one, preferably two, of the $Y^3$, $Y^4$ groups is/are N(Ar), N(R), P(Ar), P(R), O, S or Se, preferably N(Ar), N(R), O or S, more preferably N(Ar). Configurations in which Z is B and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used as emitter.

In a further configuration, in formulae (Va) to (Vk), (VI-1) to (VI-39) and/or the preferred embodiments of these formulae detailed below inter alia, it may be the case that Z is B and at least one, preferably two, of the $Z^1$, $Z^2$ groups is/are N. Embodiments in which Z is B and at least one, preferably two, of the $Z^1$, $Z^2$ groups is/are N may advantageously be used especially as emitter.

Moreover, in formulae (I), (II), (IIIa) to (IIIk), (IVa) to (IVn), (Va) to (Vk), (VI-1) to (VI-39) and/or the preferred embodiments of these formulae set out hereinafter, inter alia, it may be the case that Z is B and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably C=O, B(Ar), B(R), P(=O)Ar, P(=O)R, S=O or $SO_2$, more preferably C=O, B(R) or B(Ar). Configurations in which Z is B and at least one, preferably two, of the $Y^3$, $Y^4$ groups represent(s) B(Ar), B(R), Al(Ar), Al(R), Ga(Ar), Ga(R), P(=O)Ar, P(=O)R, C=O, S=O or $SO_2$, preferably C=O, B(Ar), B(R), P(=O)Ar, P(=O)R, S=O or $SO_2$, more preferably C=O, B(R) or B(Ar), may advantageously be used as electron transport material.

In addition, in formulae (Va) to (Vk), (VI-1) to (VI-39) and/or the preferred embodiments of these formulae shown below, inter alia, it may be the case that Z is B and at least one, preferably two, of the $Z^1$, $Z^2$ groups is/are B or Al, preferably B.

Embodiments in which Z is B and at least one, preferably two, of the $Z^1$, $Z^2$ groups is/are B or Al, preferably B, may advantageously be used especially as electron transport material.

In a further configuration, in formulae (Va) to (Vk), (VI-1) to (VI-39) and/or the preferred embodiments of these formulae set out hereinafter, inter alia, it may be the case that at least one, preferably two, of the $Z^1$, $Z^2$ groups represent(s) N and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar). Configurations in which at least one, preferably two, of the $Z^1$, $Z^2$ groups represent(s) N and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar), may advantageously be used as emitter.

In a further configuration, in formulae (Va) to (Vk), (VI-1) to (VI-39) and/or the preferred embodiments of these formulae set out hereinafter, inter alia, it may be the case that at least one, preferably two, of the $Z^1$, $Z^2$ groups represent(s) N and at least one, preferably two, of the $Y^3$, $Y^4$ groups is/are N(Ar), N(R), P(Ar), P(R), O, S or Se, preferably N(Ar), N(R), O or S, more preferably N(Ar).

Embodiments in which at least one, preferably two, of the $Z^1$, $Z^2$ groups represent(s) N and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used especially as hole conductor material.

In addition, in formulae (Va) to (Vk), (VI-1) to (VI-39) and/or the preferred embodiments of these formulae set out hereinafter, inter alia, it may be the case that at least one, preferably two, of the $Z^1$, $Z^2$ groups represent(s) B or Al, preferably B, and at least one, preferably two, of the $Y^3$, $Y^4$ groups is/are N(Ar), N(R), P(Ar), P(R), O, S or Se, preferably N(Ar), N(R), O or S, more preferably N(Ar).

Embodiments in which at least one, preferably two, of the $Z^1$, $Z^2$ groups represent(s) B or Al, preferably B, and at least one, preferably two, of the $Y^3$, $Y^4$ groups is/are N(Ar), N(R), P(Ar), P(R), O, S or Se, preferably N(Ar), N(R), O or S, more preferably N(Ar), may advantageously be used especially as emitter.

In addition, in formulae (Va) to (Vk), (VI-1) to (VI-39) and/or the preferred embodiments of these formulae set out hereinafter, inter alia, it may be the case that at least one, preferably two, of the $Z^1$, $Z^2$ groups represent(s) B or Al, preferably B, and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar).

Embodiments in which at least one, preferably two, of the $Z^1$, $Z^2$ groups represent(s) B or Al, preferably B, and at least one, preferably two, of the $Y^3$, $Y^4$ groups is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar), may advantageously be used especially as electron transport material.

More preferably, the compounds comprise at least one structure of the formulae (VII-1) to (VII-18); more preferably, the compounds are selected from compounds of the formulae (VII-1) to (VII-18):

-continued
Formula (VII-1)
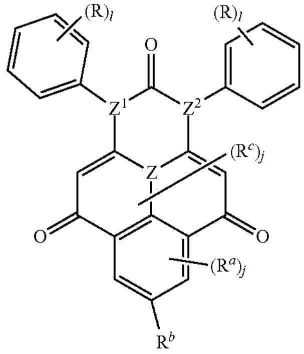
Formula (VII-2)
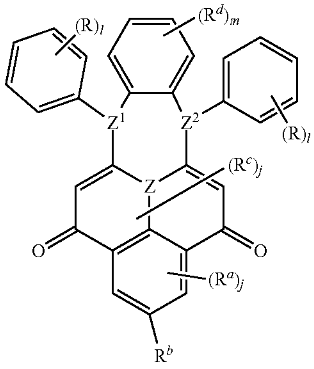
Formula (VII-3)
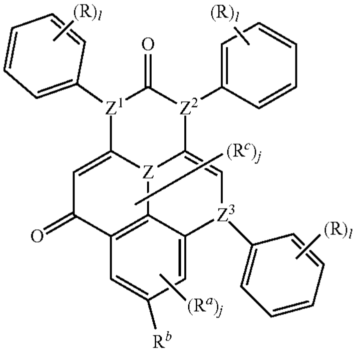
Formula (VII-4)
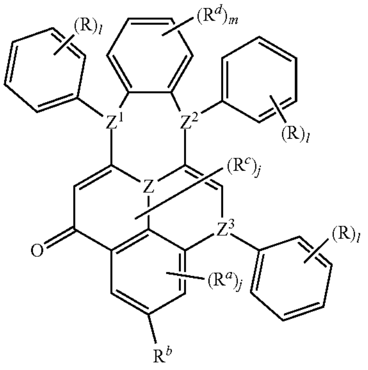
Formula (VII-5)
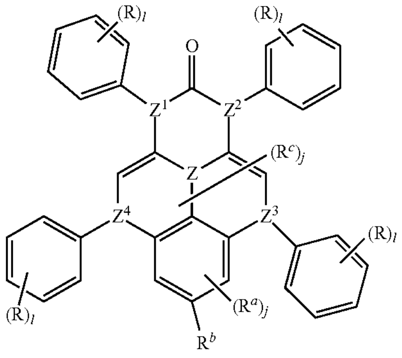
Formula (VII-6)
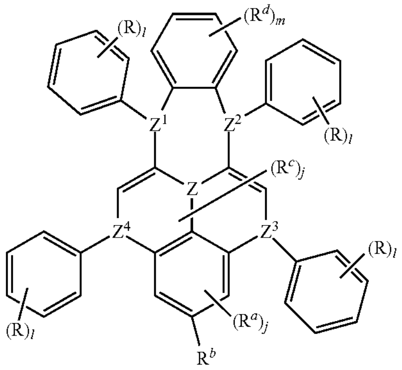
Formula (VII-7)
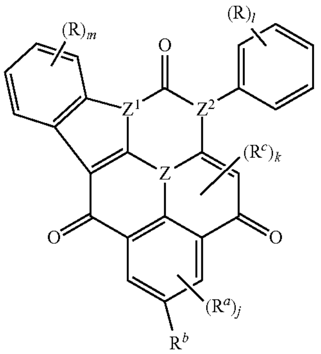
Formula (VII-8)
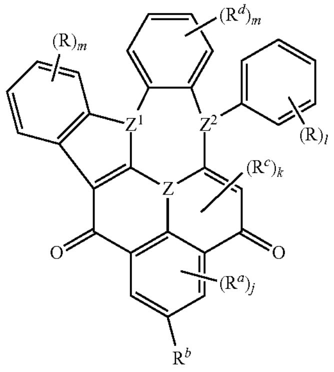

-continued
(VII-9)
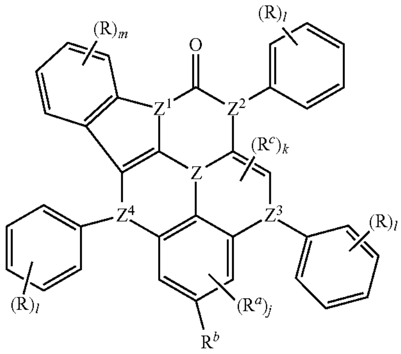
(VII-10)
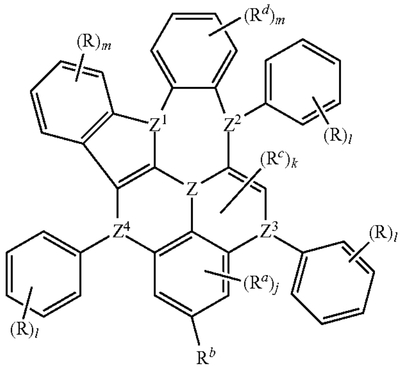
(VII-11)
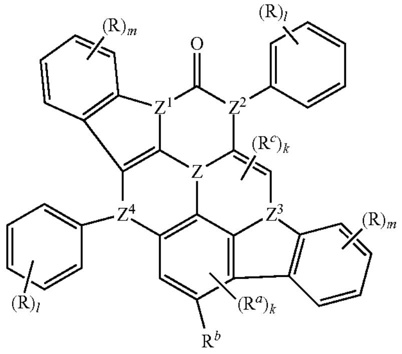
(VII-12)
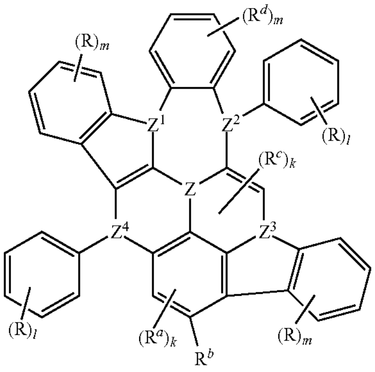
-continued
Formula (VII-13)
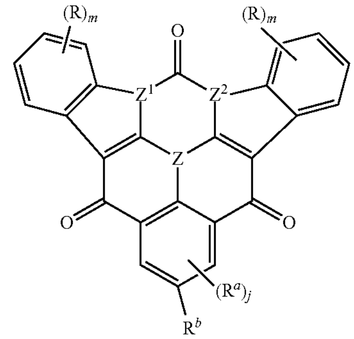
Formula (VII-14)
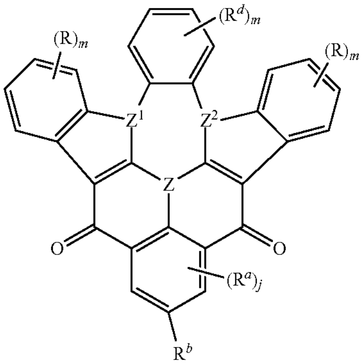
Formula (VII-15)
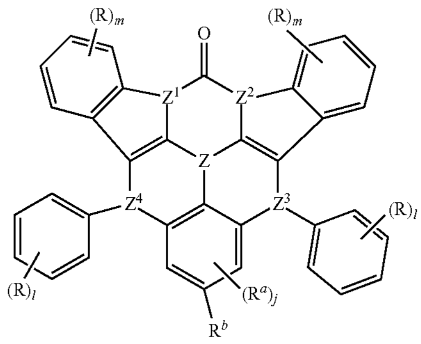
Formula (VII-16)
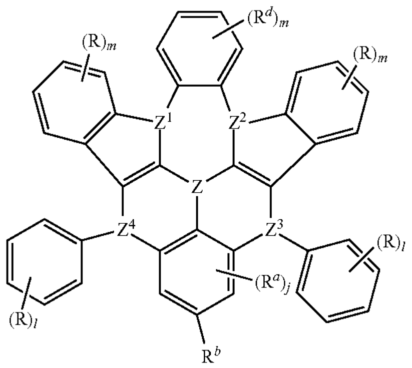

-continued

Formula (VII-17)

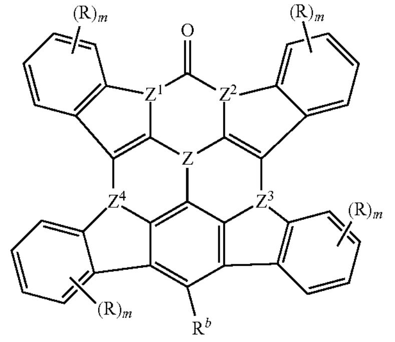

Formula (VII-18)

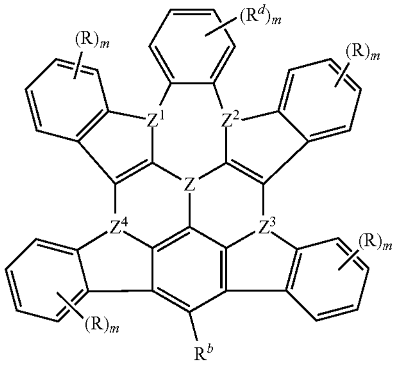

where Z, R, $R^a$, $R^b$, $R^c$ and $R^d$ have the definitions given above, especially for formula (I), and the further symbols have the following definition:

$Z^1$, $Z^2$, $Z^3$, $Z^4$ is the same or different at each instance and is N, B or Al, preferably N or B;

l is 0, 1, 2, 3, 4 or 5, preferably 0, 1 or 2;

m is 0, 1, 2, 3 or 4, preferably 0, 1 or 2;

j is 0, 1 or 2, preferably 0 or 1;

k is 0 or 1.

In structures of the formulae (VII-1) to (VII-18), it may be the case that the sum total of the indices j, k, l and m is preferably not more than 8, especially preferably not more than 6 and more preferably not more than 4.

In addition, in formulae (VII-1) to (VII-18) and/or the preferred embodiments of these formulae detailed below, inter alia, it may be the case that at least one, preferably two, of the $Z^1$ and $Z^2$ groups is/are N and at least one, preferably two, of the $Z^3$ and $Z^4$ groups is/are B or Al, preferably B. Configurations in which at least one, preferably two, of the $Z^1$ and $Z^2$ groups is/are N and at least one, preferably two, of the $Z^3$ and $Z^4$ groups is/are B or Al, preferably B, may advantageously be used as emitter.

Moreover, in formulae (VII-1) to (VII-18) and/or the preferred embodiments of these formulae detailed below, inter alia, it may be the case that at least one, preferably two, of the $Z^1$ and $Z^2$ groups is/are N and at least one, preferably two, of the $Z^3$ and $Z^4$ groups is/are N. Embodiments in which many, preferably all, of the $Z^1$, $Z^2$, $Z^3$, $Z^4$ groups are N may advantageously be used especially as hole conductor material.

In a further configuration, in formulae (VII-1) to (VII-18) and/or the preferred embodiments of these formulae detailed below, inter alia, it may be the case that at least one, preferably two, of the $Z^1$ and $Z^2$ groups is/are B or Al, preferably B, and at least one, preferably two, of the $Z^3$ and $Z^4$ groups is/are N. Configurations in which at least one, preferably two, of the $Z^1$ and $Z^2$ groups is/are B or Al, preferably B, and at least one, preferably two, of the $Z^3$ and $Z^4$ groups is/are N may advantageously be used as emitter.

In a further configuration, in formulae (VII-1) to (VII-18) and/or the preferred embodiments of these formulae detailed below, inter alia, it may be the case that at least one, preferably two, of the $Z^1$ and $Z^2$ groups is/are B or Al, preferably B or Al, preferably B, and at least one, preferably two, of the $Z^3$ and $Z^4$ groups is/are B or Al, preferably B.

Embodiments in which many, preferably all, of the $Z^1$, $Z^2$, $Z^3$, $Z^4$ groups are B or Al, preferably B, may advantageously be used especially as electron transport material.

Embodiments in which, depending on the structure, many, preferably all, of the Z, $Z^1$, $Z^2$, $Z^3$, $Z^4$ groups is/are N and many, preferably all, of the $Y^1$, $Y^2$, $Y^3$, $Y^4$ groups is/are N(Ar), N(R), P(Ar), P(R), O, S or Se may advantageously be used especially as hole conductor material.

Embodiments in which Z is B and, depending on the structure, many, preferably all, of the $Z^1$, $Z^2$, $Z^3$, $Z^4$ groups is/are B or Al, preferably B, and many, preferably all, of the $Y^1$, $Y^2$, $Y^3$, $Y^4$ is/are B(Ar), B(R), Al(Ar), Al(R), Ga(Ar), Ga(R), P(=O)Ar, P(=O)R, C=O, S=O or $SO_2$, preferably B(Ar), B(R), P(=O)Ar, P(=O)R, C=O, S=O or $SO_2$, more preferably C=O, B(R) or B(Ar), may advantageously be used especially as hole-conducting material.

In a preferred development of the present invention, it may be the case that at least two R, $R^a$, $R^b$, $R^c$, $R^d$ radicals together with the further groups to which the two R, $R^a$, $R^b$, $R^c$, $R^d$ radicals bind form a fused ring, where the two R, $R^a$, $R^b$, $R^c$, $R^d$ radicals form at least one structure of the formulae (RA-1) to (RA-12):

Formula RA-1

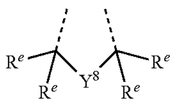

Formula RA-2

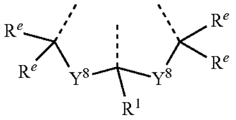

Formula RA-3

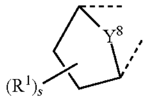

Formula RA-4

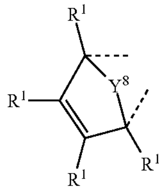

Formula RA-5

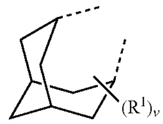

Formula RA-6

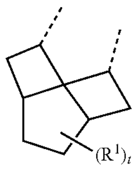

-continued

Formula RA-7

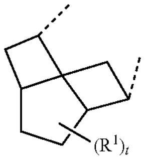

Formula RA-8

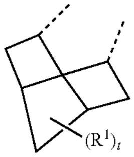

Formula RA-9

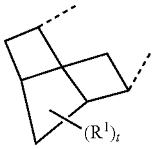

Formula RA-10

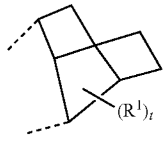

Formula RA-11

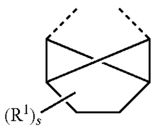

Formula RA-12

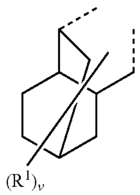

where $R^1$ has the definition set out above, the dotted bonds represent the sites of attachment via which the two R, $R^a$, $R^b$, $R^c$, $R^d$ radicals bind, and the further symbols have the following definition:

$Y^8$ is the same or different at each instance and is $C(R^1)_2$, $(R^1)_2C—C(R^1)_2$, $(R^1)C{=}C(R^1)$, $NR^1$, NAr', O or S, preferably $C(R^1)_2$, $(R^1)_2C—C(R^1)_2$, $(R^1)C{=}C(R^1)$, O or S;

$R^e$ is the same or different at each instance and is F, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^2$ radicals, where one or more adjacent $CH_2$ groups may be replaced by $R^2C{=}CR^2$, C≡C, $Si(R^2)_2$, C═O, C═S, C═Se, $C{=}NR^2$, —C(═O)O—, $—C({=}O)NR^2—$, $NR^2$, $P({=}O)(R^1)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; at the same time, two $R^e$ radicals or one $R^e$ radical with an $R^1$ radical or with a further group, may also form a ring system; where $R^1$ and $R^2$ have the definitions given above, especially for formula (I).

s is 0, 1, 2, 3, 4, 5 or 6, preferably 0, 1, 2, 3 or 4, more preferably 0, 1 or 2;

t is 0, 1, 2, 3, 4, 5, 6, 7 or 8, preferably 0, 1, 2, 3 or 4, more preferably 0, 1 or 2;

v is 0, 1, 2, 3, 4, 5, 6, 7, 8 or 9, preferably 0, 1, 2, 3 or 4, more preferably 0, 1 or 2.

In a preferred embodiment of the invention, the at least two R, $R^a$, $R^b$, $R^c$, $R^d$ radicals together with the further groups to which the two R, $R^a$, $R^b$, $R^c$, $R^d$ radicals bind form a fused ring, where the two R, $R^a$, $R^b$, $R^c$, $R^d$ radicals preferably form at least one of the structures of the formulae (RA-1a) to (RA-4f):

Formula RA-1a

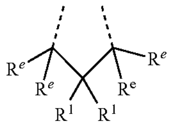

Formula RA-1b

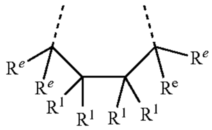

Formula RA-1c

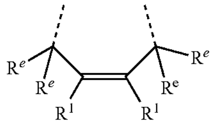

Formula RA-2a

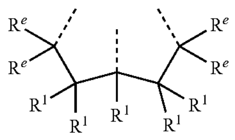

Formula RA-2b

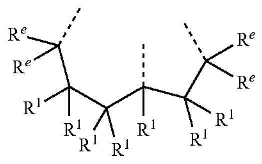

Formula RA-2c

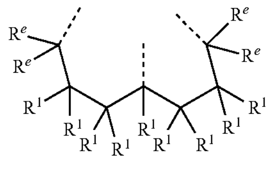

Formula RA-3a

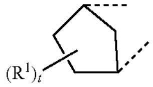

Formula RA-3b

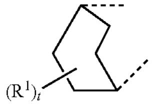

Formula RA-4a

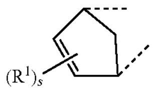

-continued

Formula RA-4b

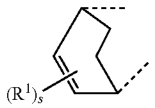

Formula RA-4c

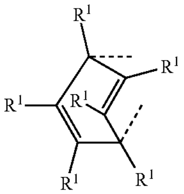

Formula RA-4d

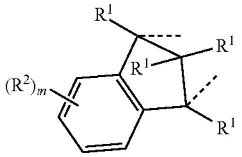

Formula RA-4e

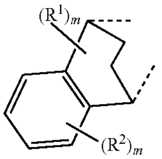

Formula RA-4f

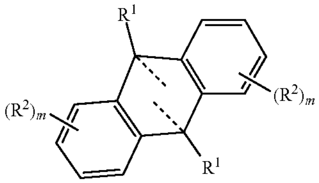

where the dotted bonds represent the sites of attachment via which the two R, $R^a$, $R^b$, $R^c$, $R^d$ radicals bind, the index m is 0, 1, 2, 3 or 4, preferably 0, 1 or 2, and the symbols $R^1$, $R^2$, $R^e$ and indices s and t have the definition given above, especially for formula (I) and/or formulae (RA-1) to (RA-12).

It may further be the case that the at least two R, $R^a$, $R^b$, $R^c$, $R^d$ radicals that form the structures of the formulae (RA-1) to (RA-12) and/or (RA-1a) to (RA-4f) and form a fused ring represent R, $R^a$, $R^b$, $R^c$, $R^d$ radicals from adjacent X, $X^1$, $X^2$, $X^3$, $X^4$ groups, or represent R radicals that each bind to adjacent carbon atoms, where these carbon atoms are preferably bonded to one another via a bond.

In a further-preferred configuration, at least two R, $R^a$, $R^b$, $R^c$, $R^d$ radicals together with the further groups to which the two R, $R^a$, $R^b$, $R^c$, $R^d$ radicals bind form a fused ring, where the two R, $R^a$, $R^b$, $R^c$, $R^d$ radicals form structures of the formula (RB):

Formula RB

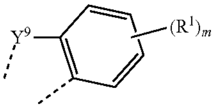

where $R^1$ has the definition given above, especially for formula (I), the dotted bonds represent the bonding sites via which the two R, $R^a$, $R^b$, $R^c$, $R^d$ radicals bind, the index m is 0, 1, 2, 3 or 4, preferably 0, 1 or 2, and $Y^9$ is $C(R^1)_2$, $NR^1$, NAr, $BR^1$, BAr, O or S, preferably $C(R^1)_2$, NAr' or O.

It may be the case here that the at least two R, $R^a$, $R^b$, $R^c$, $R^d$ radicals that form the structures of the formula (RB) and form a fused ring represent R, $R^a$, $R^b$, $R^c$, $R^d$ radicals from adjacent X, $X^1$, $X^2$, $X^3$, $X^4$ groups, or represent R radicals that each bind to adjacent carbon atoms, where these carbon atoms are preferably connected to one another via a bond.

More preferably, the compounds comprise at least one structure of the formulae (VIII-1) to (VIII-21); more preferably, the compounds are selected from compounds of the formulae (VIII-1) to (VIII-21), where the compounds have at least one fused ring:

Formula (VIII-1)

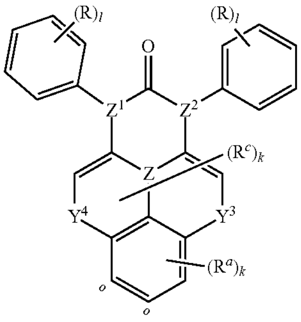

Formula (VIII-2)

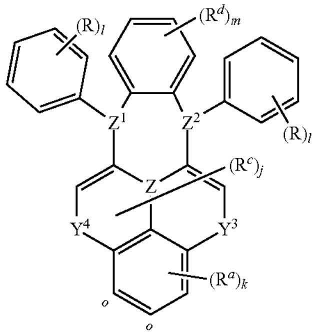

Formula (VIII-3)

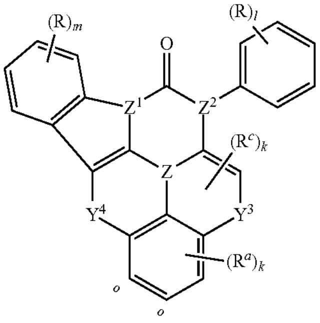

Formula (VIII-4)

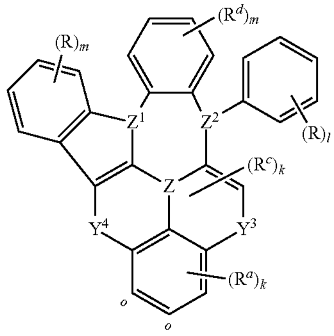

Formula (VIII-5)
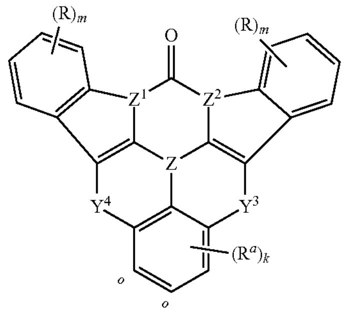
Formula (VIII-6)
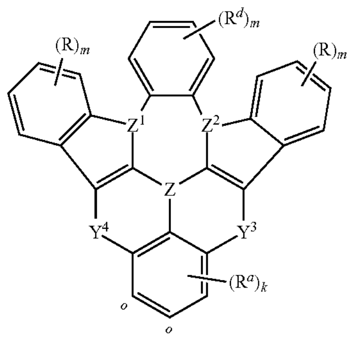
Formula (VIII-7)
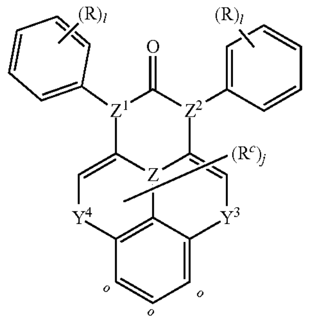
Formula (VIII-8)
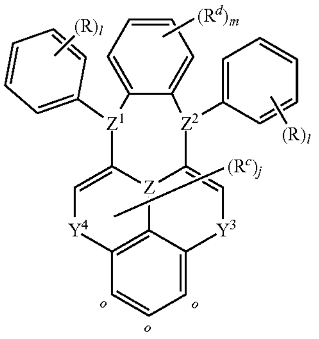
Formula (VIII-9)
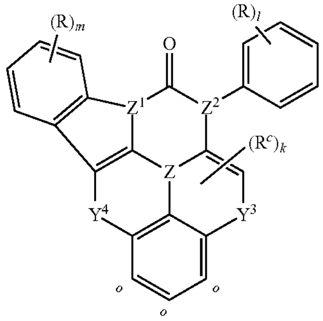
Formula (VIII-10)
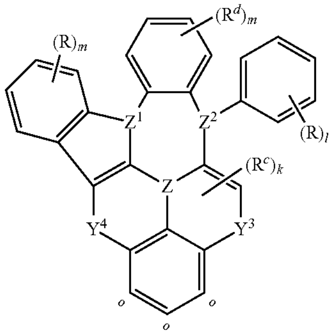
Formula (VIII-11)
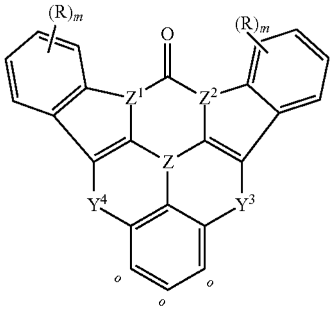
Formula (VIII-12)
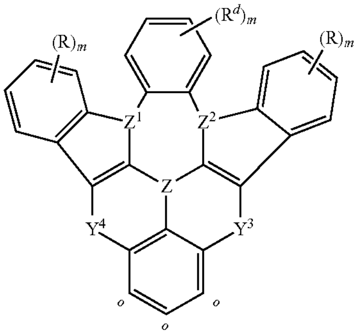

-continued
Formula (VIII-13)
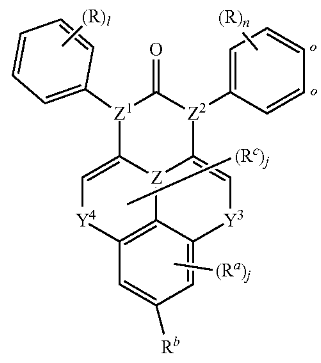
Formula (VIII-14)
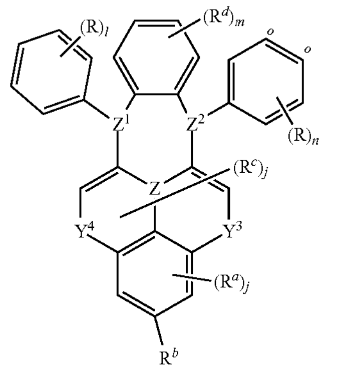
Formula (VIII-15)
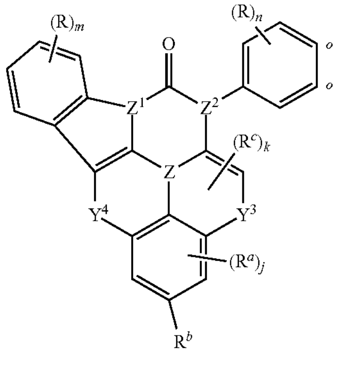
Formula (VIII-16)
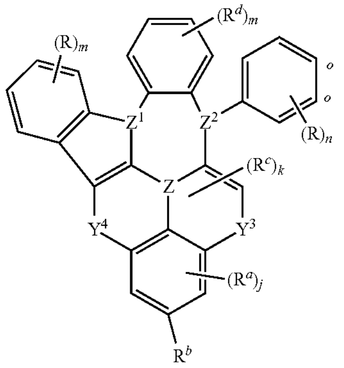
-continued
Formula (VIII-17)
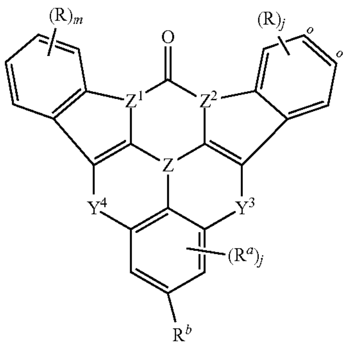
Formula (VIII-18)
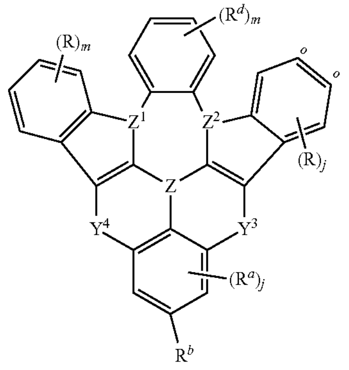
Formula (VIII-19)
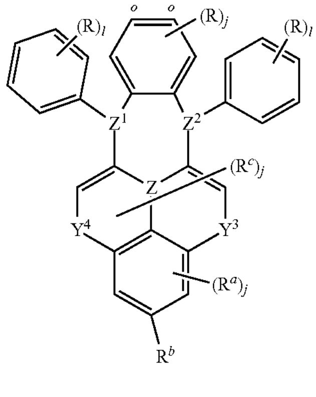
Formula (VIII-20)
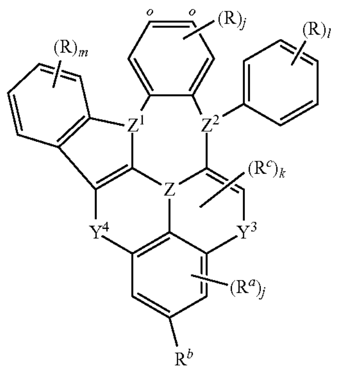

-continued

Formula (VIII-21)

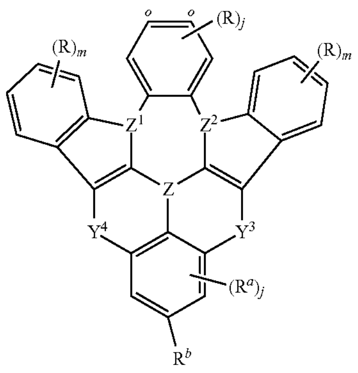

where the symbols $Y^3$, $Y^4$, Z, R, $R^a$, $R^b$, $R^c$ and $R^d$ have the definitions given above, especially for formula (I), the symbol o represents the attachment sites, and the further symbols have the following definition:

$Z^1$, $Z^2$ is the same or different at each instance and is N, B or Al, preferably N or B;

l is 0, 1, 2, 3, 4 or 5, preferably 0, 1 or 2;

m is 0, 1, 2, 3 or 4, preferably 0, 1 or 2;

n is 0, 1, 2 or 3, preferably 0, 1 or 2;

j is 0, 1 or 2, preferably 0 or 1;

k is 0 or 1.

Preferably, the fused ring, especially in formulae (VIII-1) to (VIII-21), is formed by at least two R, $R^a$, $R^b$, $R^c$, $R^d$ radicals and the further groups to which the two R, $R^a$, $R^b$, $R^c$, $R^d$ radicals bind, where the at least two R, $R^a$, $R^b$, $R^c$, $R^d$ radicals form structures of the formulae (RA-1) to (RA-12), (RA-1a) to (RA-4f) and/or of the formula (RB), preferably structures of the formulae (RA-1) to (RA-12) and/or (RA-1a) to (RA-4f).

It may preferably be the case that the compounds have at least two fused rings, wherein at least one fused ring is formed by structures of the formulae (RA-1) to (RA-12) and/or (RA-1a) to (RA-4f) and a further ring is formed by structures of the formulae (RA-1) to (RA-12), (RA-1a) to (RA-4f) or (RB), where the compounds comprise at least one structure of the formulae (IX-1) to (IX-21), preferably where the compounds are selected from the compounds of the formulae (IX-1) to (IX-21):

Formula (IX-1)

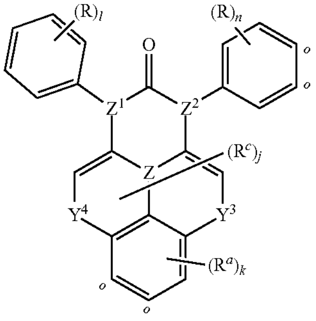

-continued

Formula (IX-2)

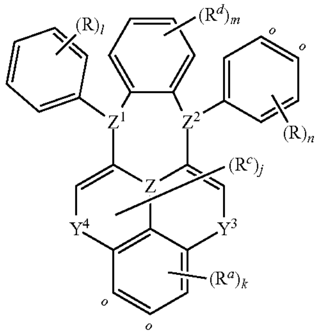

Formula (IX-3)

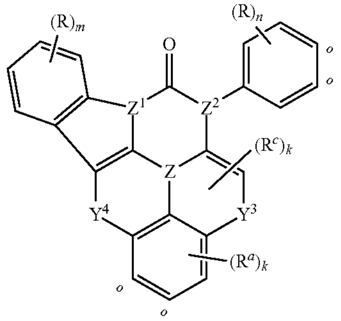

Formula (IX-4)

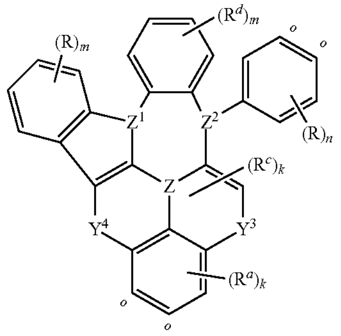

Formula (IX-5)

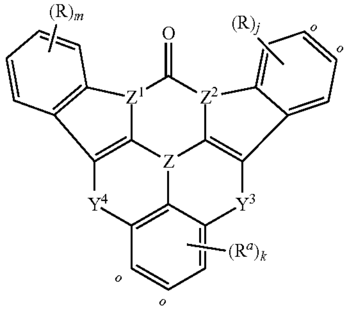

-continued
Formula (IX-6)
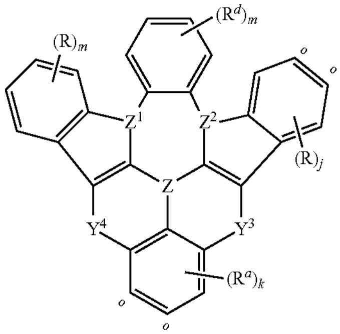
Formula (IX-7)
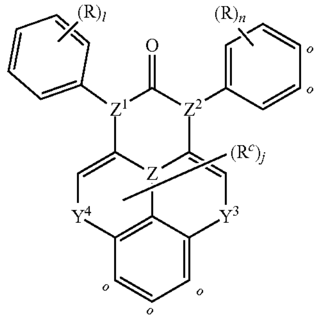
Formula (IX-8)
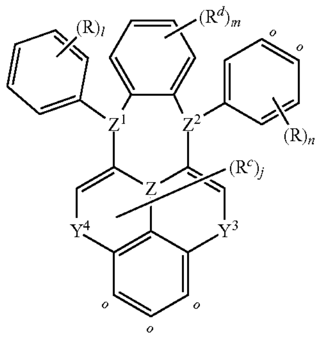
Formula (IX-9)
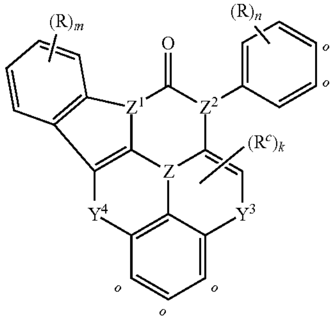
-continued
Formula (IX-10)
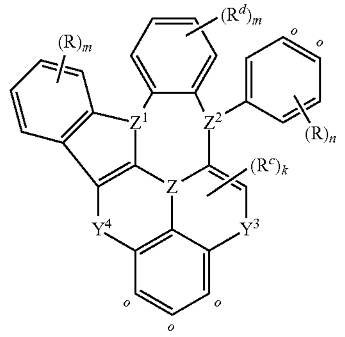
Formula (IX-11)
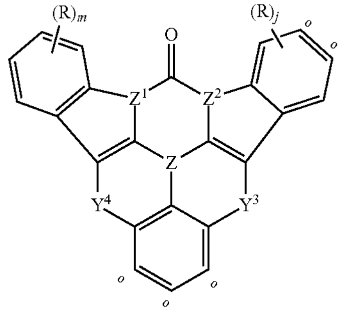
Formula (IX-12)
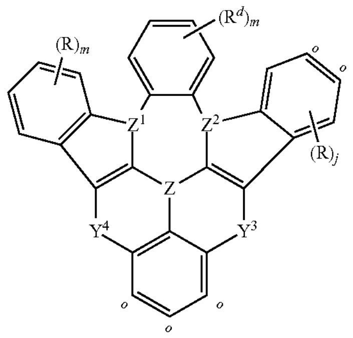
Formula (IX-13)
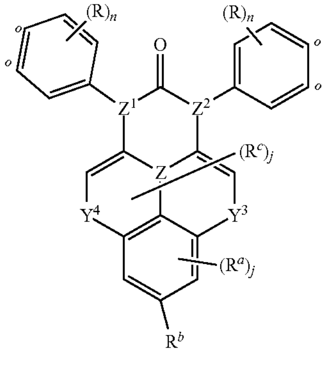

-continued
Formula (IX-14)
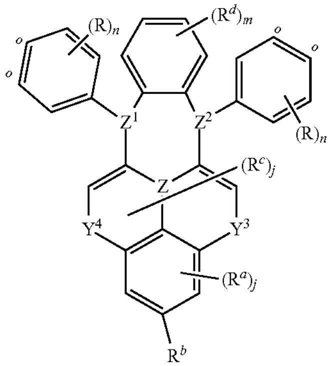
Formula (IX-15)
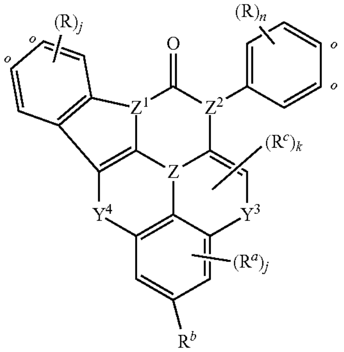
Formula (IX-16)
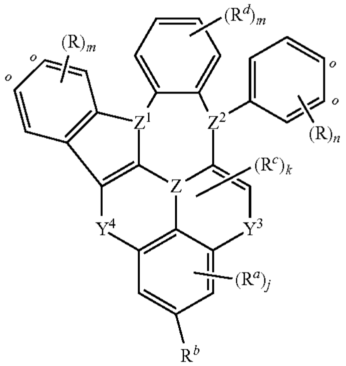
Formula (IX-17)
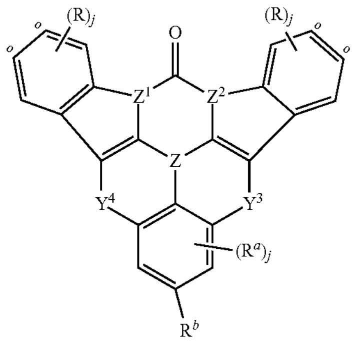
-continued
Formula (IX-18)
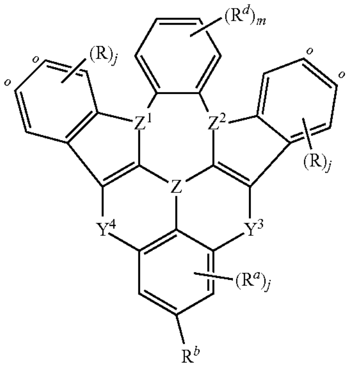
Formula (IX-19)
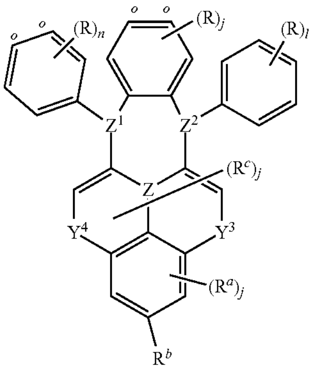
Formula (IX-20)
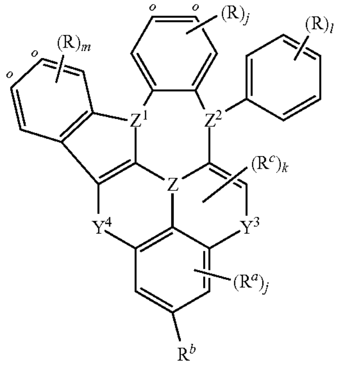
Formula (IX-21)
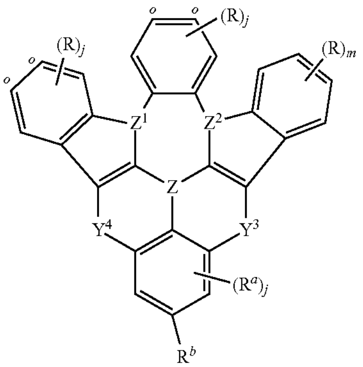
where the symbols $Y^3$, $Y^4$, Z, R, $R^a$, $R^b$, $R^c$ and $R^d$ have the definitions given above, especially for formula (I), the symbol o represents the attachment sites, and the further symbols have the following definition:

$Z^1$, $Z^2$ is the same or different at each instance and is N, B or Al, preferably N or B;

l is 0, 1, 2, 3, 4 or 5, preferably 0, 1 or 2;

m is 0, 1, 2, 3 or 4, preferably 0, 1 or 2;

n is 0, 1, 2 or 3, preferably 0, 1 or 2;

j is 0, 1 or 2, preferably 0 or 1; and k is 0 or 1.

Especially in the formulae (VIII-1) to (VIII-21) and/or (IX-1) to (IX-21), the sum total of the indices k, j, l, m and n is 0, 1, 2 or 3, preferably 0, 1 or 2.

It may be the case here that the formulae (IX-1) to (IX-21) have at least two fused rings, where the fused rings are the same and the moiety formed by two R, $R^a$, $R^b$, $R^c$, $R^d$ radicals can be represented by at least one structure of the formulae (RA-1) to (RA-12) and/or (RA-1a) to (RA-4f).

It may further be the case that the formulae (IX-1) to (IX-21) have at least two fused rings, where the fused rings are different and the moiety formed by two R, $R^a$, $R^b$, $R^c$, $R^d$ radicals can be represented in each case by at least one structure of the formulae (RA-1) to (RA-12) and/or (RA-1a) to (RA-4f).

It may additionally be the case that the formulae (IX-1) to (IX-21) have at least two fused rings, where the fused rings are different and one of the two fused rings has a moiety formed by two R, $R^a$, $R^b$, $R^c$, $R^d$ radicals that can be represented by at least one of the structures of the formulae (RA-1) to (RA-12) and/or (RA-1a) to (RA-4f), and one of the two fused rings has a moiety formed by two R, $R^a$, $R^b$, $R^c$, $R^d$ radicals that can be represented by one of the structures of the formula (RB).

It may additionally be the case that the substituents R, $R^a$, $R^b$, $R^c$, $R^d$ and $R^e$, $R^1$ and $R^2$ according to the above formulae do not form a fused aromatic or heteroaromatic ring system with the ring atoms of the ring system to which the substituents R, $R^a$, $R^b$, $R^c$, $R^d$, $R^e$, $R^1$ and $R^2$ bind.

This includes the formation of a fused aromatic or heteroaromatic ring system with possible substituents $R^1$ and $R^2$ that may be bonded to the R, $R^a$, $R^b$, $R^c$, $R^d$, $R^e$ and $R^1$ radicals.

When two radicals that may especially be selected from R, $R^a$, $R^b$, $R^c$, $R^d$, $R^e$, $R^1$ and/or $R^2$ form a ring system with one another, this ring system may be mono- or polycyclic, aliphatic, heteroaliphatic, aromatic or heteroaromatic. In this case, the radicals which together form a ring system may be adjacent, meaning that these radicals are bonded to the same carbon atom or to carbon atoms directly bonded to one another, or they may be further removed from one another. In addition, the ring systems provided with the substituents R, $R^a$, $R^b$, $R^c$, $R^d$, $R^e$, $R^1$ and/or $R^2$ may also be joined to one another via a bond, such that this can bring about a ring closure. In this case, each of the corresponding bonding sites has preferably been provided with a substituent R, $R^a$, $R^b$, $R^c$, $R^d$, $R^e$, $R^1$ and/or $R^2$.

In a preferred configuration, a compound of the invention can be represented by at least one of the structures of formulae (I), (II), (IIIa) to (IIIk), (IVa) to (IVn), (Va) to (Vk), (VI-1) to (VI-39), (VII-1) to (VII-18), (VIII-1) to (VIII-21) and/or (IX-1) to (IX-21). Preferably, compounds of the invention, preferably comprising structures of formulae (I), (II), (IIIa) to (IIIk), (IVa) to (IVn), (Va) to (Vk), (VI-1) to (VI-39), (VII-1) to (VII-18), (VIII-1) to (VIII-21) and/or (IX-1) to (IX-21) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

Preferred aromatic or heteroaromatic ring systems R, $R^a$, $R^b$, $R^c$, $R^d$, Ar' and/or Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3, 4 or 9 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ or R radicals.

It may preferably the case that at least one substituent R, $R^a$, $R^b$, $R^c$, $R^d$ is the same or different at each instance and is selected from the group consisting of H, D, a branched or cyclic alkyl, alkoxy or thioalkoxy group having 3 to 20 carbon atoms or an aromatic or heteroaromatic ring system selected from the groups of the following formulae Ar-1 to Ar-75, where the substituents R, $R^a$, $R^b$, $R^c$, $R^d$ preferably either form a ring according to the structures of the formulae (RA-1) to (RA-12), (RA-1a) to (RA-4f) or (RB), or the substituent R, $R^a$, $R^b$, $R^c$, $R^d$ is the same or different at each instance and is selected from the group consisting of H, D or an aromatic heteroaromatic ring system selected from the groups of the following formulae Ar-1 to Ar-75, and/or the Ar' group is the same or different at each instance and is selected from the groups of the following formulae Ar-1 to Ar-75:

Ar-1

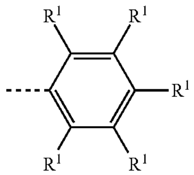

Ar-2

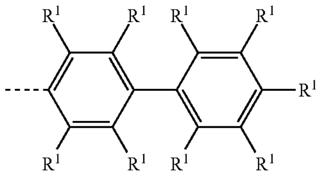

Ar-3

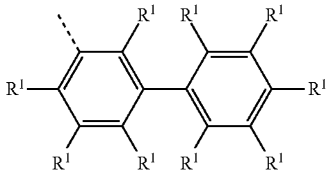

Ar-4

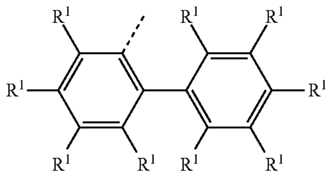

-continued
Ar-5
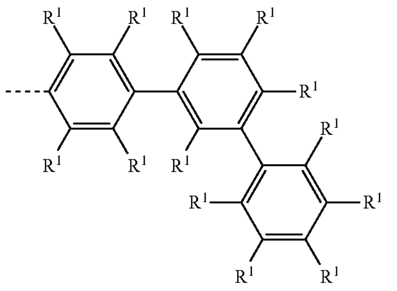
Ar-6
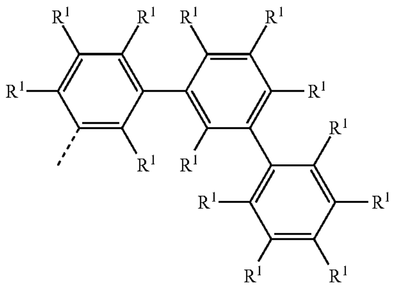
Ar-7
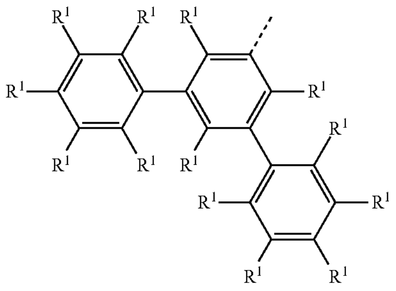
Ar-8
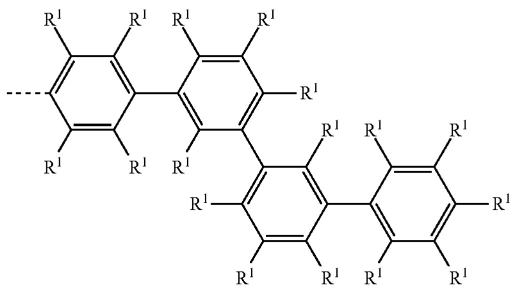
Ar-9
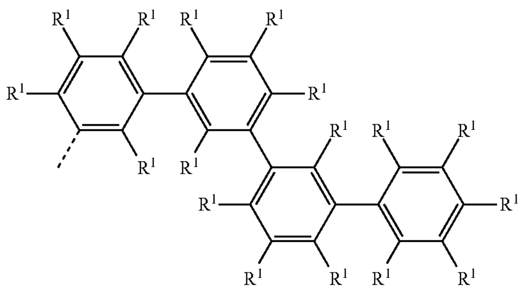
-continued
Ar-10
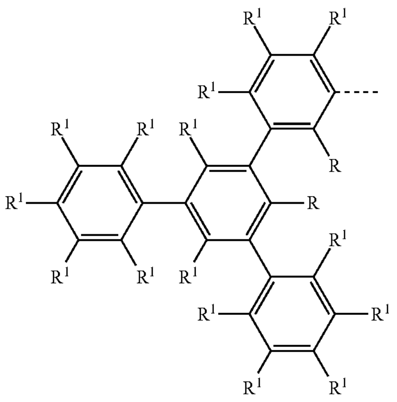
Ar-11
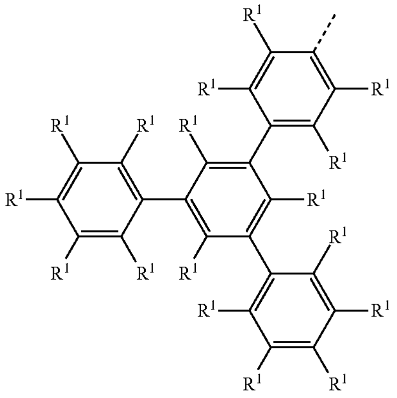
Ar-12
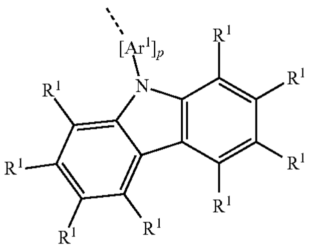
Ar-13
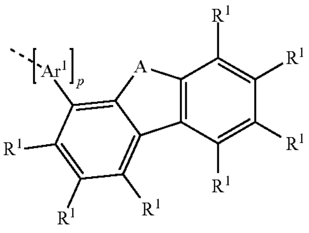
Ar-14
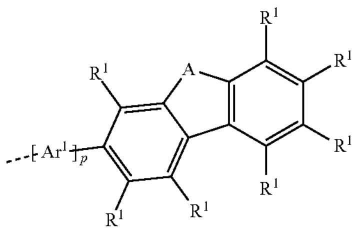

-continued
Ar-15
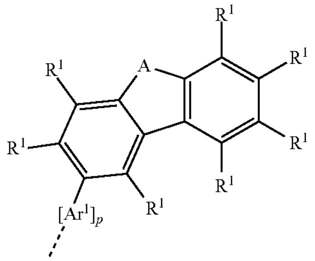
Ar-16
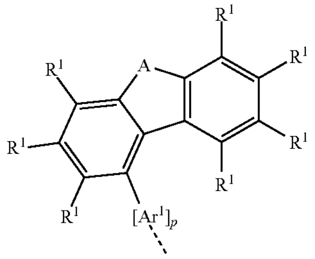
Ar-17
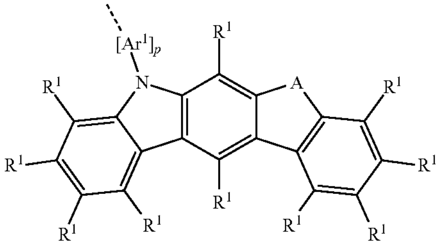
Ar-18
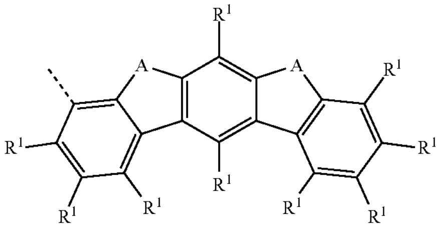
Ar-19
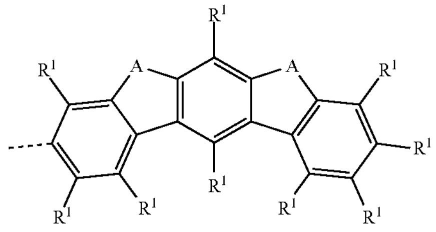
Ar-20
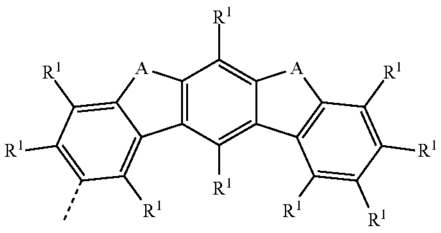
-continued
Ar-21
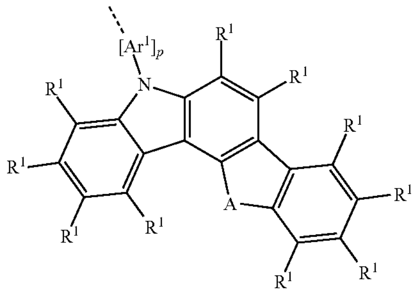
Ar-22
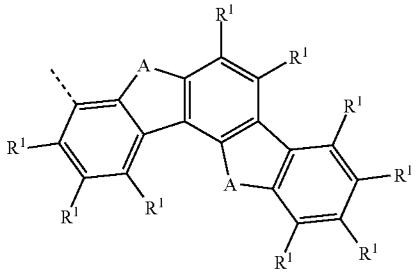
Ar-23
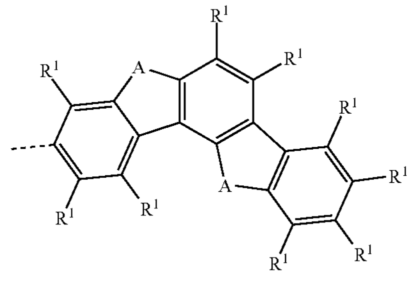
Ar-24
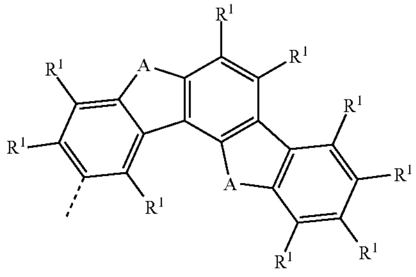
Ar-25
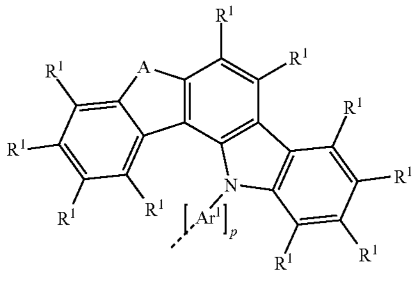

-continued
Ar-26
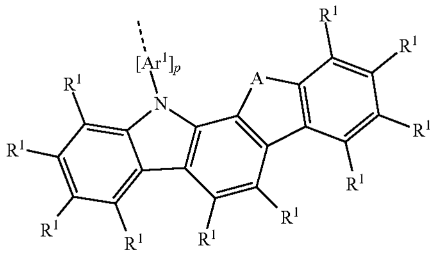
Ar-27
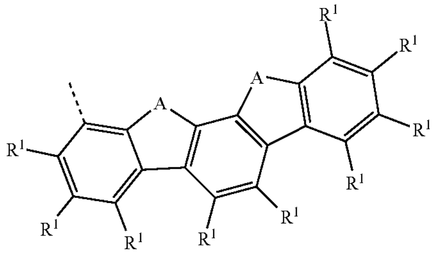
Ar-28
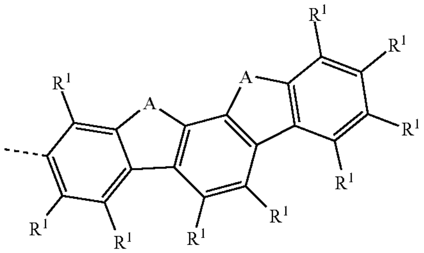
Ar-29
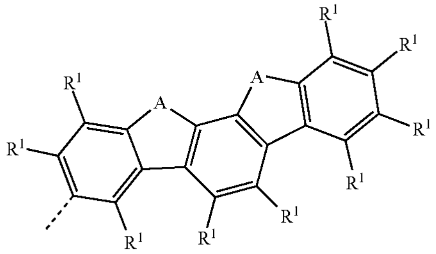
Ar-30
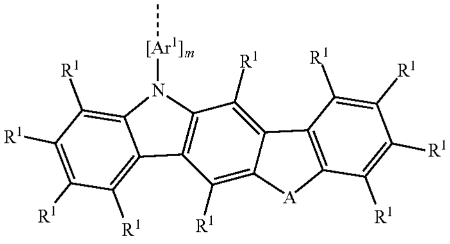
Ar-31
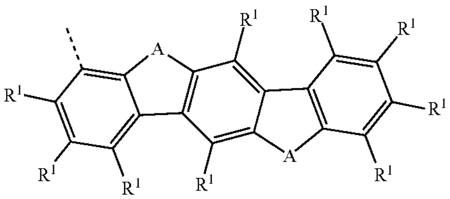
-continued
Ar-32
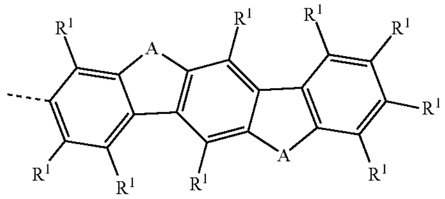
Ar-33
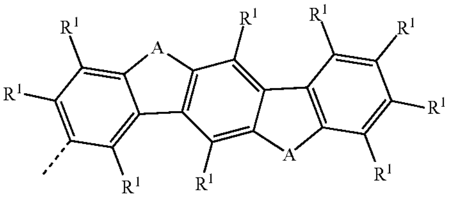
Ar-34
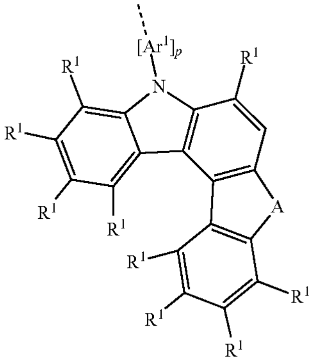
Ar-35
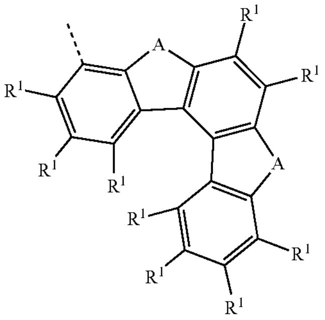
Ar-36
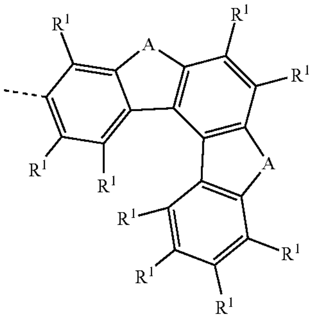

-continued
Ar-37
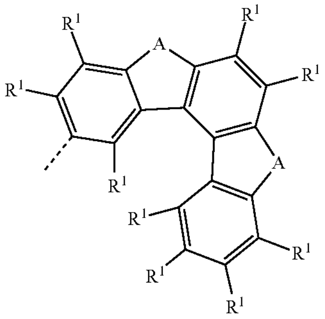
Ar-38
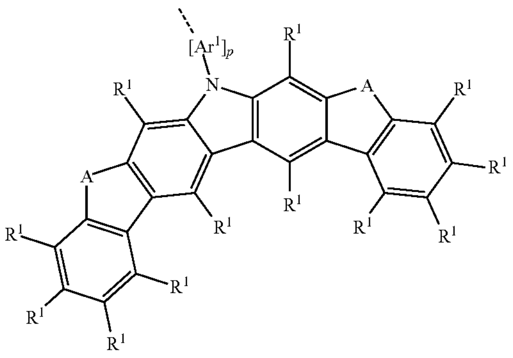
Ar-39
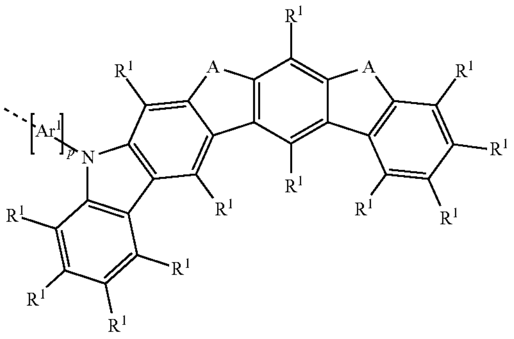
Ar-40
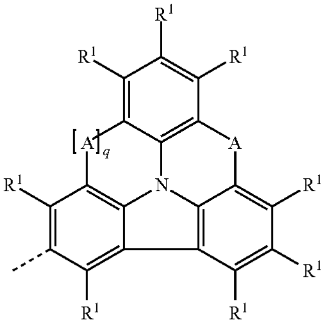
-continued
Ar-41
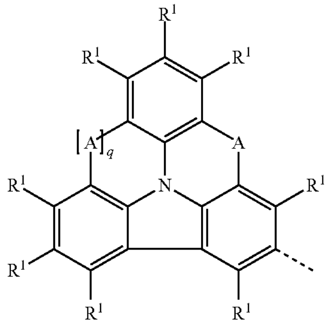
Ar-42
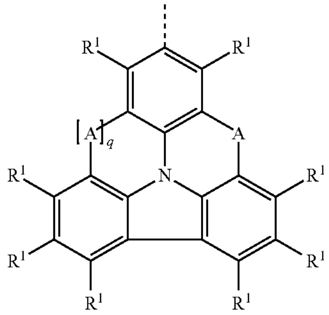
Ar-43
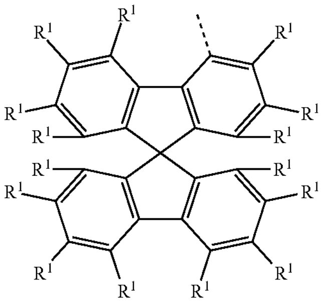
Ar-44
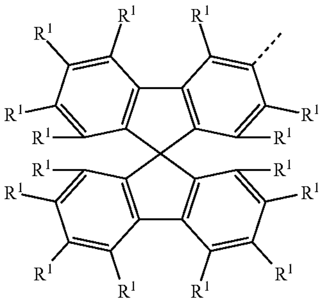
Ar-45
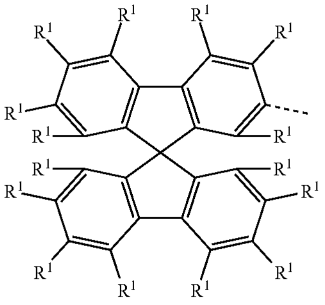

-continued
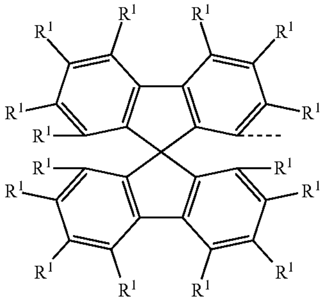
Ar-46
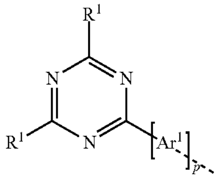
Ar-47
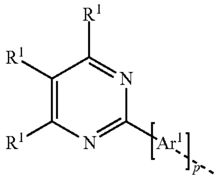
Ar-48
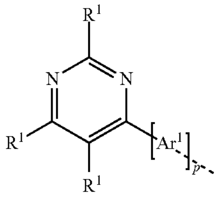
Ar-49
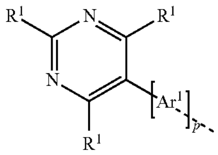
Ar-50
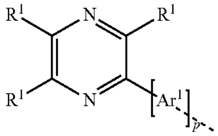
Ar-51
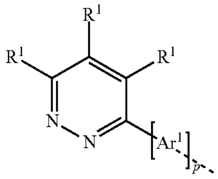
Ar-52
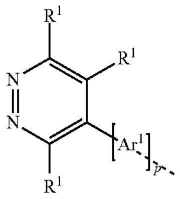
Ar-53
-continued
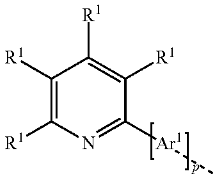
Ar-54
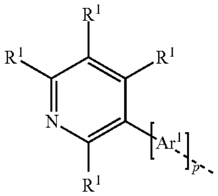
Ar-55
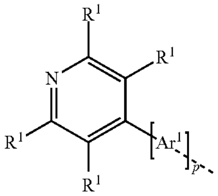
Ar-56
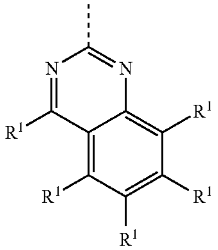
Ar-57
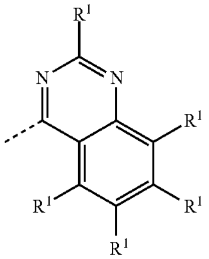
Ar-58
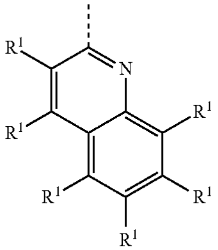
Ar-59

-continued
Ar-60
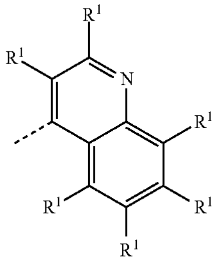
Ar-61
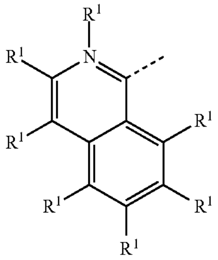
Ar-62
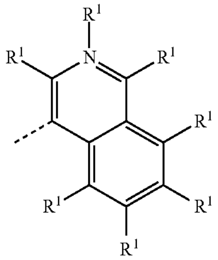
Ar-63
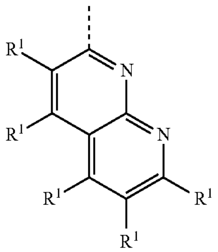
Ar-64
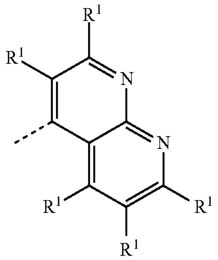
Ar-65
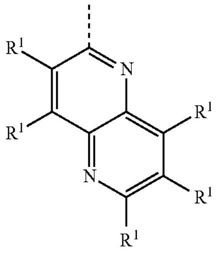
-continued
Ar-66
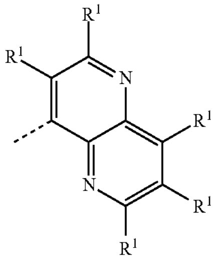
Ar-67
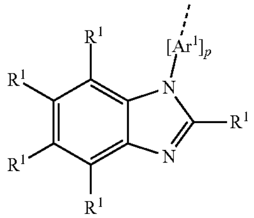
Ar-68
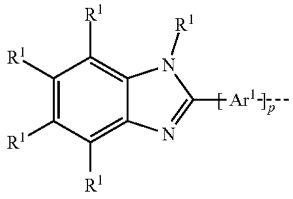
Ar-69
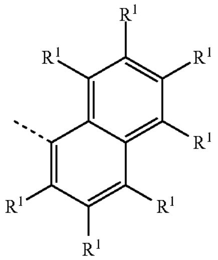
Ar-70
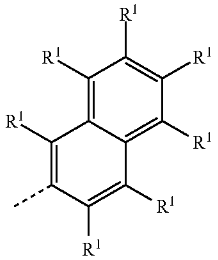
Ar-71
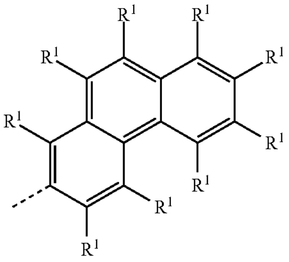

-continued

Ar-72

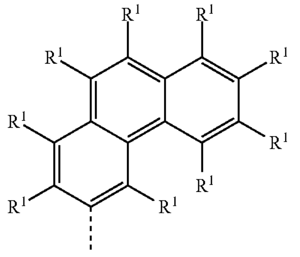

Ar-73

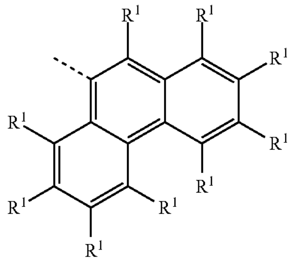

Ar-74

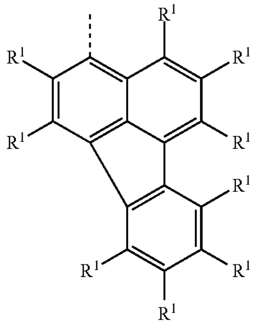

Ar-75

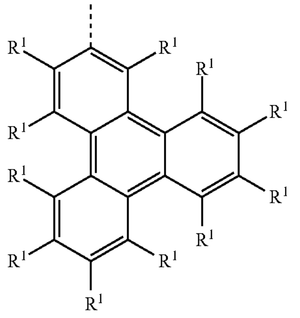

where $R^1$ is as defined above, the dotted bond represents the attachment site and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to the corresponding radical;

q is 0 or 1, where q=0 means that no A group is bonded at this position and $R^1$ radicals are bonded to the corresponding carbon atoms instead.

When the abovementioned groups for Ar have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Preference is given to phenyl, biphenyl, terphenyl and quaterphenyl having bonding patterns as listed above for Ar-1 to Ar-11, where these structures, rather than by $R^1$, may be substituted by one or more $R^2$ radicals, but are preferably unsubstituted. Preference is further given to triazine, pyrimidine and quinazoline as listed above for Ar-47 to Ar-50, Ar-57 and Ar-58, where these structures, rather than by $R^1$, may be substituted by one or more $R^2$ radicals.

There follows a description of preferred substituents R, $R^a$, $R^b$, $R^c$, $R^d$ and $R^e$.

In a preferred embodiment of the invention, R, $R^a$, $R^b$, $R^c$, $R^d$ are the same or different at each instance and are selected from the group consisting of H, D, F, CN, $NO_2$, $Si(R^1)_3$, $B(OR^1)_2$, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

In a further-preferred embodiment of the invention, substituent R, $R^a$, $R^b$, $R^c$, $R^d$ is the same or different at each instance and is selected from the group consisting of H, D, F, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

It may further be the case that at least one substituent R, $R^a$, $R^b$, $R^c$, $R^d$ is the same or different at each instance and is selected from the group consisting of H, D, an aromatic or heteroaromatic ring system which has 6 to 30 aromatic ring atoms and may be substituted by one or more $R^1$ radicals, and an $N(Ar')_2$ group. In a further-preferred embodiment of the invention, the substituents R, $R^a$, $R^b$, $R^c$, $R^d$ either form a ring according to the structures of the formulae (RA-1) to (RA-12), (RA-1a) to (RA-4f) or (RB), or R, $R^a$, $R^b$, $R^c$, $R^d$ is the same or different at each instance and is selected from the group consisting of H, D, an aromatic heteroaromatic ring system which has 6 to 30 aromatic ring atoms and may be substituted by one or more $R^1$ radicals, or an $N(Ar')_2$ group. More preferably, substituent R, $R^a$, $R^b$, $R^c$, $R^d$ is the same or different at each instance and is selected from the group consisting of H or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more $R^1$ radicals.

In a preferred embodiment of the invention, $R^e$ is the same or different at each instance and is selected from the group consisting of a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^2$ radicals.

In a further-preferred embodiment of the invention, $R^e$ is the same or different at each instance and are selected from the group consisting of a straight-chain alkyl group having 1 to 10 carbon atoms or a branched or cyclic alkyl group having 3 to 10 carbon atoms, where the alkyl group may be substituted in each case by one or more $R^1$ radicals, an aromatic or heteroaromatic ring system which has 6 to 30 aromatic ring atoms and may be substituted by one or more $R^2$ radicals. More preferably, $R^e$ is the same or different at each instance and are selected from the group consisting of a straight-chain alkyl group having 1 to 5 carbon atoms or a branched or cyclic alkyl group having 3 to 5 carbon atoms, where the alkyl group may be substituted in each case by one or more $R^2$ radicals, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^2$ radicals.

In a preferred embodiment of the invention, $R^e$ is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals; at the same time, two $R^e$ radicals together may also form a ring system. More preferably, $R^e$ is the same or different at each instance and is selected from the group consisting of a straight-chain alkyl group having 1, 2, 3 or 4 carbon atoms or a branched or cyclic alkyl group having 3 to 6 carbon atoms, where the alkyl group may be substituted in each case by one or more $R^2$ radicals, but is preferably unsubstituted, or an aromatic ring system which has 6 to 12 aromatic ring atoms, especially 6 aromatic ring atoms, and may be substituted in each case by one or more preferably nonaromatic $R^2$ radicals, but is preferably unsubstituted; at the same time, two $R^e$ radicals together may form a ring system. Most preferably, $R^e$ is the same or different at each instance and is selected from the group consisting of a straight-chain alkyl group having 1, 2, 3 or 4 carbon atoms, or a branched alkyl group having 3 to 6 carbon atoms. Most preferably, $R^e$ is a methyl group or is a phenyl group, where two phenyl groups together may form a ring system, preference being given to a methyl group over a phenyl group.

Preferred aromatic or heteroaromatic ring systems substituent R, $R^a$, $R^b$, $R^c$, $R^d$, $R^e$ or Ar or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more R, $R^1$ or $R^2$ radicals. The structures Ar-1 to Ar-75 listed above are particularly preferred, preference being given to structures of the formulae (Ar-1), (Ar-2), (Ar-3), (Ar-12), (Ar-13), (Ar-14), (Ar-15), (Ar-16), (Ar-69), (Ar-70), (Ar-75), and particular preference to structures of the formulae (Ar-1), (Ar-2), (Ar-3), (Ar-12), (Ar-13), (Ar-14), (Ar-15), (Ar-16). With regard to the structures Ar-1 to Ar-75, it should be stated that these are shown with a substituent $R^1$. In the case of the ring systems Ar, these substituents $R^1$ should be replaced by R, and in the case of $R^e$, these substituents $R^1$ should be replaced by $R^2$.

Further suitable R, $R^a$, $R^b$, $R^c$, $R^d$ groups are groups of the formula —$Ar^4$—$N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene or triphenylene, each of which may be substituted by one or more $R^1$ radicals. Most preferably, $Ar^2$ and $Ar^3$ are the same or different at each instance and are selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

In a further preferred embodiment of the invention, $R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 13 aromatic ring atoms and may be substituted in each case by one or more $R^5$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

At the same time, in compounds of the invention that are processed by vacuum evaporation, the alkyl groups preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

It may further be the case that the compound comprises exactly two or exactly three structures of formula (I), (II), (IIIa) to (IIIk), (IVa) to (IVn), (Va) to (Vk), (VI-1) to (VI-39), (VII-1) to (VII-18), (VIII-1) to (VIII-21) and/or (IX-1) to (IX-21), where preferably one of the aromatic heteroaromatic ring systems to which at least one of the $Y^1$, $Y^2$, $Y^3$, $Y^4$ groups binds is shared by the two structures.

In a preferred configuration, the compounds are selected from compounds of the formula (D-1) and (D-2):

Formula (D-1)

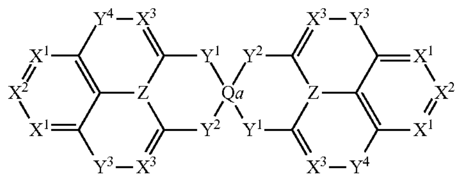

Formula (D-2)

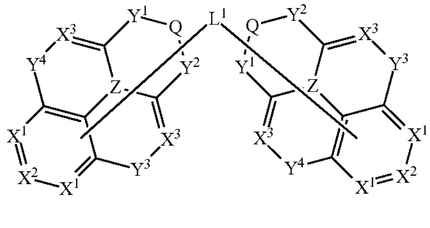

where the $Q^a$ group is an aromatic or heteroaromatic ring system which has 5 to 60 aromatic ring atoms and may be substituted in each case by one or more R radicals, the $L^1$ group represents a connecting group, preferably a bond or an aromatic or heteroaromatic ring system which has 5 to 40, preferably 5 to 30, aromatic ring atoms and may be substituted by one or more R radicals, and the further symbols and indices used have the definitions given above, especially for formula (I).

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $L^1$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (I).

Further preferably, the symbol $L^1$ shown in formula (D2) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the $L^1$ group shown in formula (D2) comprises an aromatic ring system having not more than two fused aromatic and/or heteroaromatic 6-membered rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^1$ radicals, but are preferably unsubstituted.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds shown in the following table:

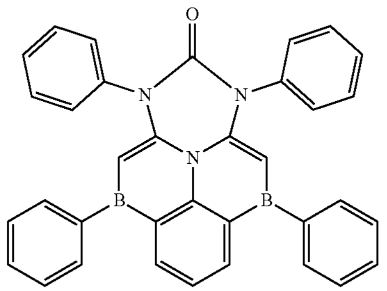 [SMILES: O=C1N(c2ccccc2)C2=CB(c3ccccc3)c3cccc4c3N2C(=CB4c2ccccc2)N1c1ccccc1]
1
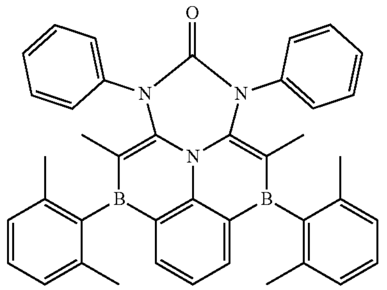 [SMILES: CC1=C2N(c3ccccc3)C(=O)N(c3ccccc3)C3=C(C)B(c4c(C)cccc4C)c4cccc(c4N23)B1c1c(C)cccc1C]
2
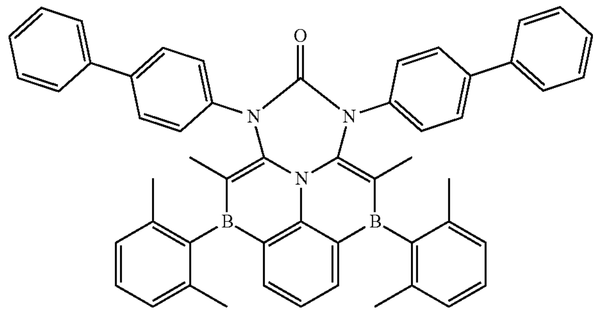 [SMILES: CC1=C2N(c3ccc(-c4ccccc4)cc3)C(=O)N(c3ccc(-c4ccccc4)cc3)C3=C(C)B(c4c(C)cccc4C)c4cccc(c4N23)B1c1c(C)cccc1C]
3
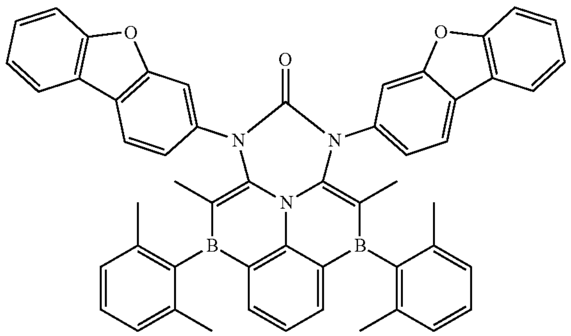 [SMILES: CC1=C2N(c3ccc4c(c3)oc3ccccc34)C(=O)N(c3ccc4c(c3)oc3ccccc34)C3=C(C)B(c4c(C)cccc4C)c4cccc(c4N23)B1c1c(C)cccc1C]
4
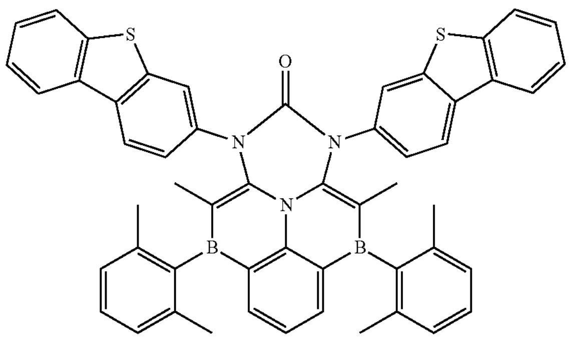 [SMILES: CC1=C2N(c3ccc4c(c3)sc3ccccc34)C(=O)N(c3ccc4c(c3)sc3ccccc34)C3=C(C)B(c4c(C)cccc4C)c4cccc(c4N23)B1c1c(C)cccc1C]
5

-continued
6
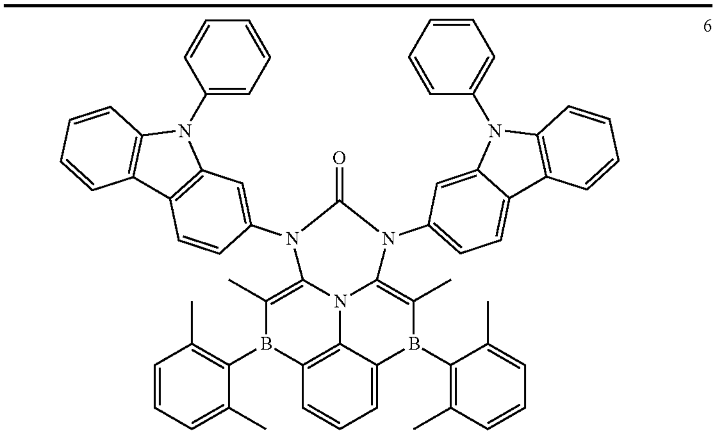
7
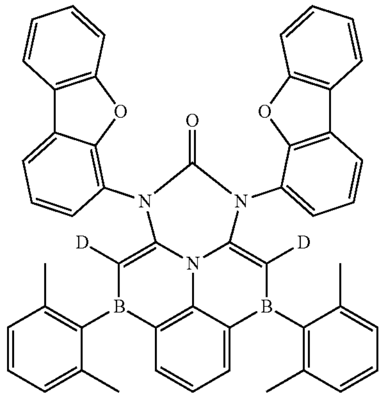 [SMILES: [2H]C1=C2N3C(=C([2H])B(c4c(C)cccc4C)c4cccc(c43)B1c1c(C)cccc1C)N(c1cccc3c1oc1ccccc13)C(=O)N2c1cccc2c1oc1ccccc12]
8
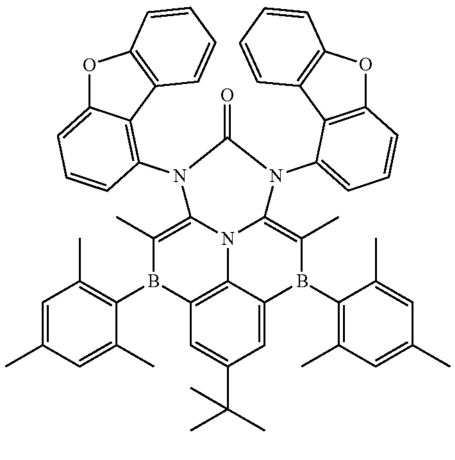

-continued
9
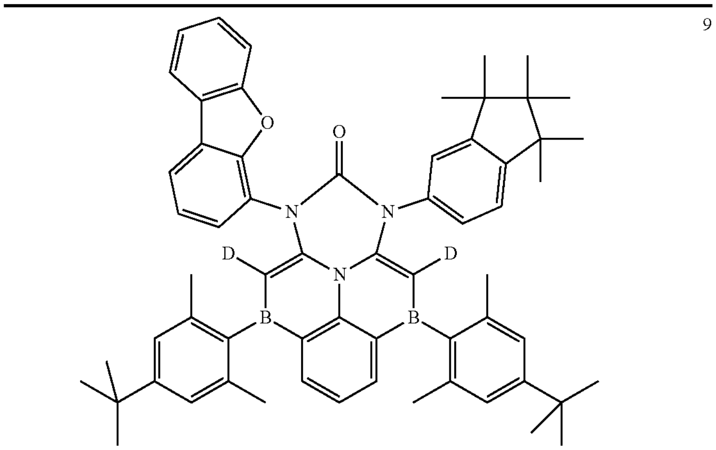
10
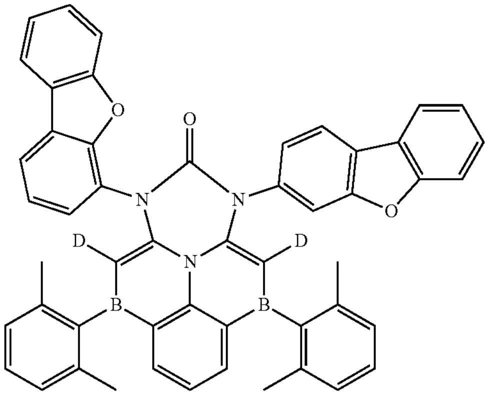 [SMILES: [2H]C1=C2N(c3ccc4c(c3)oc3ccccc34)C(=O)N(c3cccc4c3oc3ccccc34)C3=C([2H])B(c4c(C)cccc4C)c4cccc(c4N23)B1c1c(C)cccc1C]
11
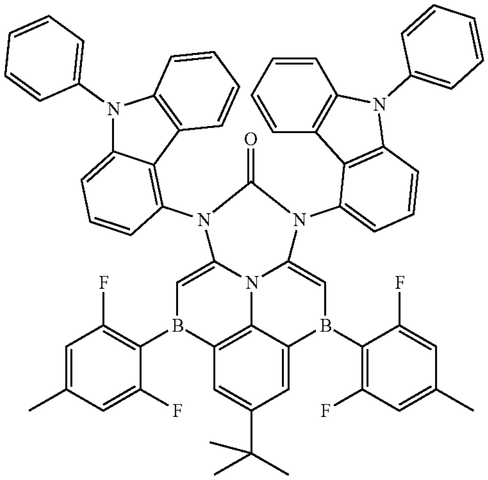 [SMILES: Cc1cc(F)c(B2C=C3N4C(=CB(c5c(F)cc(C)cc5F)c5cc(C(C)(C)C)cc2c54)N(c2cccc4c2c2ccccc2n4-c2ccccc2)C(=O)N3c2cccc3c2c2ccccc2n3-c2ccccc2)c(F)c1]

-continued
12
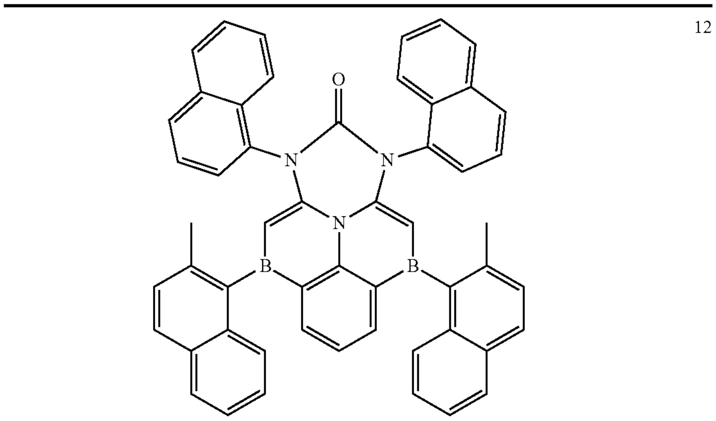
13
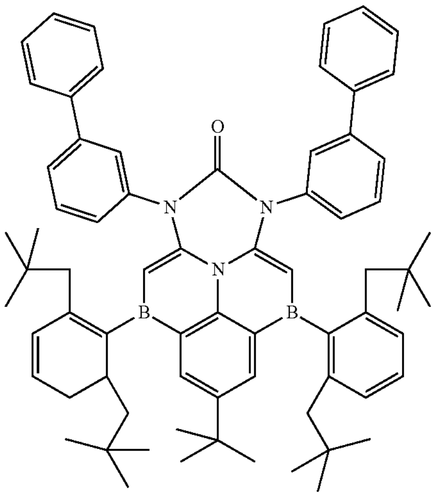 [SMILES: CC(C)(C)CC1=C(B2C=C3N(c4cccc(-c5ccccc5)c4)C(=O)N(c4cccc(-c5ccccc5)c4)C4=CB(c5c(CC(C)(C)C)cccc5CC(C)(C)C)c5cc(C(C)(C)C)cc2c5N34)C(CC(C)(C)C)CC=C1]
14
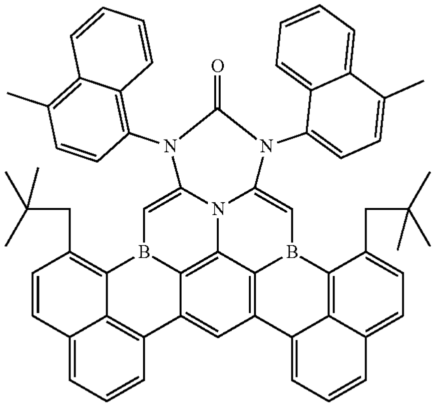 [SMILES: Cc1ccc(N2C(=O)N(c3ccc(C)c4ccccc34)C3=CB4c5c(cc6c7c5N3C2=CB7c2c(CC(C)(C)C)ccc3cccc-6c23)-c2cccc3ccc(CC(C)(C)C)c4c23)c2ccccc12]

-continued
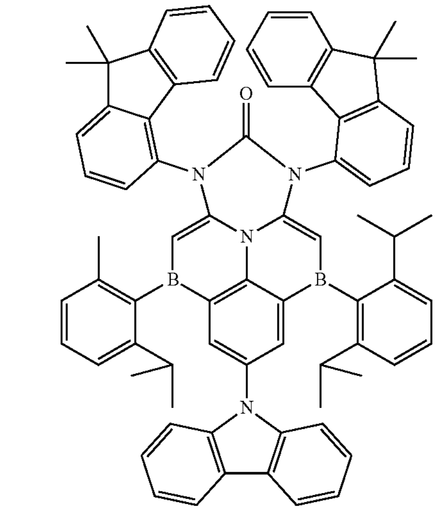 [SMILES: Cc1cccc(C(C)C)c1B1C=C2N(c3cccc4c3-c3ccccc3C4(C)C)C(=O)N(c3cccc4c3-c3ccccc3C4(C)C)C3=CB(c4c(C(C)C)cccc4C(C)C)c4cc(-n5c6ccccc6c6ccccc65)cc1c4N23]
15
16
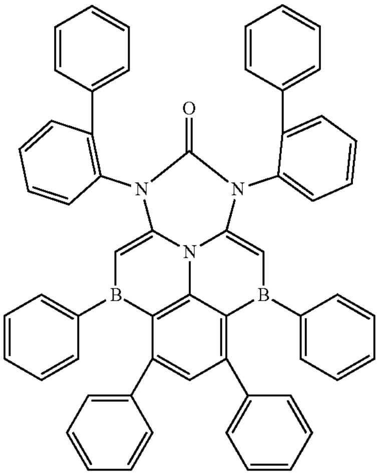 [SMILES: O=C1N(c2ccccc2-c2ccccc2)C2=CB(c3ccccc3)c3c(-c4ccccc4)cc(-c4ccccc4)c4c3N2C(=CB4c2ccccc2)N1c1ccccc1-c1ccccc1]
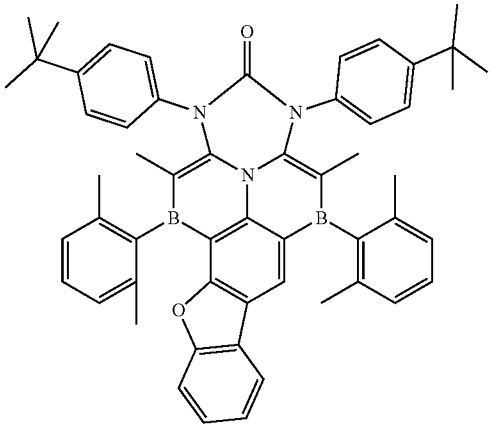 [SMILES: CC1=C2N(c3ccc(C(C)(C)C)cc3)C(=O)N(c3ccc(C(C)(C)C)cc3)C3=C(C)B(c4c(C)cccc4C)c4c(c(cc5c4oc4ccccc45)B1c1c(C)cccc1C)N23]
17

-continued
18
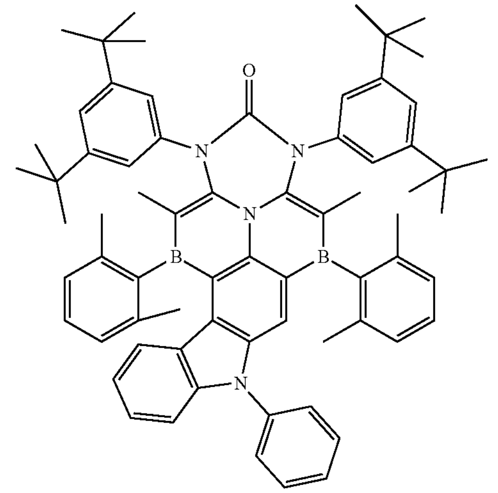 [SMILES: CC1=C2N(c3cc(C(C)(C)C)cc(C(C)(C)C)c3)C(=O)N(c3cc(C(C)(C)C)cc(C(C)(C)C)c3)C3=C(C)B(c4c(C)cccc4C)c4c(c(cc5c4c4ccccc4n5-c4ccccc4)B1c1c(C)cccc1C)N23]
19
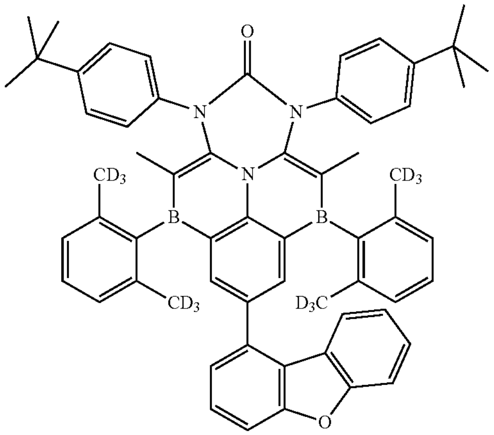 [SMILES: [2H]C([2H])([2H])c1cccc(C([2H])([2H])[2H])c1B1C(C)=C2N(c3ccc(C(C)(C)C)cc3)C(=O)N(c3ccc(C(C)(C)C)cc3)C3=C(C)B(c4c(C([2H])([2H])[2H])cccc4C([2H])([2H])[2H])c4cc(-c5cccc6oc7ccccc7c56)cc1c4N23]
20
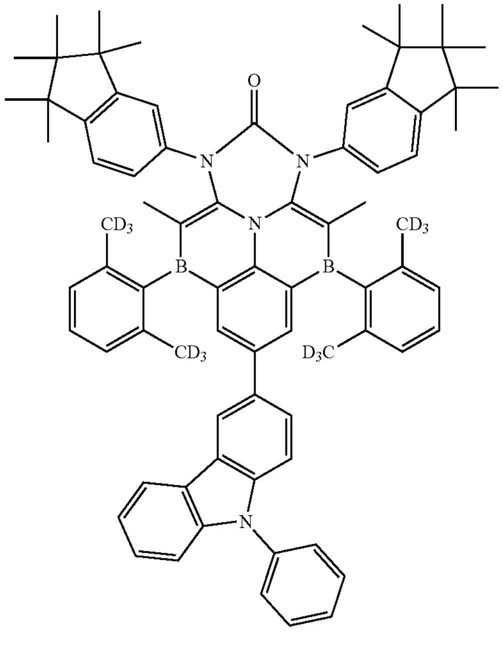

-continued
21
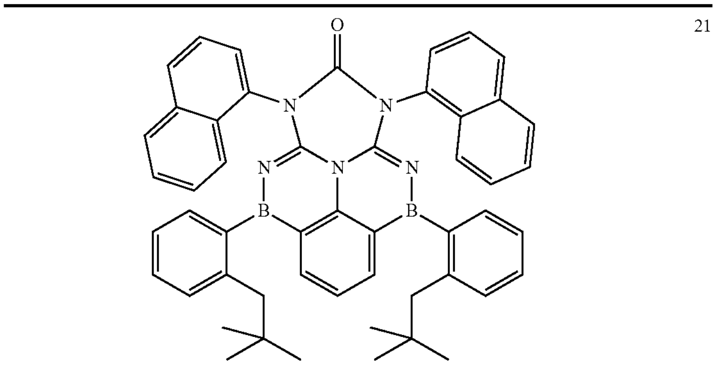
22
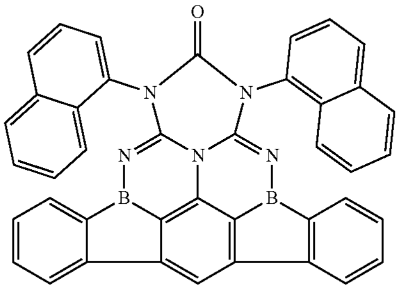 [SMILES: O=C1N(c2cccc3ccccc23)C2=NB3c4ccccc4-c4cc5c6c(c43)N2C(=NB6c2ccccc2-5)N1c1cccc2ccccc12]
23
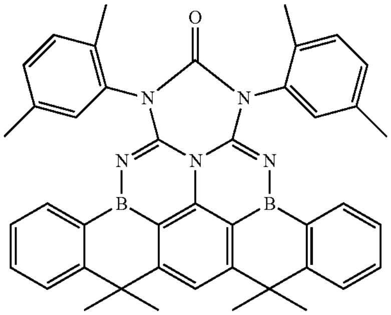
24
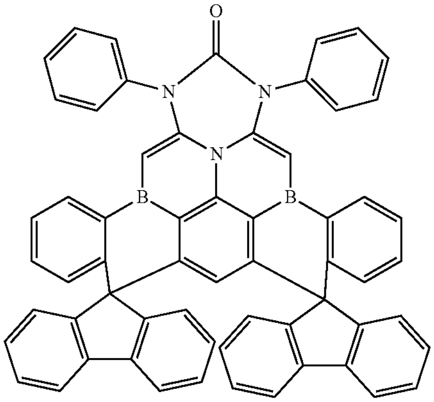 [SMILES: O=C1N(c2ccccc2)C2=CB3c4ccccc4C4(c5ccccc5-c5ccccc54)c4cc5c6c(c43)N2C(=CB6c2ccccc2C52c3ccccc3-c3ccccc32)N1c1ccccc1]

-continued
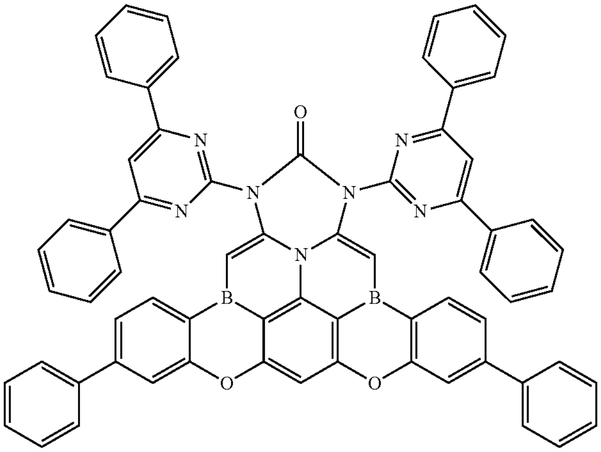 [SMILES: O=C1N(c2nc(-c3ccccc3)cc(-c3ccccc3)n2)C2=CB3c4ccc(-c5ccccc5)cc4Oc4cc5c6c(c43)N2C(=CB6c2ccc(-c3ccccc3)cc2O5)N1c1nc(-c2ccccc2)cc(-c2ccccc2)n1]
25
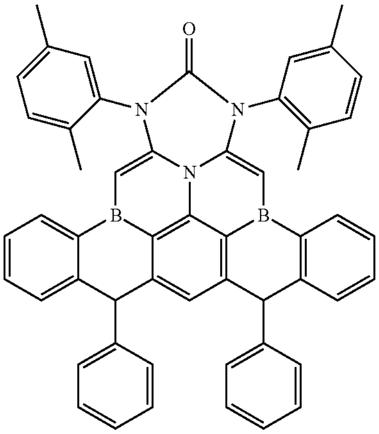 [SMILES: Cc1ccc(C)c(N2C(=O)N(c3cc(C)ccc3C)C3=CB4c5ccccc5C(c5ccccc5)c5cc6c7c(c54)N3C2=CB7c2ccccc2C6c2ccccc2)c1]
26
27
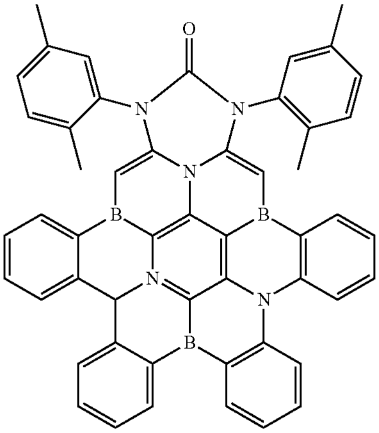

-continued
28
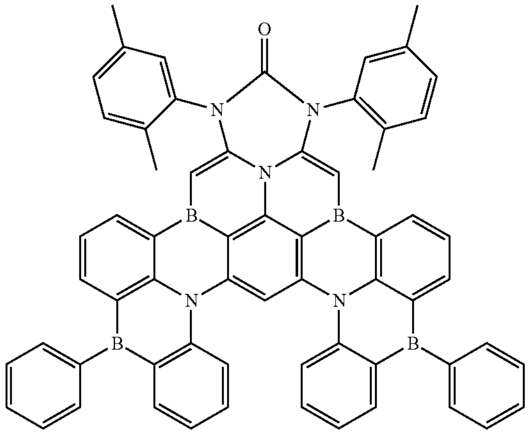 [SMILES: Cc1ccc(C)c(N2C(=O)N(c3cc(C)ccc3C)C3=CB4c5cccc6c5N(c5ccccc5B6c5ccccc5)c5cc6c7c(c54)N3C2=CB7c2cccc3c2N6c2ccccc2B3c2ccccc2)c1]
29
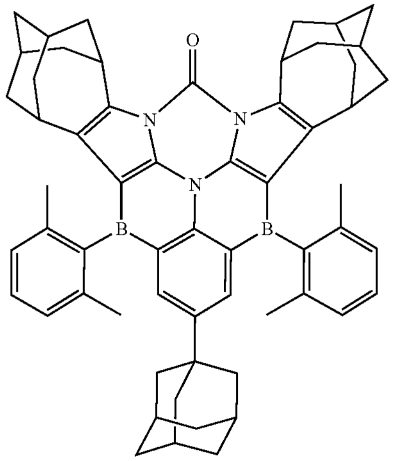 [SMILES: Cc1cccc(C)c1B1c2cc(C34CC5CC(CC(C5)C3)C4)cc3c2-n2c4c1c1c(n4c(=O)n4c5c(c(c24)B3c2c(C)cccc2C)C2CC3CC(C2)CC5C3)C2CC3CC(CC1C3)C2]
30
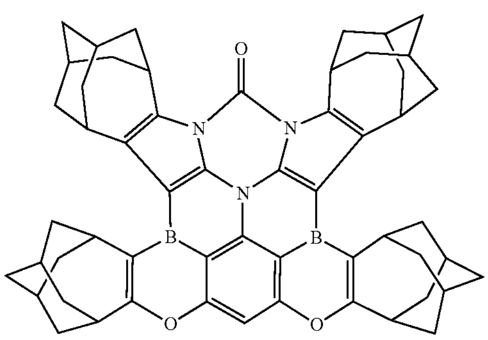 [SMILES: O=c1n2c3c(c4c2n2c5c(c6c(n15)C1CC5CC(CC6C5)C1)B1C5=C(Oc6cc7c(c-2c61)B4C1=C(O7)C2CC4CC(C2)CC1C4)C1CC2CC(C1)CC5C2)C1CC2CC(C1)CC3C2]

-continued
31
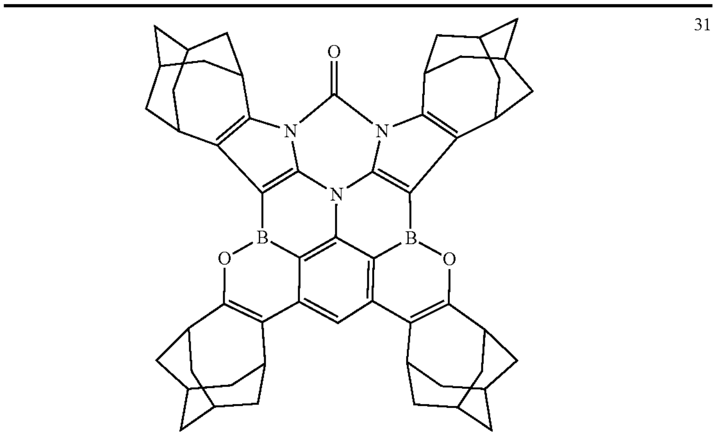
32
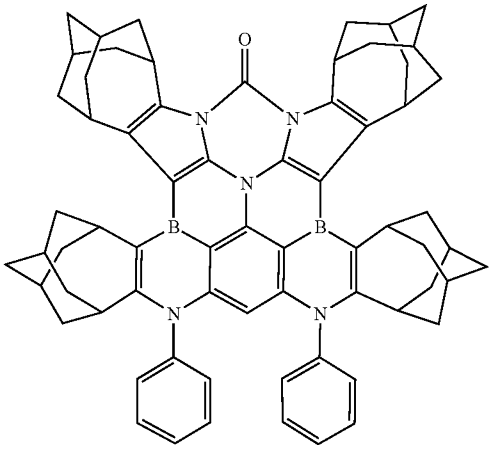 [SMILES: O=c1n2c3c(c4c2n2c5c(c6c(n15)C1CC5CC(CC6C5)C1)B1C5=C(C6CC7CC(CC5C7)C6)N(c5ccccc5)c5cc6c(c-2c51)B4C1=C(C2CC4CC(CC1C4)C2)N6c1ccccc1)C1CC2CC(C1)CC3C2]
33
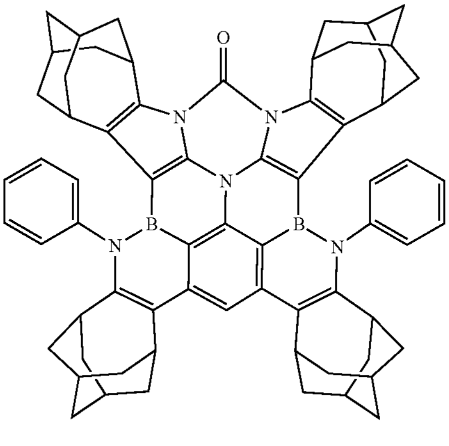 [SMILES: O=c1n2c3c(c4c2n2c5c(c6c(n15)C1CC5CC(CC6C5)C1)B1c5c(cc6c(c5-2)B4N(c2ccccc2)C2=C6C4CC5CC(C4)CC2C5)C2=C(C4CC5CC(CC2C5)C4)N1c1ccccc1)C1CC2CC(C1)CC3C2]

-continued
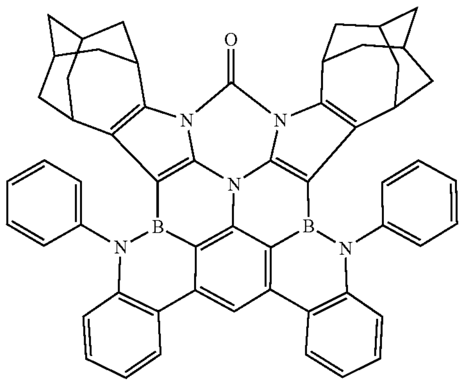 [SMILES: O=c1n2c3c(c4c2n2c5c(c6c(n15)C1CC5CC(CC6C5)C1)B1c5c(cc6c(c5-2)B4N(c2ccccc2)c2ccccc2-6)-c2ccccc2N1c1ccccc1)C1CC2CC(C1)CC3C2]
34
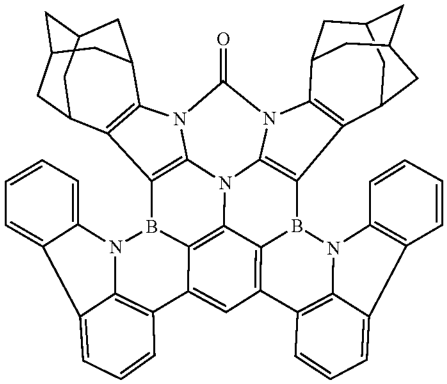 [SMILES: O=c1n2c3c(c4c2n2c5c(c6c(n15)C1CC5CC(CC6C5)C1)B1c5c(cc6c(c5-2)B4n2c4ccccc4c4cccc-6c42)-c2cccc4c5ccccc5n1c24)C1CC2CC(C1)CC3C2]
35
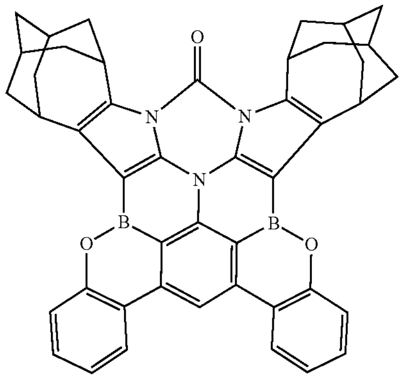 [SMILES: O=c1n2c3c(c4c2n2c5c(c6c(n15)C1CC5CC(CC6C5)C1)B1Oc5ccccc5-c5cc6c(c-2c51)B4Oc1ccccc1-6)C1CC2CC(C1)CC3C2]
36
37
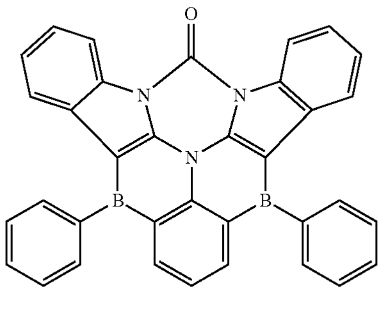 [SMILES: O=c1n2c3ccccc3c3c2n2c4c(c5ccccc5n14)B(c1ccccc1)c1cccc(c1-2)B3c1ccccc1]

-continued
38
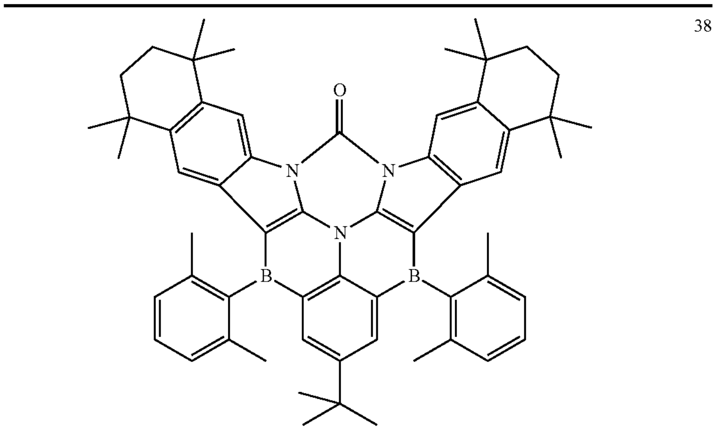
39
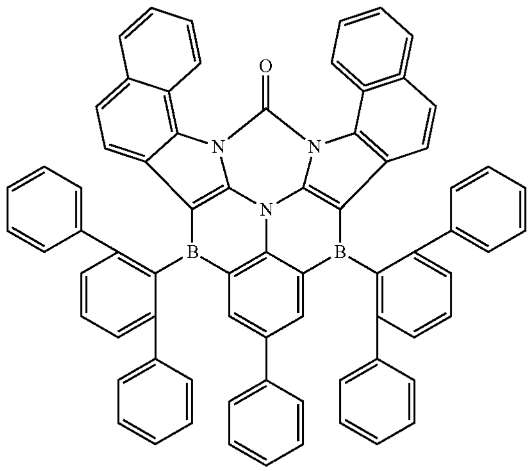
40
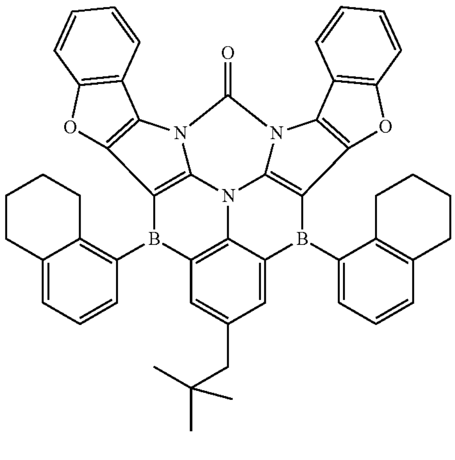 [SMILES: CC(C)(C)Cc1cc2c3c(c1)B(c1cccc4c1CCCC4)c1c4oc5ccccc5c4n4c(=O)n5c6c(oc7ccccc76)c(c5n-3c14)B2c1cccc2c1CCCC2]

-continued
41
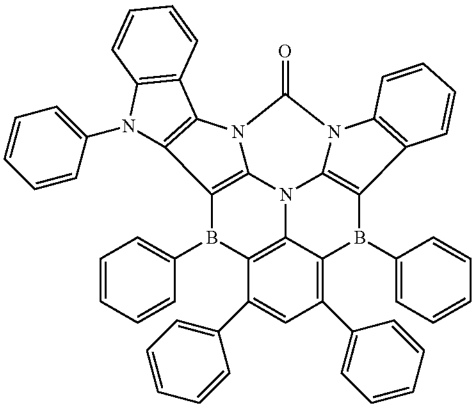 [SMILES: O=c1n2c3ccccc3c3c2n2c4c(c5c(c6ccccc6n5-c5ccccc5)n14)B(c1ccccc1)c1c(-c4ccccc4)cc(-c4ccccc4)c(c1-2)B3c1ccccc1]
42
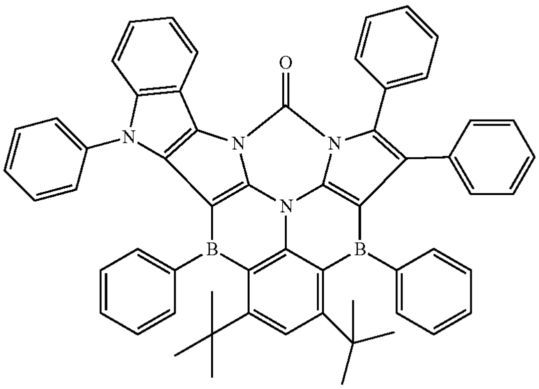 [SMILES: CC(C)(C)c1cc(C(C)(C)C)c2c3c1B(c1ccccc1)c1c(-c4ccccc4)c(-c4ccccc4)n4c(=O)n5c6c7ccccc7n(-c7ccccc7)c6c(c5n-3c14)B2c1ccccc1]
43
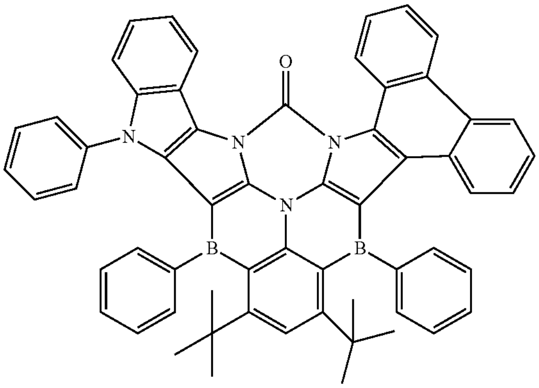 [SMILES: CC(C)(C)c1cc(C(C)(C)C)c2c3c1B(c1ccccc1)c1c4c5ccccc5c5ccccc5c4n4c(=O)n5c6c7ccccc7n(-c7ccccc7)c6c(c5n-3c14)B2c1ccccc1]
44
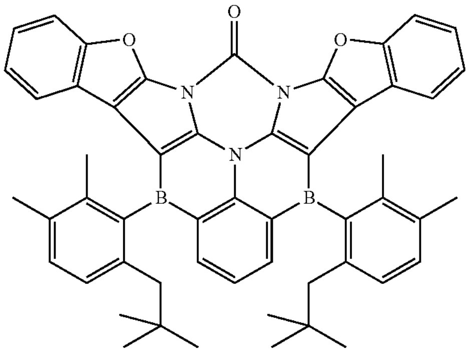 [SMILES: Cc1ccc(CC(C)(C)C)c(B2c3cccc4c3-n3c5c2c2c6ccccc6oc2n5c(=O)n2c5oc6ccccc6c5c(c32)B4c2c(CC(C)(C)C)ccc(C)c2C)c1C]

-continued
45
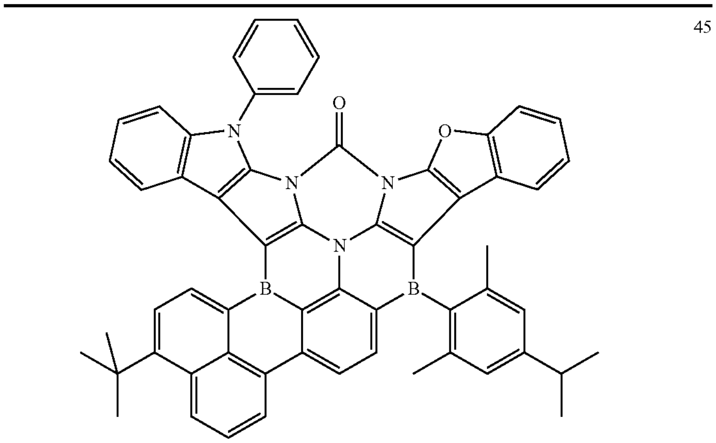
46
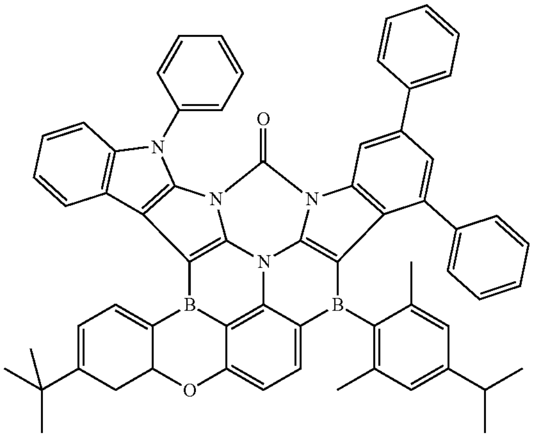 [SMILES: Cc1cc(C(C)C)cc(C)c1B1c2ccc3c4c2-n2c5c1c1c(-c6ccccc6)cc(-c6ccccc6)cc1n5c(=O)n1c2c(c2c5ccccc5n(-c5ccccc5)c21)B4C1=CC=C(C(C)(C)C)CC1O3]
47
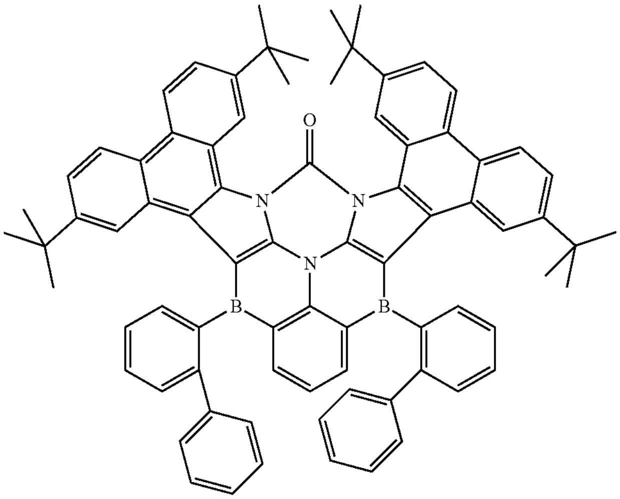 [SMILES: CC(C)(C)c1ccc2c3ccc(C(C)(C)C)cc3c3c(c4c5n6c7c(c8c9cc(C(C)(C)C)ccc9c9ccc(C(C)(C)C)cc9c8n7c(=O)n35)B(c3ccccc3-c3ccccc3)c3cccc(c3-6)B4c3ccccc3-c3ccccc3)c2c1]

-continued
48
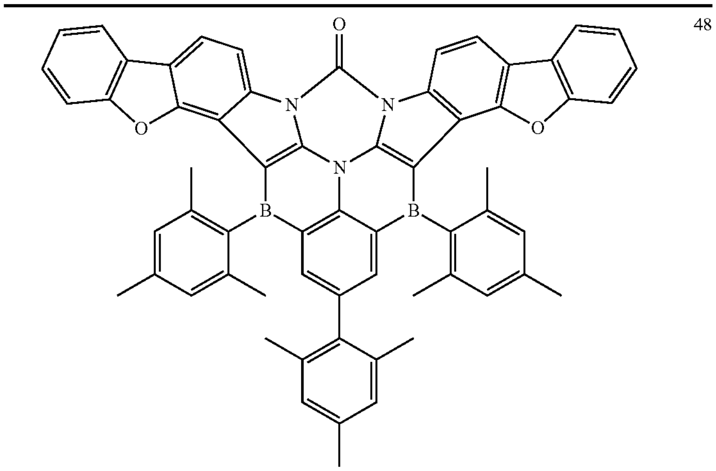
49
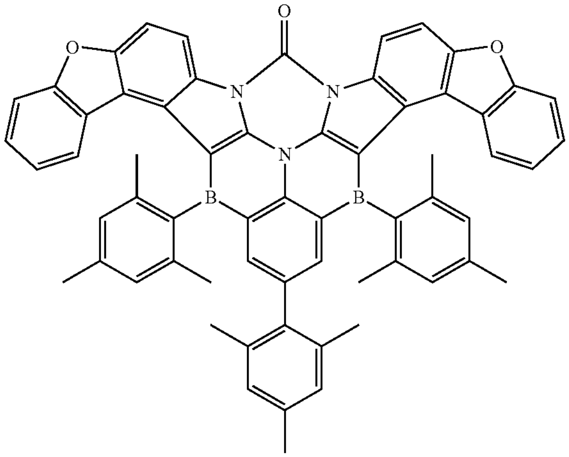 [SMILES: Cc1cc(C)c(B2c3cc(-c4c(C)cc(C)cc4C)cc4c3-n3c5c2c2c6c(ccc2n5c(=O)n2c5ccc7oc8ccccc8c7c5c(c32)B4c2c(C)cc(C)cc2C)oc2ccccc26)c(C)c1]
50
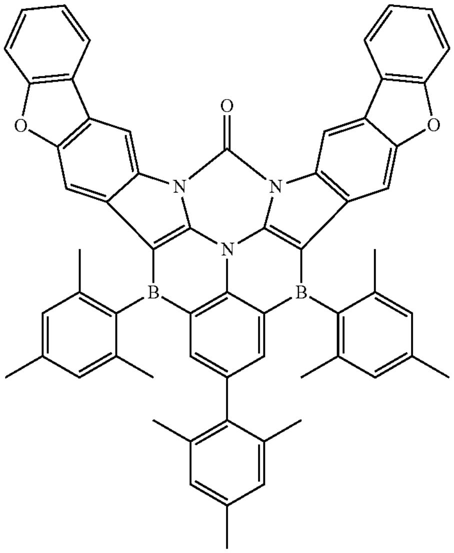 [SMILES: Cc1cc(C)c(B2c3cc(-c4c(C)cc(C)cc4C)cc4c3-n3c5c2c2cc6oc7ccccc7c6cc2n5c(=O)n2c5cc6c(cc5c(c32)B4c2c(C)cc(C)cc2C)oc2ccccc26)c(C)c1]

-continued
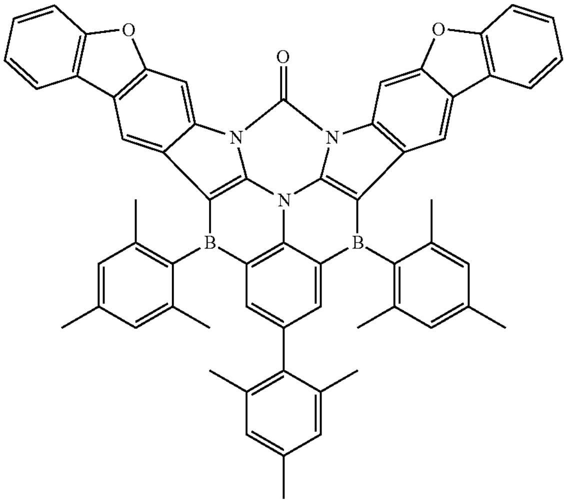 [SMILES: Cc1cc(C)c(B2c3cc(-c4c(C)cc(C)cc4C)cc4c3-n3c5c2c2cc6c(cc2n5c(=O)n2c5cc7oc8ccccc8c7cc5c(c32)B4c2c(C)cc(C)cc2C)oc2ccccc26)c(C)c1]
51
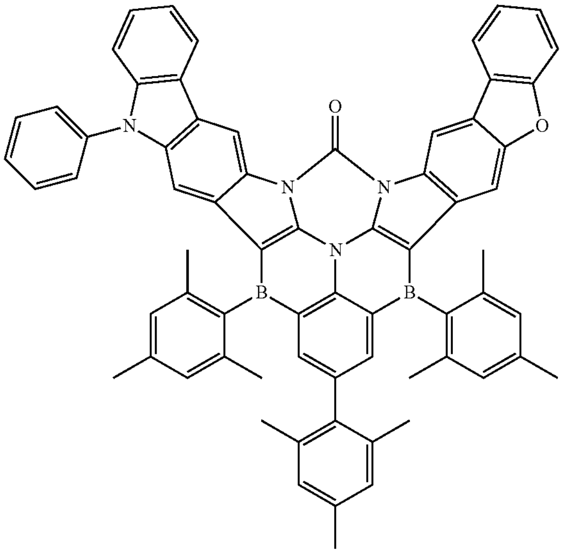 [SMILES: Cc1cc(C)c(B2c3cc(-c4c(C)cc(C)cc4C)cc4c3-n3c5c2c2cc6oc7ccccc7c6cc2n5c(=O)n2c5cc6c7ccccc7n(-c7ccccc7)c6cc5c(c32)B4c2c(C)cc(C)cc2C)c(C)c1]
52
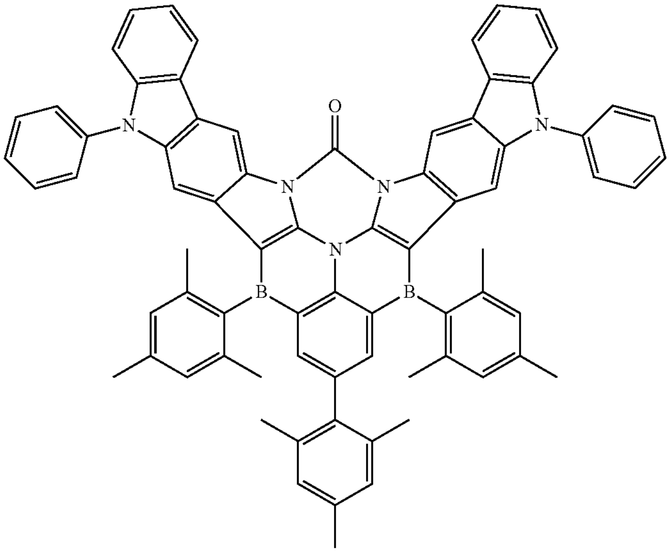 [SMILES: Cc1cc(C)c(B2c3cc(-c4c(C)cc(C)cc4C)cc4c3-n3c5c2c2cc6c(cc2n5c(=O)n2c5cc7c8ccccc8n(-c8ccccc8)c7cc5c(c32)B4c2c(C)cc(C)cc2C)c2ccccc2n6-c2ccccc2)c(C)c1]
53

-continued
54
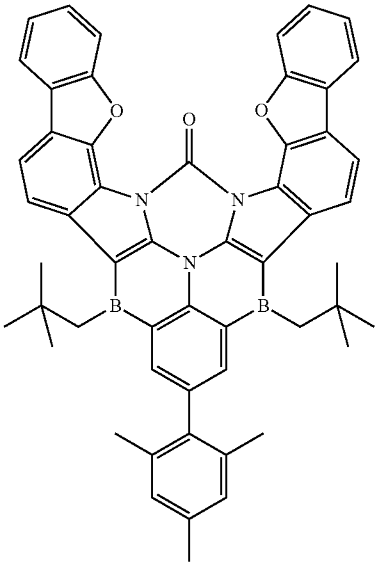 [SMILES: Cc1cc(C)c(-c2cc3c4c(c2)B(CC(C)(C)C)c2c5ccc6c7ccccc7oc6c5n5c(=O)n6c7c(ccc8c9ccccc9oc87)c(c6n-4c25)B3CC(C)(C)C)c(C)c1]
55
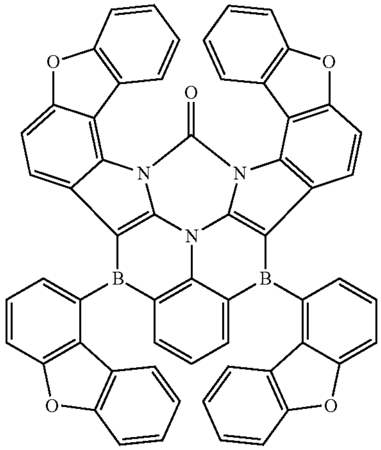 [SMILES: O=c1n2c3c(ccc4oc5ccccc5c43)c3c2n2c4c(c5ccc6oc7ccccc7c6c5n14)B(c1cccc4oc5ccccc5c14)c1cccc(c1-2)B3c1cccc2oc3ccccc3c12]
56
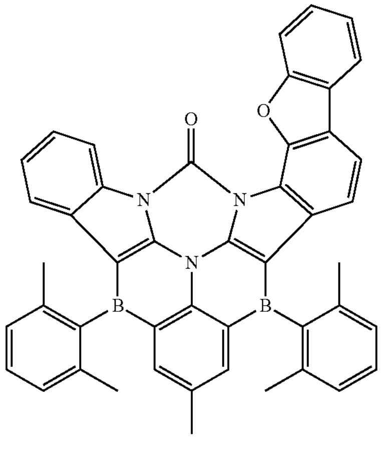 [SMILES: Cc1cc2c3c(c1)B(c1c(C)cccc1C)c1c4ccc5c6ccccc6oc5c4n4c(=O)n5c6ccccc6c(c5n-3c14)B2c1c(C)cccc1C]

-continued
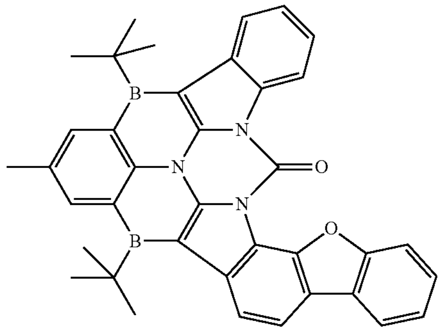 [SMILES: Cc1cc2c3c(c1)B(C(C)(C)C)c1c4ccc5c6ccccc6oc5c4n4c(=O)n5c6ccccc6c(c5n-3c14)B2C(C)(C)C]
57
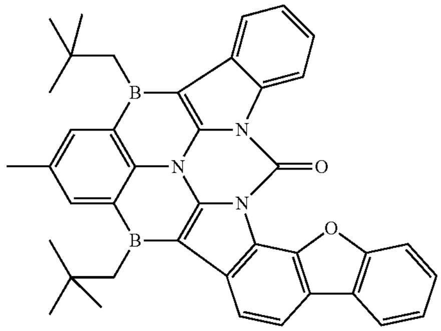 [SMILES: Cc1cc2c3c(c1)B(CC(C)(C)C)c1c4ccc5c6ccccc6oc5c4n4c(=O)n5c6ccccc6c(c5n-3c14)B2CC(C)(C)C]
58
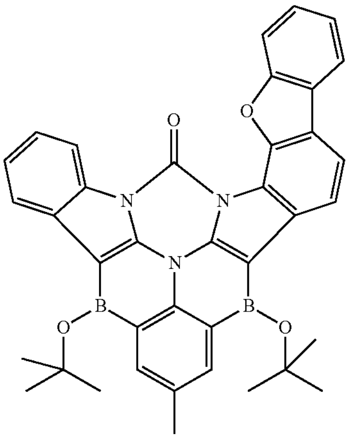 [SMILES: Cc1cc2c3c(c1)B(OC(C)(C)C)c1c4ccc5c6ccccc6oc5c4n4c(=O)n5c6ccccc6c(c5n-3c14)B2OC(C)(C)C]
59
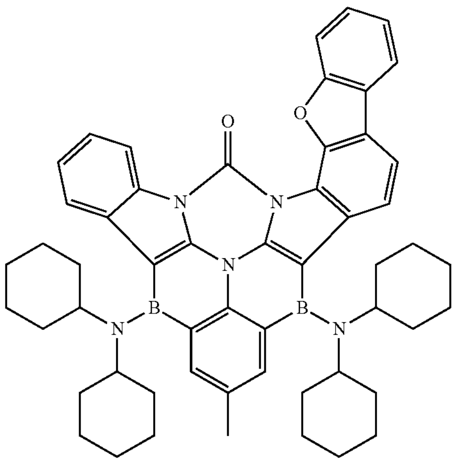 [SMILES: Cc1cc2c3c(c1)B(N(C1CCCCC1)C1CCCCC1)c1c4ccc5c6ccccc6oc5c4n4c(=O)n5c6ccccc6c(c5n-3c14)B2N(C1CCCCC1)C1CCCCC1]
60

-continued
61
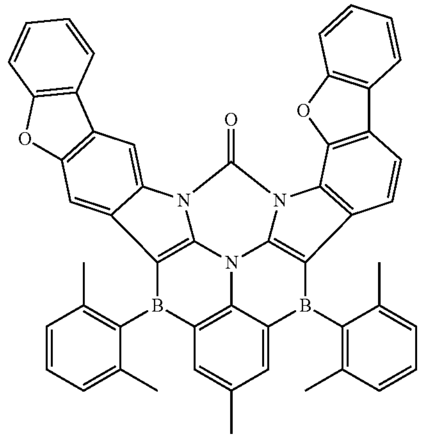 [SMILES: Cc1cc2c3c(c1)B(c1c(C)cccc1C)c1c4ccc5c6ccccc6oc5c4n4c(=O)n5c6cc7c(cc6c(c5n-3c14)B2c1c(C)cccc1C)oc1ccccc17]
62
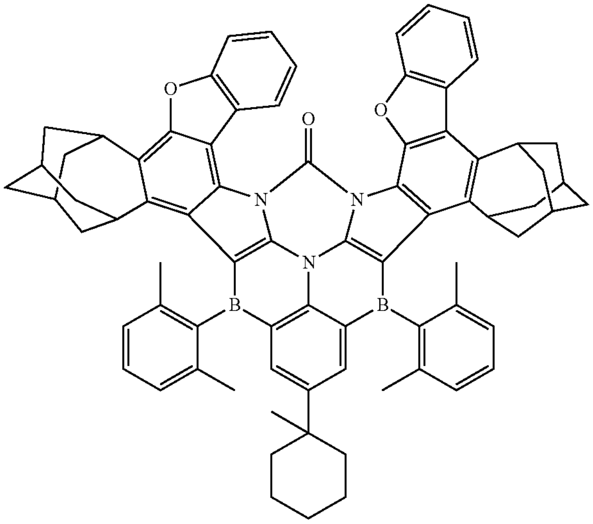 [SMILES: Cc1cccc(C)c1B1c2cc(C3(C)CCCCC3)cc3c2-n2c4c1c1c5c(c6c7ccccc7oc6c1n4c(=O)n1c4c(c6c(c7oc8ccccc8c74)C4CC7CC(C4)CC6C7)c(c21)B3c1c(C)cccc1C)C1CC2CC(CC5C2)C1]
63
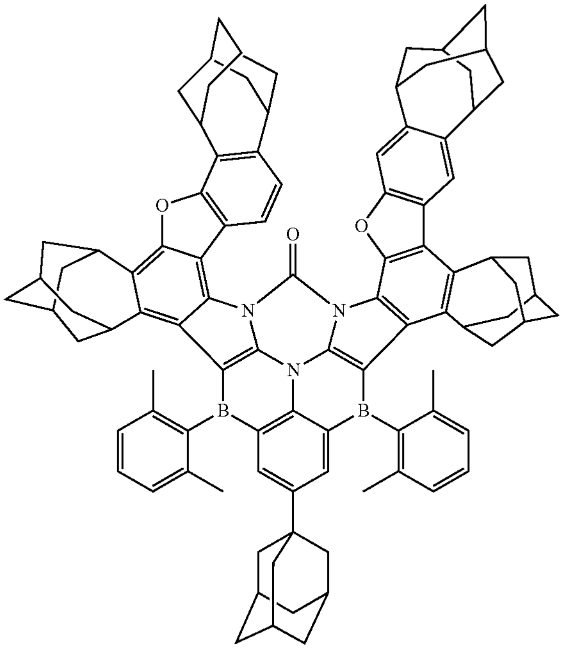 [SMILES: Cc1cccc(C)c1B1c2cc(C34CC5CC(CC(C5)C3)C4)cc3c2-n2c4c1c1c5c(c6c7cc8c(cc7oc6c1n4c(=O)n1c4c(c6c(c7oc9c(C%10CCCCC%10)c(C%10CCCCC%10)ccc9c74)C4CC7CC(C4)CC6C7)c(c21)B3c1c(C)cccc1C)C1CC2CC(C1)CC8C2)C1CC2CC(CC5C2)C1]

-continued
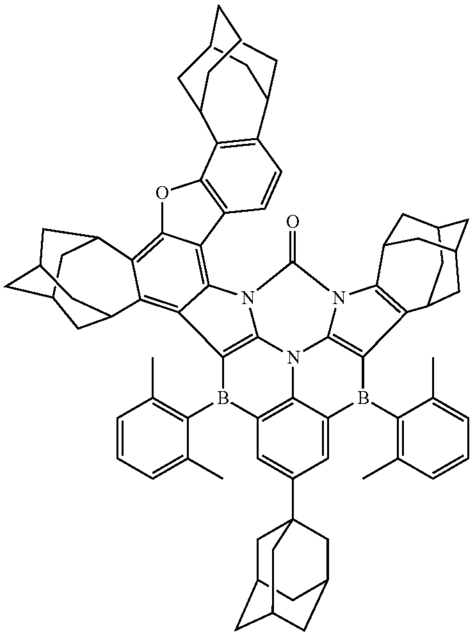 [SMILES: Cc1cccc(C)c1B1c2cc(C34CC5CC(CC(C5)C3)C4)cc3c2-n2c4c1c1c(n4c(=O)n4c5c(c6c(c7oc8c(C9CCCCC9)c(C9CCCCC9)ccc8c75)C5CC7CC(C5)CC6C7)c(c24)B3c2c(C)cccc2C)C2CC3CC(CC1C3)C2]
64
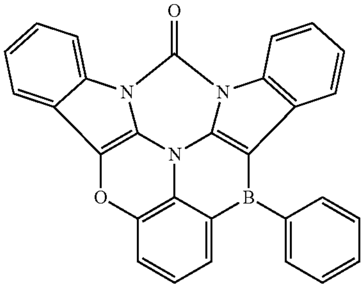 [SMILES: O=c1n2c3ccccc3c3c2n2c4c(cccc4oc4c5ccccc5n1c42)B3c1ccccc1]
65
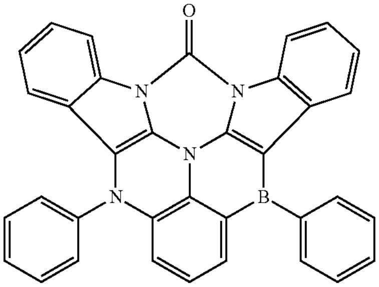 [SMILES: O=c1n2c3ccccc3c3c2n2c4c(cccc4n(-c4ccccc4)c4c5ccccc5n1c42)B3c1ccccc1]
66
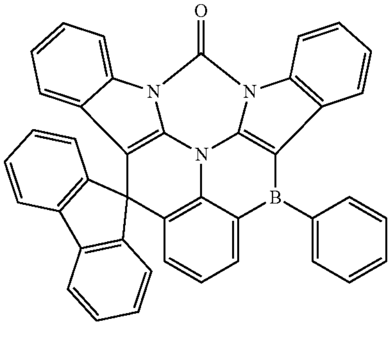 [SMILES: O=c1n2c3ccccc3c3c2n2c4c(c5ccccc5n14)C1(c4ccccc4-c4ccccc41)c1cccc(c1-2)B3c1ccccc1]
67

-continued
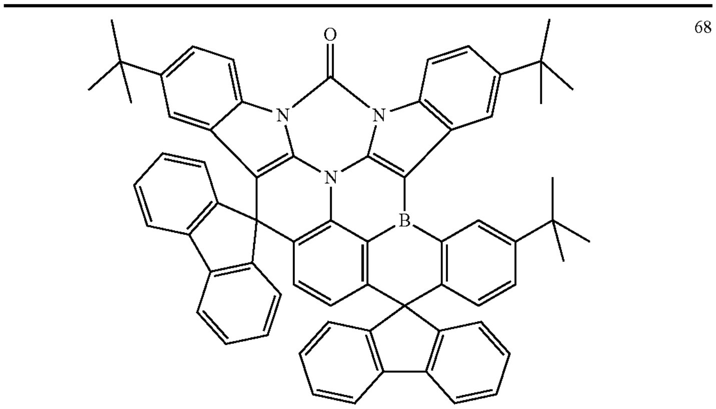
68
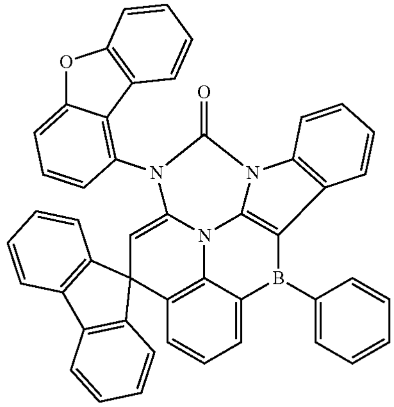 [SMILES: O=C1N(c2cccc3oc4ccccc4c23)C2=CC3(c4ccccc4-c4ccccc43)c3cccc4c3N2c2c(c3ccccc3n21)B4c1ccccc1]
69
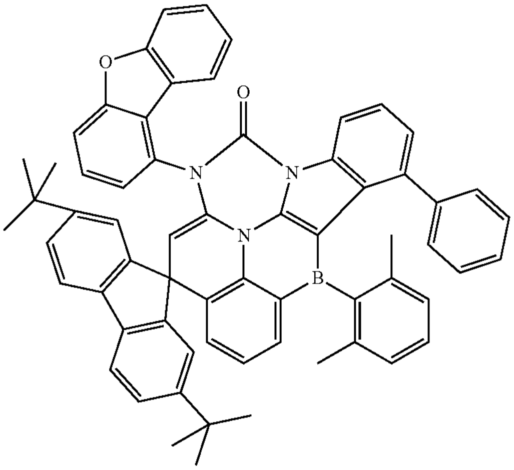 [SMILES: Cc1cccc(C)c1B1c2cccc3c2N2C(=CC34c3cc(C(C)(C)C)ccc3-c3ccc(C(C)(C)C)cc34)N(c3cccc4oc5ccccc5c34)C(=O)n3c2c1c1c(-c2ccccc2)cccc13]
70
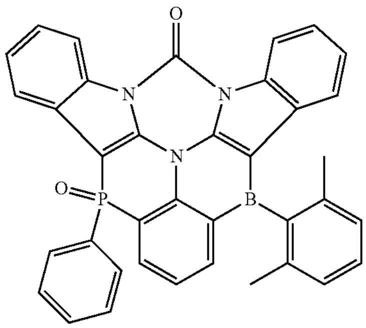 [SMILES: Cc1cccc(C)c1B1c2cccc3c2-n2c4c1c1ccccc1n4c(=O)n1c4ccccc4c(c21)P3(=O)c1ccccc1]
71

-continued
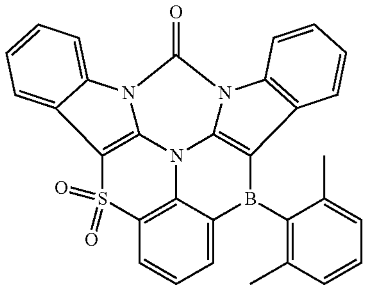 [SMILES: Cc1cccc(C)c1B1c2cccc3c2-n2c4c1c1ccccc1n4c(=O)n1c4ccccc4c(c21)S3(=O)=O]
72
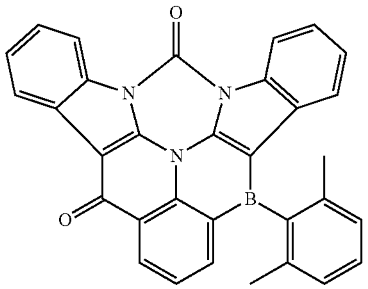 [SMILES: Cc1cccc(C)c1B1c2cccc3c(=O)c4c5ccccc5n5c(=O)n6c7ccccc7c1c6n(c23)c45]
73
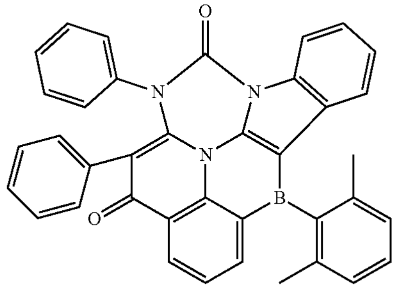 [SMILES: Cc1cccc(C)c1B1c2cccc3c(=O)c(-c4ccccc4)c4n(-c5ccccc5)c(=O)n5c6ccccc6c1c5n4c23]
74
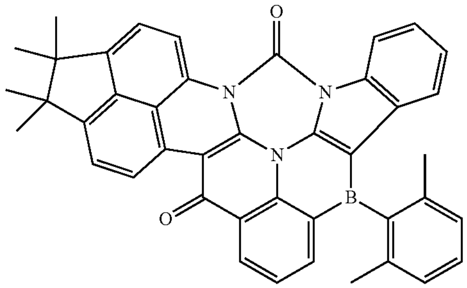 [SMILES: Cc1cccc(C)c1B1c2cccc3c(=O)c4c5ccc6c7c(ccc(c75)n5c(=O)n7c8ccccc8c1c7n(c23)c45)C(C)(C)C6(C)C]
75
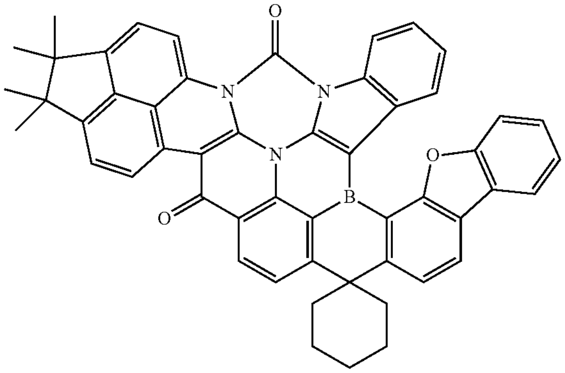 [SMILES: CC1(C)c2ccc3c4c(=O)c5ccc6c7c5n5c8c(c9ccccc9n8c(=O)n(c8ccc(c2c38)C1(C)C)c45)B7c1c(ccc2c1oc1ccccc12)C61CCCCC1]
76

-continued
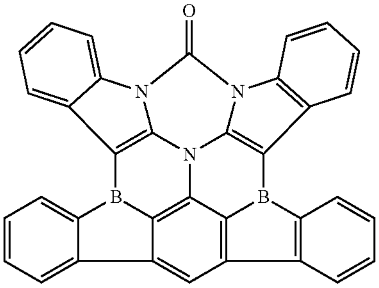 [SMILES: O=c1n2c3ccccc3c3c2n2c4c(c5ccccc5n14)B1c4ccccc4-c4cc5c(c-2c41)B3c1ccccc1-5]
77
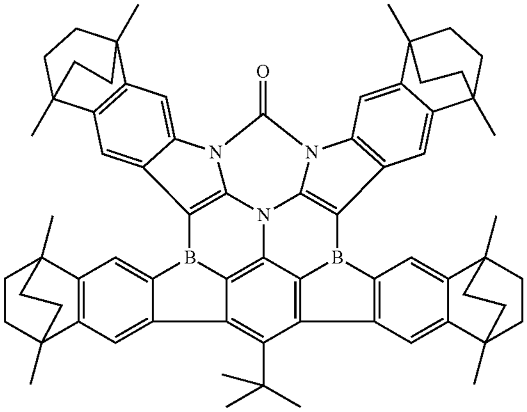 [SMILES: CC(C)(C)c1c2c3c4c5c1-c1cc6c(cc1B5c1c5cc7c(cc5n5c(=O)n8c9cc%10c(cc9c(c8n-4c15)B3c1cc3c(cc1-2)C1(C)CCC3(C)CC1)C1(C)CCC%10(C)CC1)C1(C)CCC7(C)CC1)C1(C)CCC6(C)CC1]
78
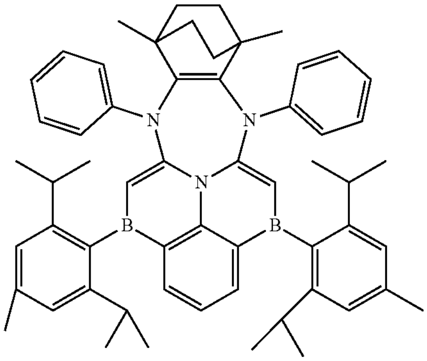
79
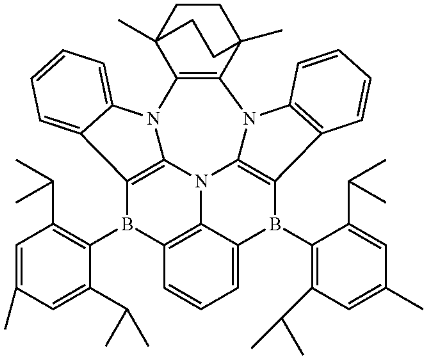
80

-continued
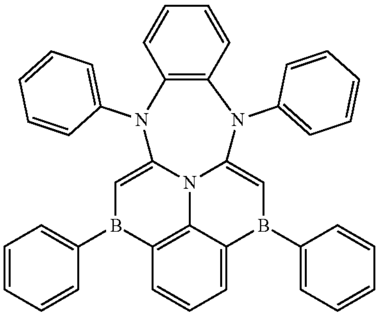 [SMILES: C1=c2n3c(n(-c4ccccc4)c4ccccc4n2-c2ccccc2)=CB(c2ccccc2)c2cccc(c2-3)B1c1ccccc1]
81
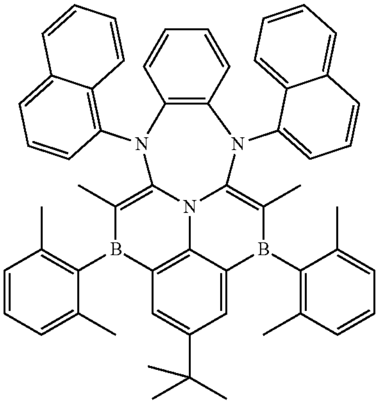 [SMILES: CC1=c2n3c(n(-c4cccc5ccccc45)c4ccccc4n2-c2cccc4ccccc24)=C(C)B(c2c(C)cccc2C)c2cc(C(C)(C)C)cc(c2-3)B1c1c(C)cccc1C]
82
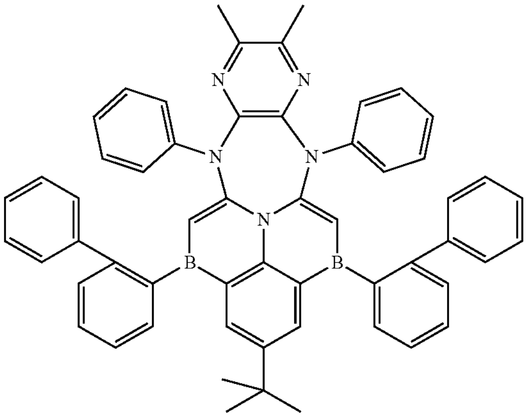 [SMILES: Cc1nc2c(nc1C)n(-c1ccccc1)c1n3c(n2-c2ccccc2)=CB(c2ccccc2-c2ccccc2)c2cc(C(C)(C)C)cc(c2-3)B(c2ccccc2-c2ccccc2)C=1]
83
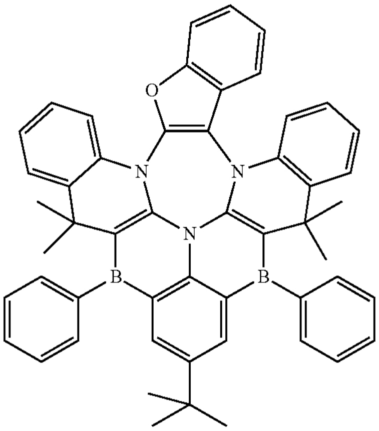 [SMILES: CC(C)(C)c1cc2c3c(c1)B(c1ccccc1)C1=c4n-3c3n(c5oc6ccccc6c5n4-c4ccccc4C1(C)C)-c1ccccc1C(C)(C)C=3B2c1ccccc1]
84

-continued
85
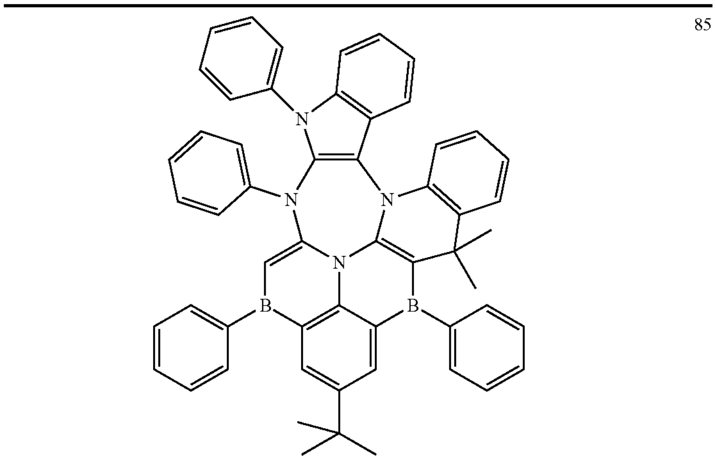
86
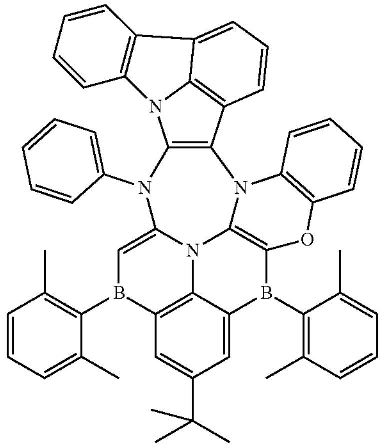 [SMILES: Cc1cccc(C)c1B1C=c2n3c4c(oc5ccccc5n4c4c5cccc6c7ccccc7n(c65)c4n2-c2ccccc2)B(c2c(C)cccc2C)c2cc(C(C)(C)C)cc1c2-3]
87
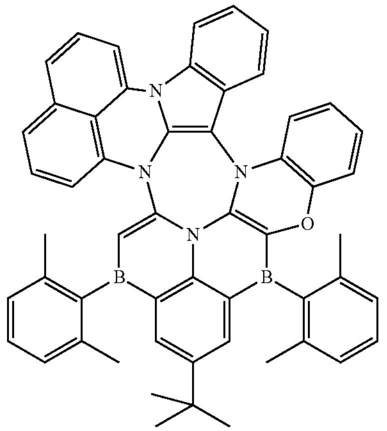 [SMILES: Cc1cccc(C)c1B1C=c2n3c4c(oc5ccccc5n4c4c5ccccc5n5c6cccc7cccc(c76)n2c45)B(c2c(C)cccc2C)c2cc(C(C)(C)C)cc1c2-3]

-continued
88
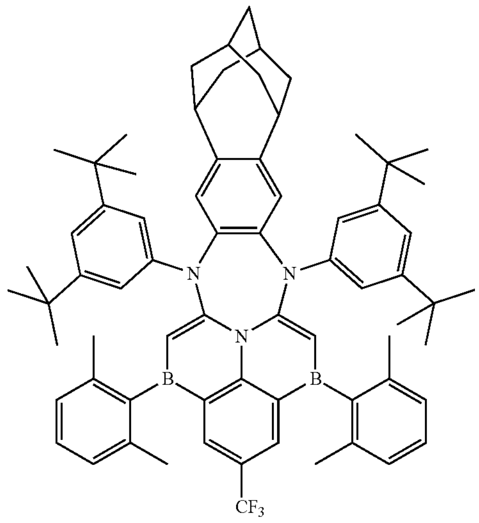 [SMILES: Cc1cccc(C)c1B1C=c2n3c(n(-c4cc(C(C)(C)C)cc(C(C)(C)C)c4)c4cc5c(cc4n2-c2cc(C(C)(C)C)cc(C(C)(C)C)c2)C2CC4CC(C2)CC5C4)=CB(c2c(C)cccc2C)c2cc(C(F)(F)F)cc1c2-3]
89
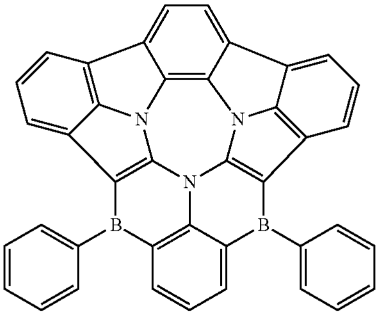 [SMILES: c1ccc(B2c3cccc4c3-n3c5c2c2cccc6c7ccc8c9cccc%10c(c3n(c%109)c8c7n5c26)B4c2ccccc2)cc1]
90
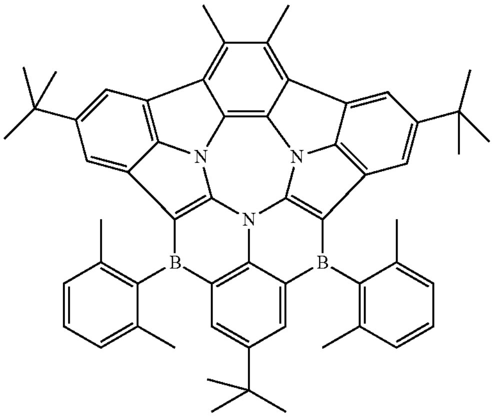 [SMILES: Cc1cccc(C)c1B1c2cc(C(C)(C)C)cc3c2-n2c4c1c1cc(C(C)(C)C)cc5c6c(C)c(C)c7c8cc(C(C)(C)C)cc9c(c2n(c98)c7c6n4c15)B3c1c(C)cccc1C]

-continued
91
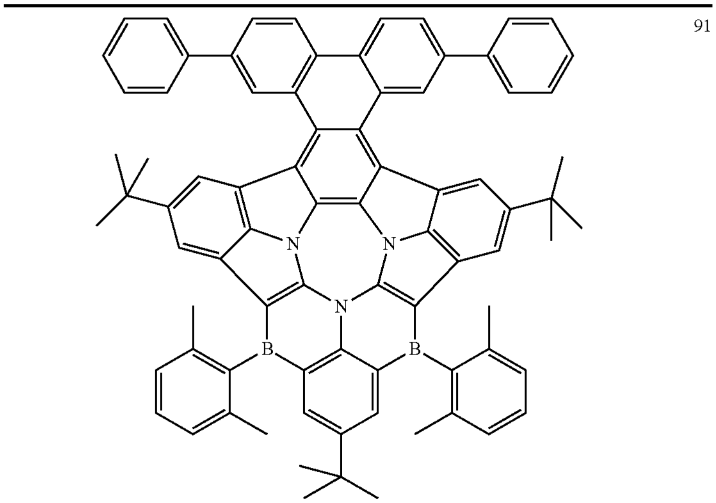
92
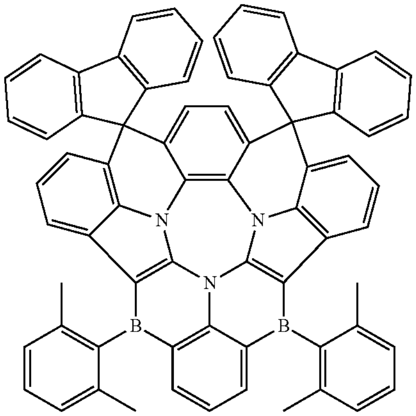 [SMILES: Cc1cccc(C)c1B1c2cccc3c2-n2c4c1c1cccc5c1n4c1c(ccc4c1n1c6c(cccc6c(c21)B3c1c(C)cccc1C)C41c2ccccc2-c2ccccc21)C51c2ccccc2-c2ccccc21]
93
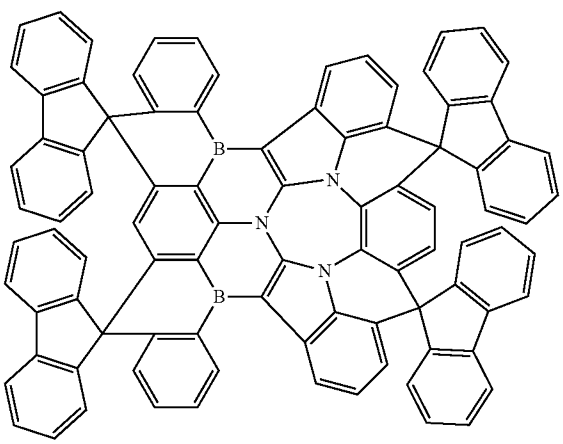 [SMILES: c1ccc2c(c1)B1c3c(cc4c5c3-n3c6c1c1cccc7c1n6c1c(ccc6c1n1c8c(cccc8c(c31)B5c1ccccc1C41c3ccccc3-c3ccccc31)C61c3ccccc3-c3ccccc31)C71c3ccccc3-c3ccccc31)C21c2ccccc2-c2ccccc21]

-continued
94
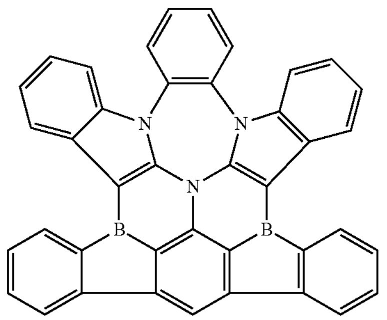 [SMILES: c1ccc2c(c1)B1c3c-2cc2c4c3-n3c5c1c1ccccc1n5c1ccccc1n1c5ccccc5c(c31)B4c1ccccc1-2]
95
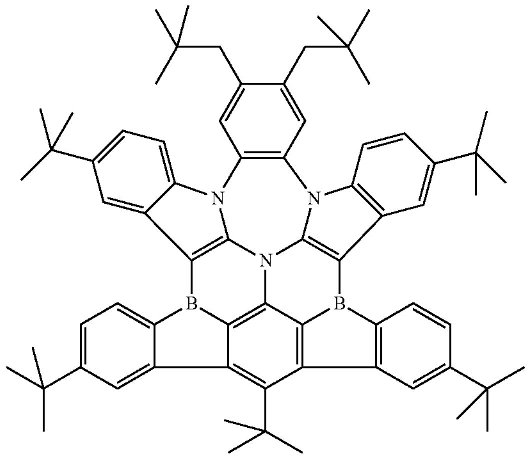 [SMILES: CC(C)(C)Cc1cc2c(cc1CC(C)(C)C)n1c3ccc(C(C)(C)C)cc3c3c1n1c4c(c5cc(C(C)(C)C)ccc5n24)B2c4ccc(C(C)(C)C)cc4-c4c2c-1c1c(c4C(C)(C)C)-c2cc(C(C)(C)C)ccc2B13]
96
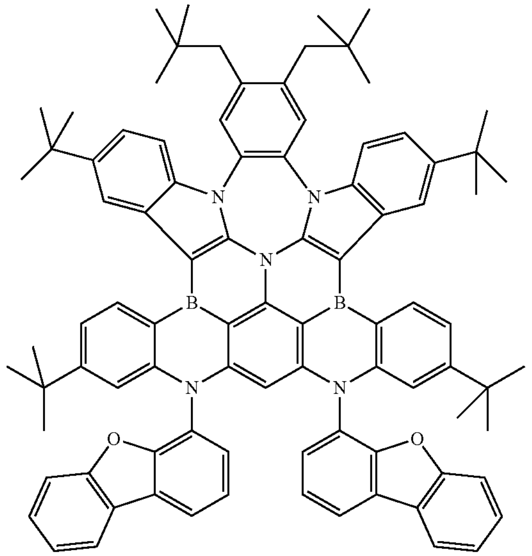 [SMILES: CC(C)(C)Cc1cc2c(cc1CC(C)(C)C)n1c3ccc(C(C)(C)C)cc3c3c1n1c4c(c5cc(C(C)(C)C)ccc5n24)B2c4ccc(C(C)(C)C)cc4N(c4cccc5c4oc4ccccc45)c4cc5c(c-1c42)B3c1ccc(C(C)(C)C)cc1N5c1cccc2c1oc1ccccc12]

-continued
97
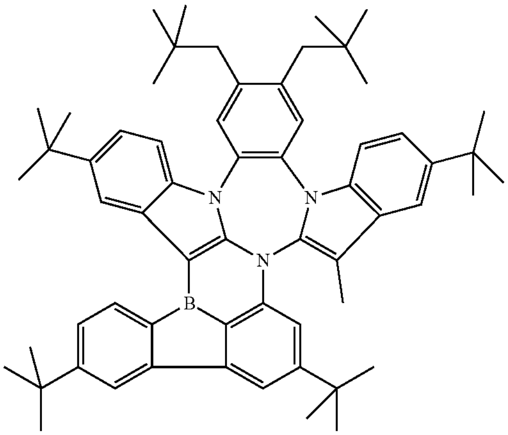 [SMILES: Cc1c2cc(C(C)(C)C)ccc2n2c3cc(CC(C)(C)C)c(CC(C)(C)C)cc3n3c4ccc(C(C)(C)C)cc4c4c3n(c12)-c1cc(C(C)(C)C)cc2c1B4c1ccc(C(C)(C)C)cc1-2]
98
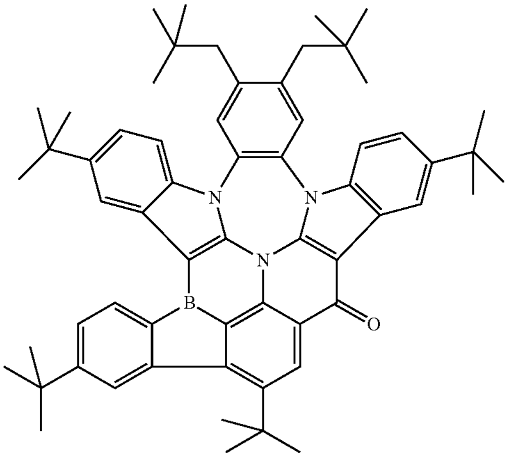 [SMILES: CC(C)(C)Cc1cc2c(cc1CC(C)(C)C)n1c3ccc(C(C)(C)C)cc3c3c(=O)c4cc(C(C)(C)C)c5c6c4n(c4c(c7cc(C(C)(C)C)ccc7n24)B6c2ccc(C(C)(C)C)cc2-5)c31]
99
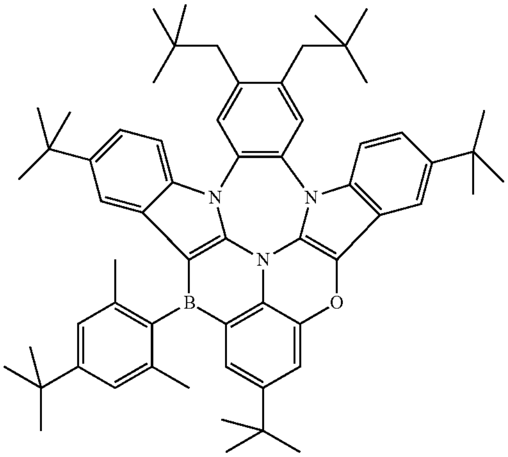 [SMILES: Cc1cc(C(C)(C)C)cc(C)c1B1c2cc(C(C)(C)C)cc3oc4c5cc(C(C)(C)C)ccc5n5c6cc(CC(C)(C)C)c(CC(C)(C)C)cc6n6c7ccc(C(C)(C)C)cc7c1c6n(c23)c45]

-continued
100
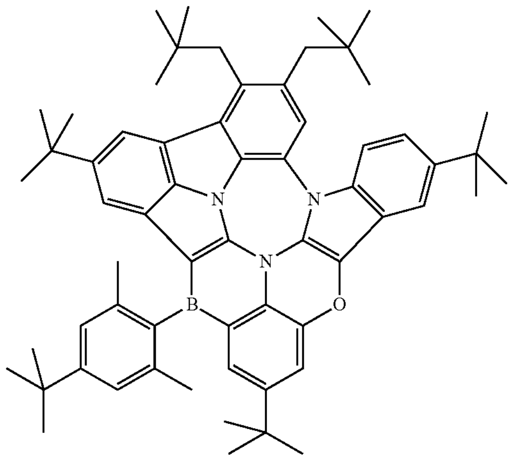 [SMILES: Cc1cc(C(C)(C)C)cc(C)c1B1c2cc(C(C)(C)C)cc3oc4c5cc(C(C)(C)C)ccc5n5c6cc(CC(C)(C)C)c(CC(C)(C)C)c7c8cc(C(C)(C)C)cc9c1c(n(c98)c76)n(c23)c45]
101
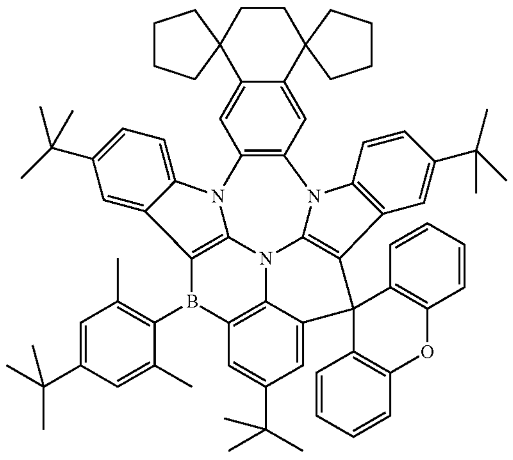 [SMILES: Cc1cc(C(C)(C)C)cc(C)c1B1c2cc(C(C)(C)C)cc3c2-n2c4c1c1cc(C(C)(C)C)ccc1n4c1cc4c(cc1n1c5ccc(C(C)(C)C)cc5c(c21)C31c2ccccc2Oc2ccccc21)C1(CCCC1)CCC41CCCC1]
102
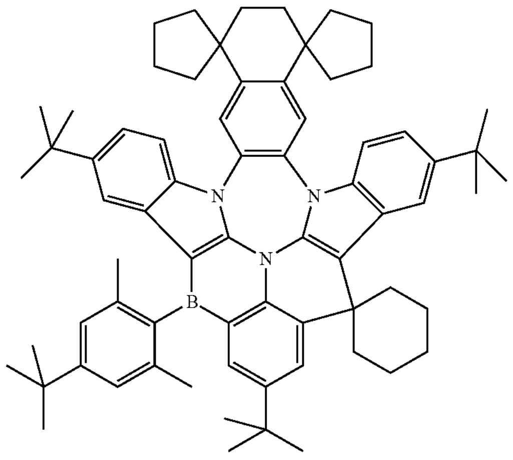 [SMILES: Cc1cc(C(C)(C)C)cc(C)c1B1c2cc(C(C)(C)C)cc3c2-n2c4c1c1cc(C(C)(C)C)ccc1n4c1cc4c(cc1n1c5ccc(C(C)(C)C)cc5c(c21)C31CCCCC1)C1(CCCC1)CCC41CCCC1]

-continued
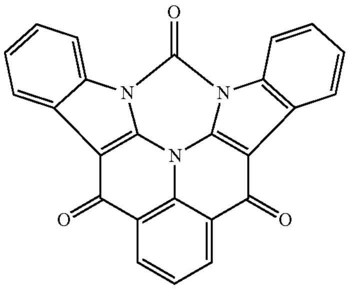 [SMILES: O=c1c2cccc3c(=O)c4c5ccccc5n5c(=O)n6c7ccccc7c1c6n(c23)c45]
103
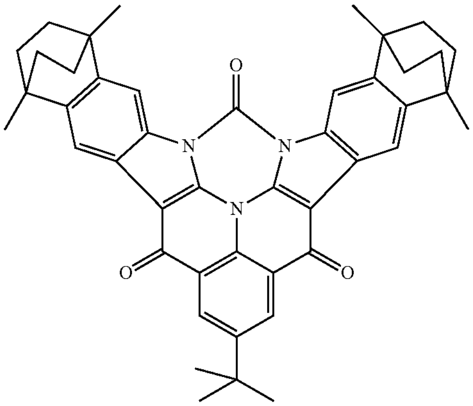
104
105
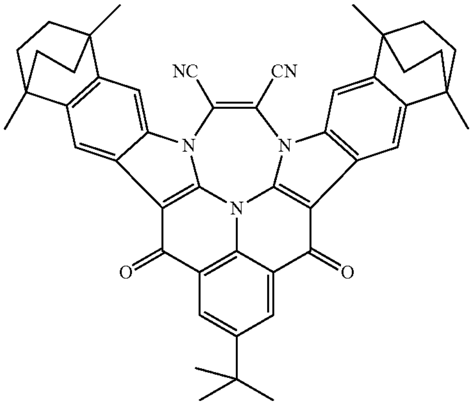
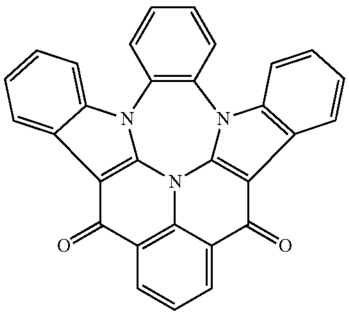 [SMILES: O=c1c2cccc3c(=O)c4c5ccccc5n5c6ccccc6n6c7ccccc7c1c6n(c23)c45]
106

-continued
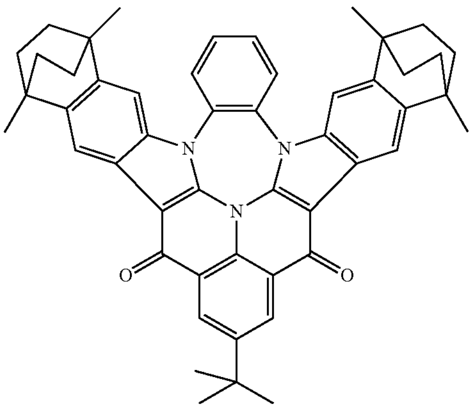
107
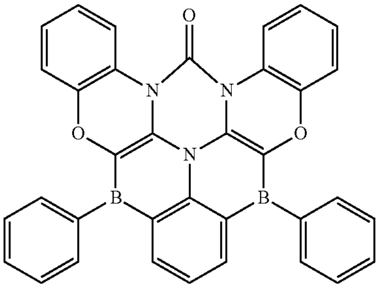 [SMILES: O=c1n2c3ccccc3oc3c-2n2c4c(oc5ccccc5n1-4)B(c1ccccc1)c1cccc(c1-2)B3c1ccccc1]
108
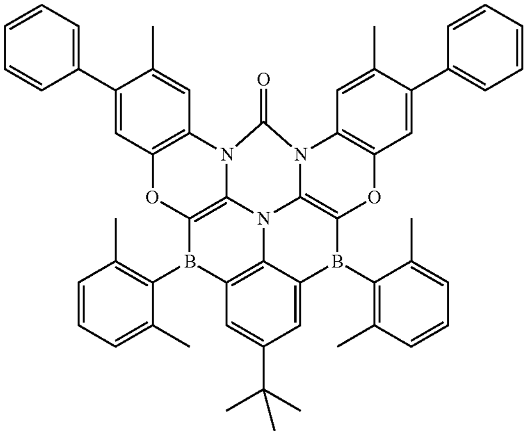 [SMILES: Cc1cc2c(cc1-c1ccccc1)oc1c3n4c5c(oc6cc(-c7ccccc7)c(C)cc6n-5c(=O)n2-3)B(c2c(C)cccc2C)c2cc(C(C)(C)C)cc(c2-4)B1c1c(C)cccc1C]
109
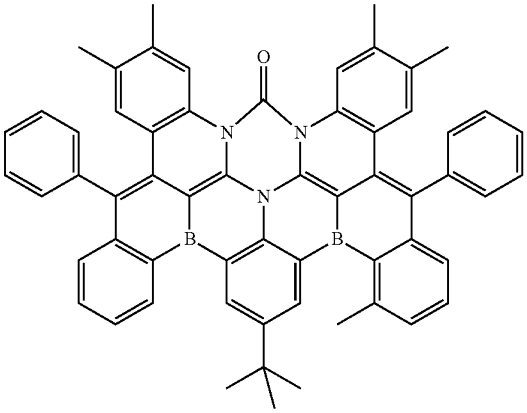 [SMILES: Cc1cc2c(cc1C)N1C(=O)N3C4=C5B(c6cc(C(C)(C)C)cc7c6N4C1=C1B7c4ccccc4C(c4ccccc4)=C12)c1c(C)cccc1C(c1ccccc1)=C5c1cc(C)c(C)cc13]
110

-continued
111
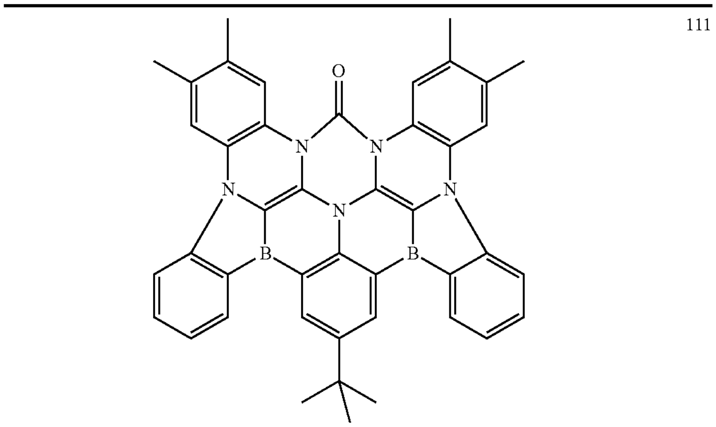
112
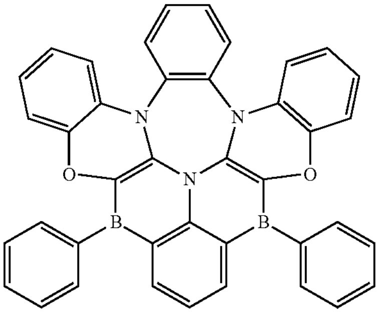 [SMILES: c1ccc(B2C3=c4n5c6n(c7ccccc7n4-c4ccccc4O3)-c3ccccc3OC=6B(c3ccccc3)c3cccc2c3-5)cc1]
113
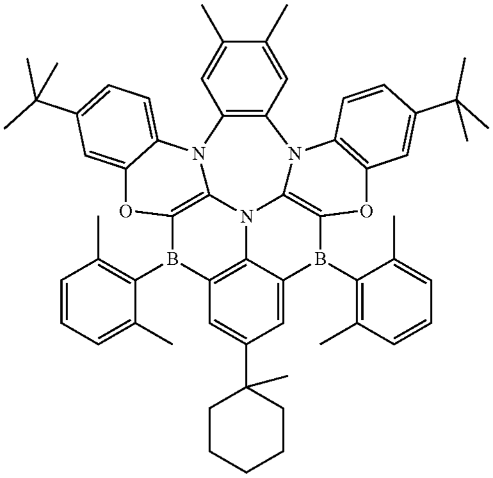 [SMILES: Cc1cc2c(cc1C)n1c3n4c5n2-c2ccc(C(C)(C)C)cc2OC=5B(c2c(C)cccc2C)c2cc(C5(C)CCCCC5)cc(c2-4)B(c2c(C)cccc2C)C=3Oc2cc(C(C)(C)C)ccc2-1]
114
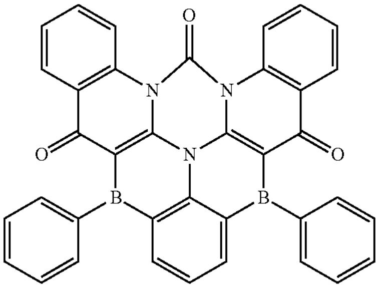 [SMILES: O=c1c2c3n4c5c(c(=O)c6ccccc6n5c(=O)n3c3ccccc13)B(c1ccccc1)c1cccc(c1-4)B2c1ccccc1]

-continued
115
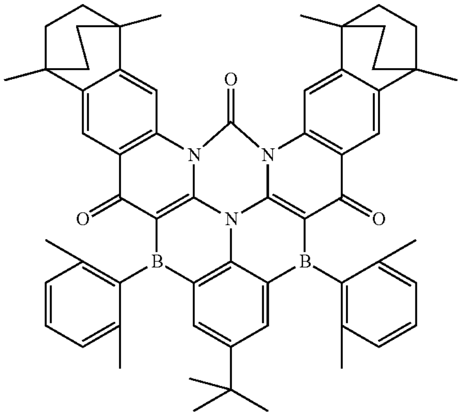
116
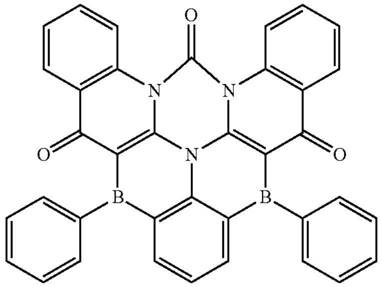 [SMILES: O=c1c2c3n4c5c(c(=O)c6ccccc6n5c(=O)n3c3ccccc13)B(c1ccccc1)c1cccc(c1-4)B2c1ccccc1]
117
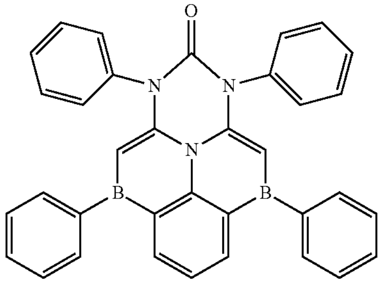 [SMILES: O=C1N(c2ccccc2)C2=CB(c3ccccc3)c3cccc4c3N2C(=CB4c2ccccc2)N1c1ccccc1]
118
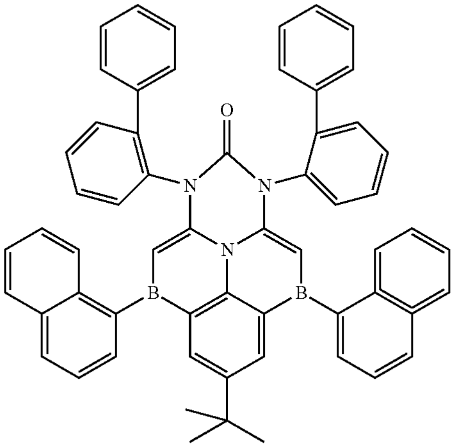

-continued
119
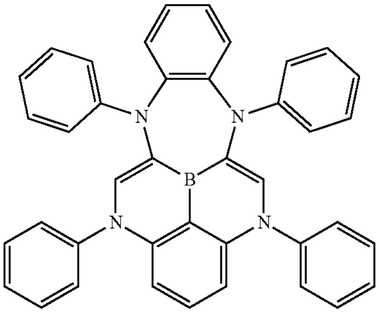 [SMILES: C1=C2B3C(=CN(c4ccccc4)c4cccc(c43)N1c1ccccc1)N(c1ccccc1)c1ccccc1N2c1ccccc1]
120
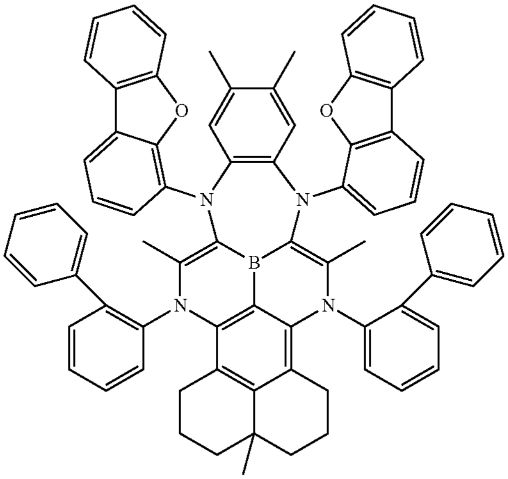 [SMILES: CC1=C2B3C(=C(C)N(c4ccccc4-c4ccccc4)c4c5c6c(c(c43)N1c1ccccc1-c1ccccc1)CCCC6(C)CCC5)N(c1cccc3c1oc1ccccc13)c1cc(C)c(C)cc1N2c1cccc2c1oc1ccccc12]
121
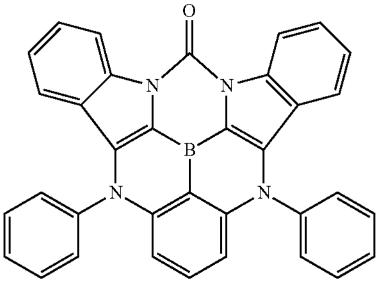 [SMILES: O=C1n2c3c(c4ccccc42)N(c2ccccc2)c2cccc4c2B3c2c(c3ccccc3n21)N4c1ccccc1]
122
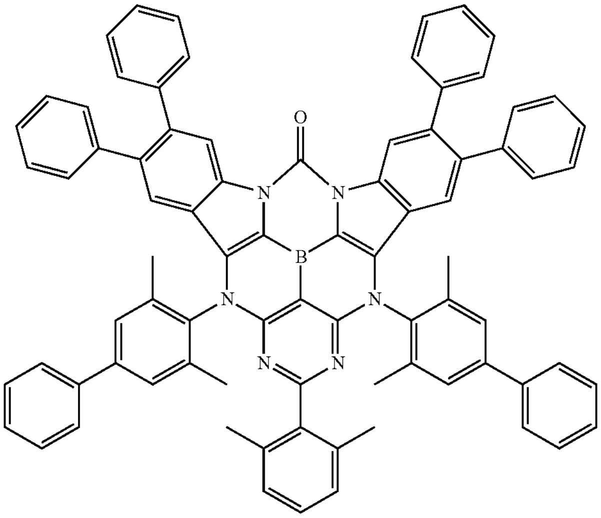 [SMILES: Cc1cccc(C)c1-c1nc2c3c(n1)N(c1c(C)cc(-c4ccccc4)cc1C)c1c4n(c5cc(-c6ccccc6)c(-c6ccccc6)cc15)C(=O)n1c(c(c5cc(-c6ccccc6)c(-c6ccccc6)cc51)N2c1c(C)cc(-c2ccccc2)cc1C)B34]

-continued
123
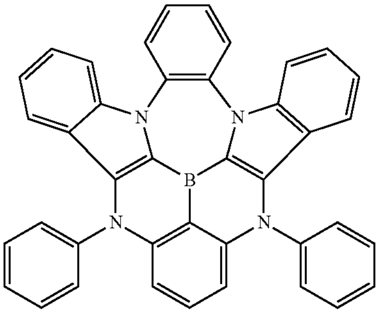 [SMILES: c1ccc(N2c3cccc4c3B3c5c2c2ccccc2n5-c2ccccc2-n2c3c(c3ccccc32)N4c2ccccc2)cc1]
124
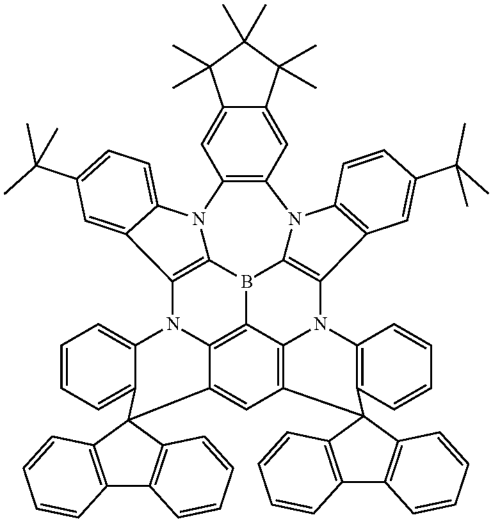 [SMILES: CC(C)(C)c1ccc2c(c1)c1c3n2-c2cc4c(cc2-n2c5c(c6cc(C(C)(C)C)ccc62)N2c6ccccc6C6(c7ccccc7-c7ccccc76)c6cc7c(c(c62)B35)N1c1ccccc1C71c2ccccc2-c2ccccc21)C(C)(C)C(C)(C)C4(C)C]
125
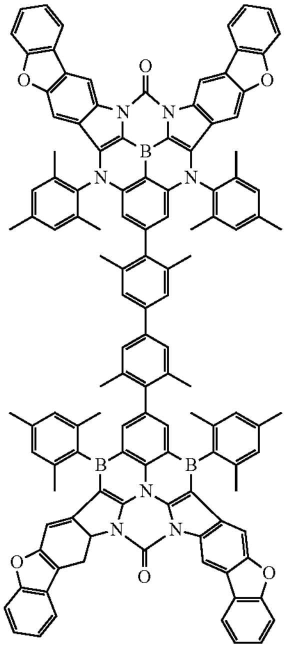 [SMILES: Cc1cc(C)c(B2C3=C4N5c6c2cc(-c2c(C)cc(-c7cc(C)c(-c8cc9c%10c(c8)N(c8c(C)cc(C)cc8C)c8c%11n(c%12cc%13c(cc8%12)oc8ccccc8%13)C(=O)n8c(c(c%12cc%13oc%14ccccc%14c%13cc%128)N9c8c(C)cc(C)cc8C)B%10%11)c(C)c7)cc2C)cc6B(c2c(C)cc(C)cc2C)c2c5n(c5cc6c(cc25)oc2ccccc26)C(=O)N4C2Cc4c(oc5ccccc45)C=C32)c(C)c1]

-continued

126

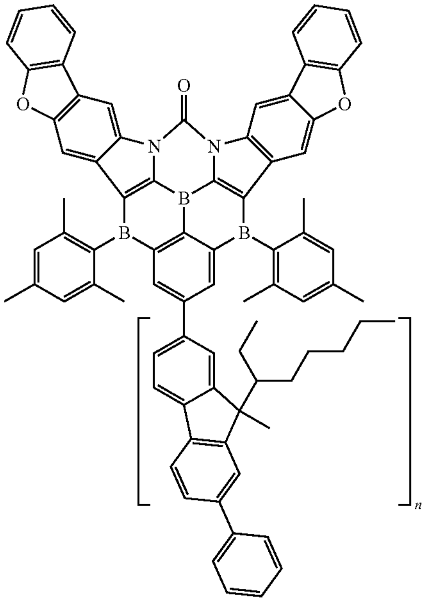

n = 1, 2, 3, 4, 5, 6, 7, 8, 9, 10

Preferred embodiments of compounds of the invention are recited in detail in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, in which a base skeleton having a Z group or a precursor of the Z group is synthesized, and at least one of the $Y^1$, $Y^2$, $Y^3$, $Y^4$ groups is introduced by means of a nucleophilic aromatic substitution reaction or a coupling reaction.

Suitable compounds comprising a base skeleton having a Z group are in many cases commercially available, and the starting compounds detailed in the examples are obtainable by known processes, and so reference is made thereto.

These compounds can be reacted with further compounds by known coupling reactions, the necessary conditions for this purpose being known to the person skilled in the art, and detailed specifications in the examples giving support to the person skilled in the art in conducting these reactions.

Particularly suitable and preferred coupling reactions which all lead to C—C bond formations and/or C—N bond formations are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The principles of the preparation processes detailed above are known in principle from the literature for similar compounds and can be adapted easily by the person skilled in the art for the preparation of the compounds of the invention. Further information can be found in the examples.

It is possible by these methods, if necessary followed by purification, for example recrystallization or sublimation, to obtain the compounds of the invention in high purity, preferably more than 99% (determined by means of $^1H$ NMR and/or HPLC).

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) and preferred embodiments of this formula or compounds of the invention, wherein one or more bonds of the compounds of the invention or of the structures of the formula (I) and preferred embodiments of that formula to the polymer, oligomer or dendrimer are present. According to the linkage of the structures of the formula (I) and preferred embodiments of this formula or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of the invention and at least one further compound. The further compound may, for example, be a solvent, especially one of the abovementioned solvents or a mixture of these solvents. If the further compound comprises a solvent, this mixture is referred to herein as formulation. The further compound may alternatively be at least one further organic or inorganic compound which is likewise used in the electronic device, for example an emitter and/or a matrix material, where these compounds differ from the compounds of the invention. Suitable emitters and matrix materials are listed at the back in connection with the organic electroluminescent device. The further compound may also be polymeric.

The present invention therefore still further provides a composition comprising a compound of the invention and at least one further organofunctional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide bandgap materials and n-dopants.

The present invention further provides for the use of a compound of the invention in an electronic device, especially in an organic electroluminescent device, preferably as emitter, more preferably as green, red or blue emitter. In this case, compounds of the invention preferably exhibit fluorescent properties and thus provide preferentially fluorescent emitters. In addition, compounds of the invention may as host materials, electron transport materials and/or hole conductor materials. It is especially possible here to use compounds of the invention in which many, preferably all, of the Z, $Z^1$, $Z^2$, $Z^3$, $Z^4$ groups are N advantageously as hole conductor material. It is also especially possible in accordance with the invention to use compounds of the invention in which many, preferably all, of the Z, $Z^1$, $Z^2$, $Z^3$, $Z^4$ groups are B advantageously as electron transport material. In addition, compounds of the invention may as a component in PCCs (pixel color converters) for conversion of light, in order, for example, to convert UV/deep blue to blue, green, yellow or red, or blue to green, yellow, red.

The present invention still further provides an electronic device comprising at least one compound of the invention. An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs, sOLED, PLEDs, LECs, etc.), preferably organic light-emitting diodes (OLEDs), organic light-emitting diodes based on small molecules (sOLEDs), organic light-emitting diodes based on polymers (PLEDs), light-emitting mechanical cells (LECs), organic laser diodes (O-laser), organic plasmon-emitting devices (D. M. Koller et al., *Nature Photonics* 2008, 1-4), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs) and organic electrical sensors, preferably organic electroluminescent devices ( ), more preferably organic light-emitting diodes (OLEDs), organic light-emitting diodes based on small molecules (sOLEDs), organic light-emitting diodes based on polymers (PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem electroluminescent device, especially for white-emitting OLEDs.

The compound of the invention may be used in different layers, according to the exact structure. Preference is given to an organic electroluminescent device comprising a compound of formula (I) or the above-detailed preferred embodiments in an emitting layer as emitter, preferably red, green or blue emitter.

When the compound of the invention is used as emitter in an emitting layer, preference is given to using a suitable matrix material which is known as such.

A preferred mixture of the compound of the invention and a matrix material contains between 99% and 1% by volume, preferably between 98% and 10% by volume, more preferably between 97% and 60% by volume and especially between 95% and 80% by volume of matrix material, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or biscarbazoles, for example according to JP 3139321 B2.

In addition, the co-host used may be a compound that does not take part in charge transport to a significant degree, if at all, as described, for example, in WO 2010/108579. Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

In a preferred configuration, a compound of the invention which is used as emitter is preferably used in combination with one or more phosphorescent materials (triplet emitters) and/or a compound which is a TADF (thermally activated delayed fluorescence) host material. Preference is given here to forming a hyperfluorescence and/or hyperphosphorescence system. Such hyperfluorescence and/or hyperphosphorescence systems form a preferred embodiment of a composition of the invention.

WO 2015/091716 A1 and WO 2016/193243 A1 disclose OLEDs containing both a phosphorescent compound and a fluorescent emitter in the emission layer, where the energy is transferred from the phosphorescent compound to the fluorescent emitter (hyperphosphorescence). In this context, the phosphorescent compound accordingly behaves as a host material. As the person skilled in the art knows, host materials have higher singlet and triplet energies as compared to the emitters in order that the energy from the host material can also be transferred to the emitter with maximum efficiency. The systems disclosed in the prior art have exactly such an energy relation.

Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/

104045, WO 2015/117718, WO 2016/015815, WO 2016/124304, WO 2017/032439, WO 2018/011186, WO 2018/001990, WO 2018/019687, WO 2018/019688, WO 2018/041769, WO 2018/054798, WO 2018/069196, WO 2018/069197, WO 2018/069273, WO 2018/178001, WO 2018/177981, WO 2019/020538, WO 2019/115423, WO 2019/158453 and WO 2019/179909. In general, all phosphorescent complexes as used for phosphorescent electroluminescent devices according to the prior art and as known to those skilled in the art in the field of organic electroluminescence are suitable, and the person skilled in the art will be able to use further phosphorescent complexes without exercising inventive skill.

A compound of the invention may preferably be used in combination with a TADF host material and/or a TADF emitter, as set out above.

The process referred to as thermally activated delayed fluorescence (TADF) is described, for example, by B. H. Uoyama et al., Nature 2012, Vol. 492, 234. In order to enable this process, a comparatively small singlet-triplet separation $\Delta E(S_1-T_1)$ of less than about 2000 $cm^{-1}$, for example, is needed in the emitter. In order to open up the $T^1 \rightarrow S_1$ transition which is spin-forbidden in principle, as well as the emitter, it is possible to provide a further compound in the matrix that has strong spin-orbit coupling, such that intersystem crossing is enabled via the spatial proximity and the interaction which is thus possible between the molecules, or the spin-orbit coupling is generated by means of a metal atom present in the emitter.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

Also preferred is an organic electroluminescent device is an organic electroluminescent device comprising a compound of formula (I) or the above-detailed preferred embodiments in a hole-conducting layer as hole conductor material. Preference is given here especially to compounds in which Z is N and at least one, preferably two, of the $Y^1$, $Y^2$ groups is/are N(Ar) or N(R), preferably N(Ar). In addition, preference is given here especially to compounds in which Z is N and at least one, preferably two, of the $Y^3$, $Y^4$ groups is/are N(Ar), N(R), P(Ar), P(R), O, S or Se, preferably N(Ar), N(R), O or S, more preferably N(Ar). Further preferred configurations of compounds of the invention that are suitable as hole conductor material are set out above, and so reference is made thereto.

Also preferred is an organic electroluminescent device comprising a compound of formula (I) or the above-detailed preferred embodiments in an electron-conducting layer as electron transport material. Preference is given here especially to compounds in which Z is B and at least one, preferably two, of the $Y^1$, $Y^2$ groups is/are B(Ar), B(R), Al(Ar), or Al(R), preferably B(Ar) or B(R). In addition, preference is given here especially to compounds in which Z is B and at least one, preferably two, of the $Y^3$, $Y^4$ groups represent(s) B(Ar), B(R), Al(Ar), Al(R), Ga(Ar), Ga(R), P(=O)Ar, P(=O)R, C=O, S=O or $SO_2$, preferably C=O, B(Ar), B(R), P(=O)Ar, P(=O)R, S=O or $SO_2$, more preferably C=O, B(R) or B(Ar). Further preferred configurations of compounds of the invention that are suitable as electron transport are set out above, and so reference is made thereto.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (I) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-8}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

Formulations for applying a compound of formula (I) or the preferred embodiments thereof detailed above are novel. The present invention therefore further provides formulations containing at least one solvent and a compound according to formula (I) or the preferred embodiments thereof detailed above.

In addition, hybrid methods are possible, in which, for example, one or more layers are applied from solution and one or more further layers are applied by vapor deposition.

Those skilled in the art are generally aware of these methods and are able to apply them without exercising inventive skill to organic electroluminescent devices comprising the compounds of the invention.

The compounds of the invention and the organic electroluminescent devices of the invention have the particular feature of an improved lifetime over the prior art. At the same time, the further electronic properties of the electroluminescent devices, such as efficiency or operating voltage, remain at least equally good. In a further variant, the compounds of the invention and the organic electroluminescent devices of the invention especially feature improved efficiency and/or operating voltage and higher lifetime compared to the prior art.

The electronic devices of the invention, especially organic electroluminescent devices, are notable for one or more of the following surprising advantages over the prior art:

1. Electronic devices, especially organic electroluminescent devices, comprising compounds of formula (I) or the preferred embodiments as emitters that have been recited above and hereinafter, have emission in the blue, green and yellow region of the color spectrum.

2. Electronic devices, especially organic electroluminescent devices, comprising compounds of formula (I) or the preferred embodiments recited above and hereinafter, especially as emitter, as hole conductor material and/or as electron transport material, have a very good lifetime. In this context, these compounds especially bring about low roll-off, i.e. a small drop in power efficiency of the device at high luminances.
3. Electronic devices, especially organic electroluminescent devices, comprising compounds of formula (I) or the preferred embodiments that have been recited above and hereinafter, have excellent efficiency as emitter, as hole conductor material and/or as electron transport material. In this context, compounds of the invention having structures of formula (I) or the preferred embodiments recited above and hereinafter bring about a low operating voltage when used in electronic devices.
4. The inventive compounds of formula (I) or the preferred embodiments recited above and hereinafter exhibit very high stability and lifetime.
5. With compounds of formula (I) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
6. Compounds of formula (I) or the preferred embodiments recited above and hereinafter have excellent glass film formation.
7. Compounds of formula (I) or the preferred embodiments recited above and hereinafter form very good films from solutions and show excellent solubility.

These abovementioned advantages are not accompanied by an inordinately high deterioration in the further electronic properties.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can have multiple enantiomeric, diastereomeric or tautomeric forms, one form is shown in a representative manner.

Synthesis of Synthons S

Example S1

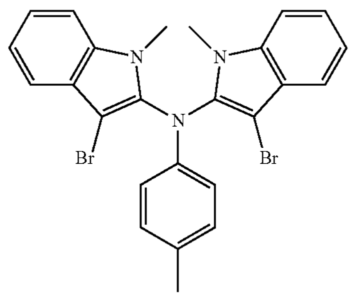 [SMILES: Cc1ccc(N(c2c(Br)c3ccccc3n2C)c2c(Br)c3ccccc3n2C)cc1]

Complete procedure including workup under protective gas and exclusion of light. To a well-stirred solution, cooled to 0° C., of 36.6 g (100 mmol) of N,N-bis-(1-methyl-2-indolyl)-4-methylaniline [415975-13-2] in 300 ml of dichloromethane is added, in portions of the course of 60 min, 35.6 g (200 mmol) of N-bromosuccinimide, and the mixture is then stirred at 0° C. for 5 h. The precipitated succinimide is filtered off, and the organic phase is washed three times with 200 g of ice-water and once with saturated sodium chloride solution, and dried over magnesium sulfate.

The desiccant is filtered off, the filtrate is concentrated to dryness and the residue is subjected to extraction by stirring with 150 ml of methanol. Yield: 35.2 g (67 mmol) 67%; purity about 95% by $^{1}H$ NMR.

The following compounds can be prepared analogously:

| Ex.. | Reactants | Product | Yield |
|---|---|---|---|
| S2 | 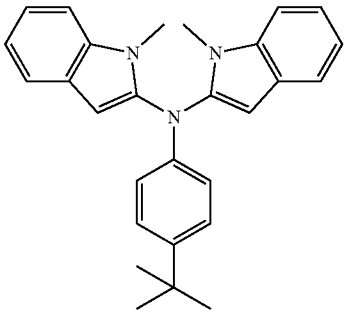 Preparation according to KR 2016077940 from 769-92-6 | 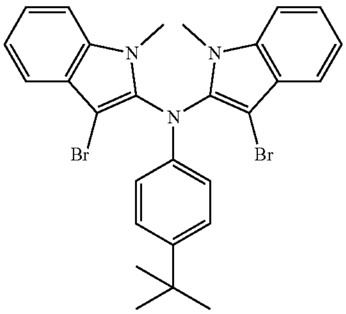 [SMILES: Cn1c(N(c2ccc(C(C)(C)C)cc2)c2c(Br)c3ccccc3n2C)c(Br)c2ccccc21] | 64% |
| S3 | 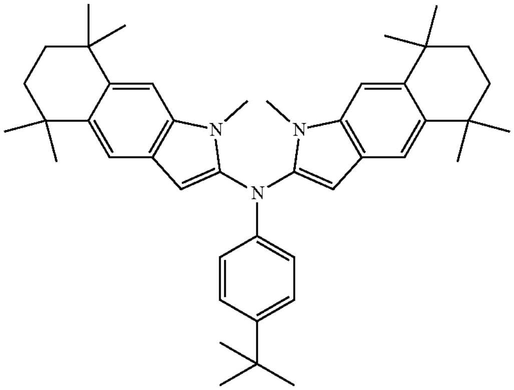 Preparation according to KR 2016077940 from 769-92-6 and 121866-11-3 | 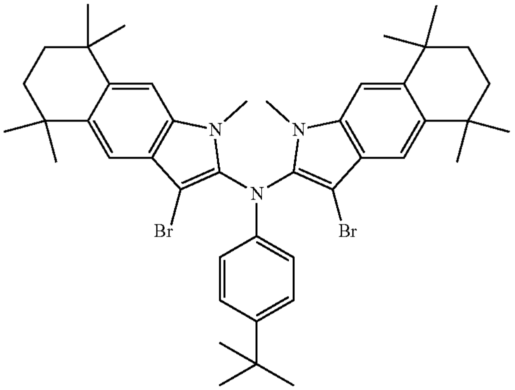 | 55% |

Example S100

Step 1: Lithiation of S1

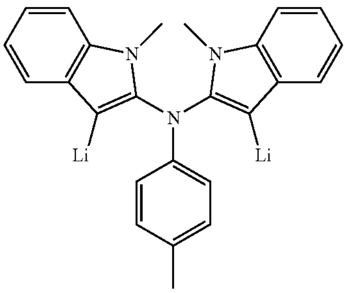

Intermediat, Nicht Isoliert

A baked-out, argon-inertized four-neck flask with magnetic stirrer bar, dropping funnel, water separator, reflux condenser and argon blanketing is charged with 26.2 g (50 mmol) of S1 in 1300 ml of tert-butylbenzene. The reaction mixture is cooled down to −40° C., and then 110.5 ml (210 mmol) of tert-butyllithium, 1.9 M in n-pentane, is added dropwise. The mixture is stirred at −40° C. for a further 30 min, allowed to warm up to room temperature, then heated 70° C., in the course of which the n-pentane is distilled off via the water separator over about 1 h.

Step 2: Transmetalation and Cyclization

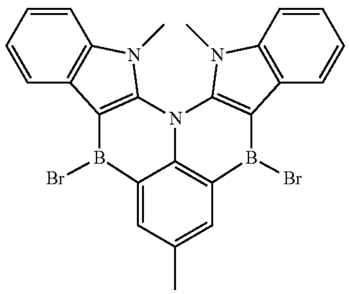 [SMILES: Cc1cc2c3c(c1)B(Br)c1c(n(C)c4ccccc14)N3c1c(c3ccccc3n1C)B2Br]

Intermediat, Nicht Isoliert

The reaction mixture is cooled back down to −40° C. 10.4 ml (110 mmol) of boron tribromide is added dropwise over a period of about 10 min. On completion of addition, the reaction mixture is stirred at RT for 1 h. Then the reaction mixture is cooled down to 0° C., and 19.2 ml (110 mmol) of di-iso-propylethylamine is added dropwise over a period of about 30 min. Then the reaction mixture is stirred at 160° C. for 12 h. After cooling, di-iso-propylethylammmonium hydrobromide is filtered off using a double-ended frit, and the filtrate is cooled down to −78° C.

Step 3: Arylatlon

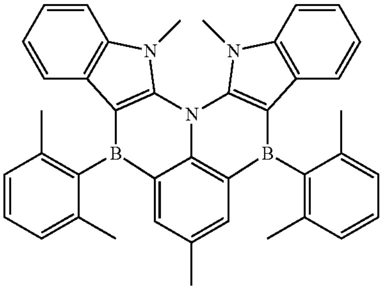 [SMILES: Cc1cc2c3c(c1)B(c1c(C)cccc1C)c1c(n(C)c4ccccc14)N3c1c(c3ccccc3n1C)B2c1c(C)cccc1C]

Intermediat, Nicht Isoliert

A second baked-out, argon-inertized Schlenk flask with magnetic stirrer bar is charged with 27.8 g (150 mmol) of 2-bromo-1,3-dimethylbenzene [576-22-7] in 1000 ml of diethyl ether and cooled down to −78° C. Then 60.0 ml (150 mmol) of n-butyllithium, 2.5 M in n-hexane, is added dropwise thereto and the mixture is stirred for a further 30 min. The reaction mixture is allowed to warm up to RT and stirred for a further 1 h, and the solvent is removed completely under reduced pressure. The lithium organyl is suspended in 300 ml of toluene and transferred into the cryogenic reaction mixture from step 2. The mixture is stirred for a further 1 h, and the reaction mixture is left to warm up to RT overnight. 15 ml of acetone is added cautiously to the reaction mixture, which is concentrated to dryness. The oily residue is absorbed with ECM onto ISOLUTE® and hot-filtered through a silica gel bed with an n-pentane-DCM mixture (10:1).

The filtrate is concentrated to dryness.

Step 4: Demethylaton to S100

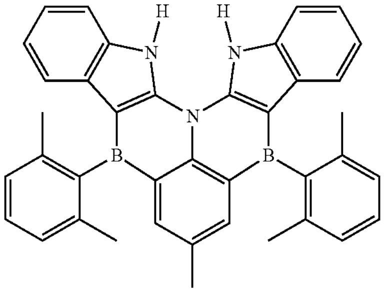 [SMILES: Cc1cc2c3c(c1)B(c1c(C)cccc1C)c1c([nH]c4ccccc14)N3c1[nH]c3ccccc3c1B2c1c(C)cccc1C]

Procedure as per the process described by T. Rosenau et al., Org. Lett., 2006, 6(4), 541. The product from step 3 is divided into 4 portions and converted, residence time in the reactive zone 10 min., the combined eluates are finally extracted by stirring from ethanol. Yield over 4 stages: 5.1 g (9 mmol), 18%: Purity: about 95% by $^{1}$H NMR.

The following compounds can be prepared analogously:

| Ex. | Reactant | Products | Yield |
|---|---|---|---|
| S101 | S2 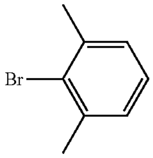 576-22-7 | 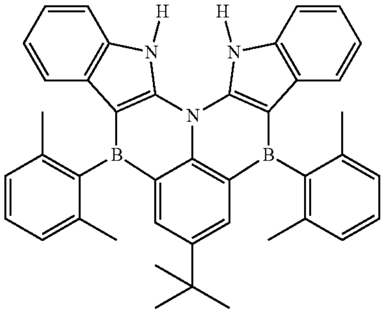 [SMILES: Cc1cccc(C)c1B1c2cc(C(C)(C)C)cc3c2N(c2[nH]c4ccccc4c21)c1[nH]c2ccccc2c1B3c1c(C)cccc1C] | 22% |
| S102 | S2 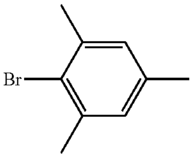 576-83-0 | 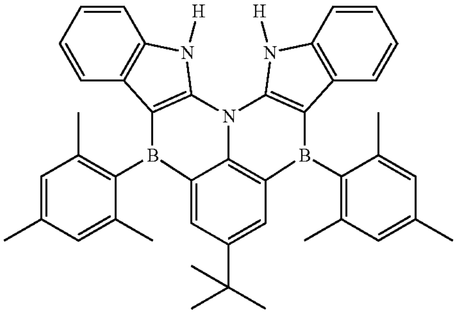 | 23% |

-continued
| Ex. | Reactant | Products | Yield |
| --- | --- | --- | --- |
| S103 | S2 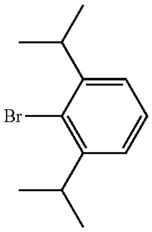 57190-17-7 | 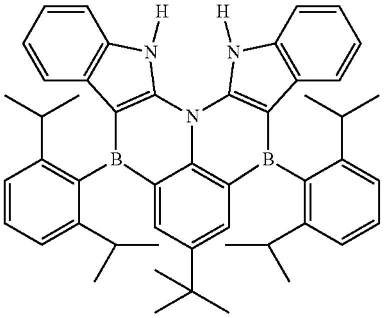 [SMILES: CC(C)c1cccc(C(C)C)c1B1c2cc(C(C)(C)C)cc3c2N(c2[nH]c4ccccc4c21)c1[nH]c2ccccc2c1B3c1c(C(C)C)cccc1C(C)C] | 26% |
| S104 | S2 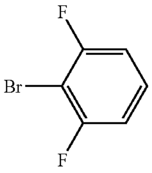 64248-56-2 | 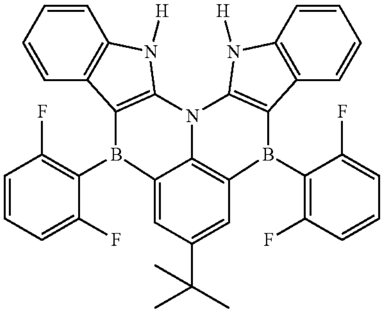 [SMILES: CC(C)(C)c1cc2c3c(c1)B(c1c(F)cccc1F)c1c([nH]c4ccccc14)N3c1[nH]c3ccccc3c1B2c1c(F)cccc1F] | 20% |
| S105 | S2 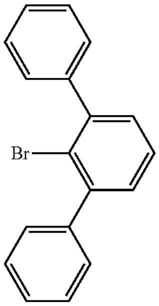 126866-29-3 | 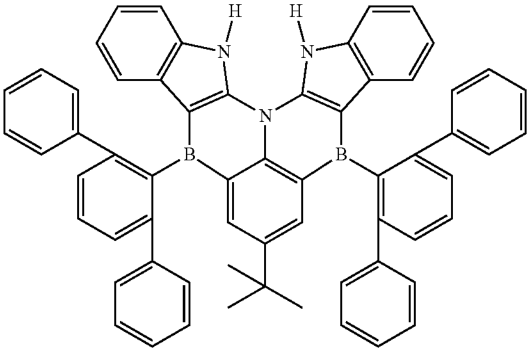 [SMILES: CC(C)(C)c1cc2c3c(c1)B(c1c(-c4ccccc4)cccc1-c1ccccc1)c1c([nH]c4ccccc14)N3c1[nH]c3ccccc3c1B2c1c(-c2ccccc2)cccc1-c1ccccc1] | 27% |
| S106 | S2 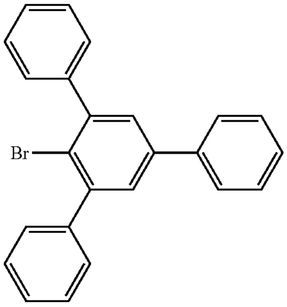 10368-73-7 | 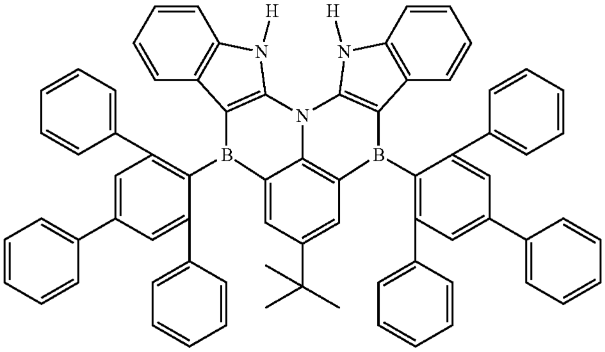 [SMILES: CC(C)(C)c1cc2c3c(c1)B(c1c(-c4ccccc4)cc(-c4ccccc4)cc1-c1ccccc1)c1c([nH]c4ccccc14)N3c1[nH]c3ccccc3c1B2c1c(-c2ccccc2)cc(-c2ccccc2)cc1-c1ccccc1] | 25% |

-continued
| Ex. | Reactant | Products | Yield |
|---|---|---|---|
| S107 | S2 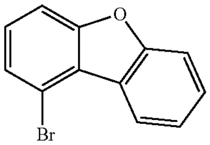 50548-45-3 | 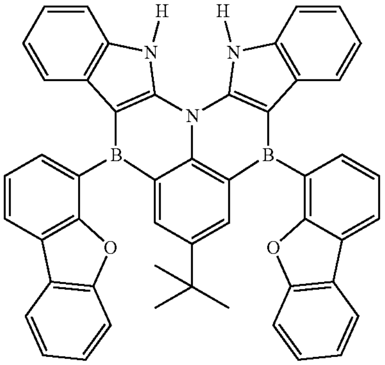 [SMILES: CC(C)(C)c1cc2c3c(c1)B(c1cccc4c1oc1ccccc14)c1c([nH]c4ccccc14)N3c1[nH]c3ccccc3c1B2c1cccc2c1oc1ccccc12] | 21% |
| S108 | S2 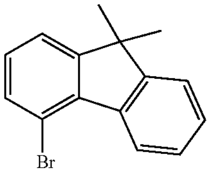 942615-32-9 | 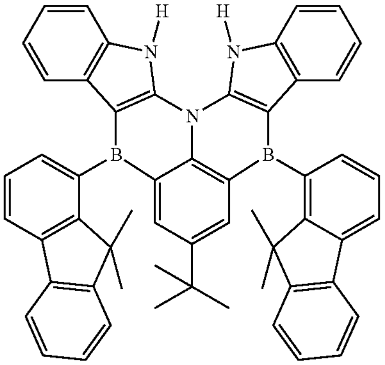 [SMILES: CC(C)(C)c1cc2c3c(c1)B(c1cccc4c1C(C)(C)c1ccccc1-4)c1c([nH]c4ccccc14)N3c1[nH]c3ccccc3c1B2c1cccc2c1C(C)(C)c1ccccc1-2] | 20% |
| S109 | S3 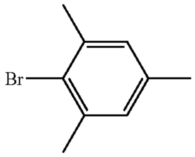 576-83-0 | 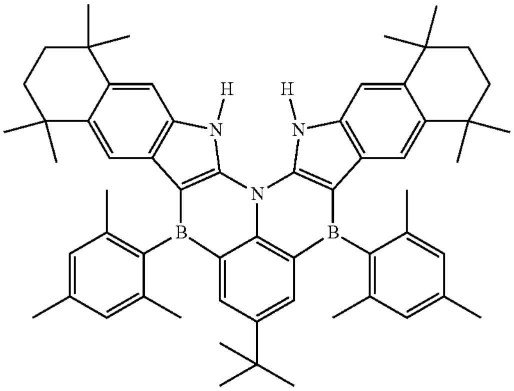 | 22% |
| S110 | Steps 1, 2 & 4 S2 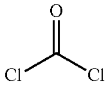 75-44-5 1M in toluene | 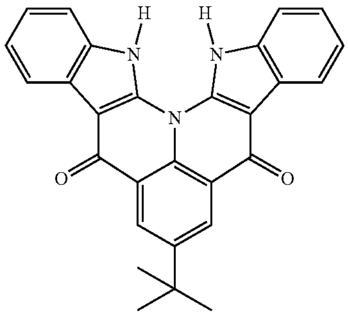 [SMILES: CC(C)(C)c1cc2c(=O)c3c4ccccc4[nH]c3n3c4[nH]c5ccccc5c4c(=O)c(c1)c23] | 30% |

-continued
| Ex. | Reactant | Products | Yield |
|---|---|---|---|
| S111 | Steps 1, 2 & 4<br>S2<br>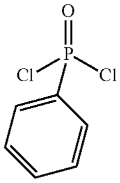<br>824-72-6 | 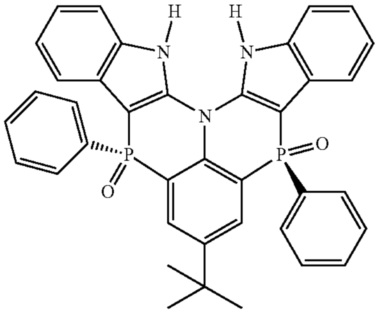<br>Racemate | 25% |
| S112 | Steps 1, 2 & 4<br>S2<br>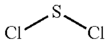<br>10545-99-0 | 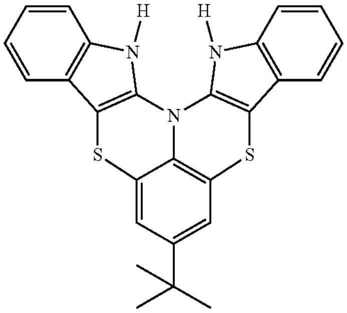 [SMILES: CC(C)(C)c1cc2c3c(c1)Sc1c([nH]c4ccccc14)N3c1[nH]c3ccccc3c1S2] | 17% |
| S113 | Steps 1, 2 & 4<br>S2<br>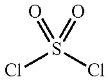<br>7791-25-5 | 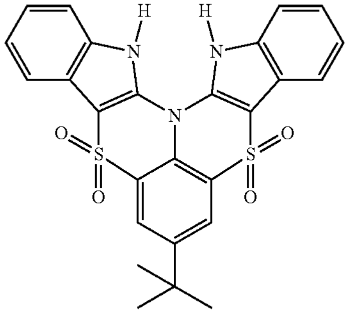 [SMILES: CC(C)(C)c1cc2c3c(c1)S(=O)(=O)c1c([nH]c4ccccc14)N3c1[nH]c3ccccc3c1S2(=O)=O] | 24% |
| S114 | Steps 1, 2 & 4<br>S2<br>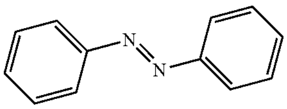<br>103-33-3 | 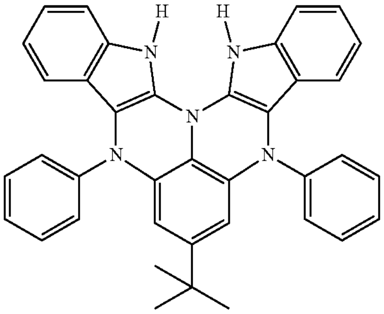 [SMILES: CC(C)(C)c1cc2c3c(c1)N(c1ccccc1)c1c([nH]c4ccccc14)N3c1[nH]c3ccccc3c1N2c1ccccc1] | 8% |

-continued

| Ex. | Reactant | Products | Yield |
|---|---|---|---|
| S115 | Steps 1, 2 & 4<br>S2<br>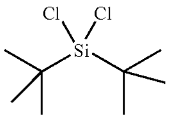<br>18395-90-9 | 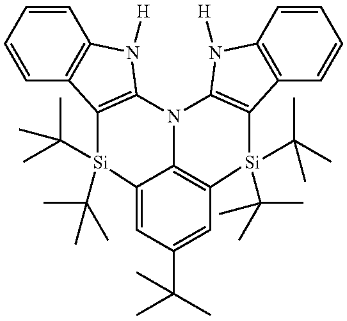 [SMILES: CC(C)(C)c1cc2c3c(c1)[Si](C(C)(C)C)(C(C)(C)C)c1c([nH]c4ccccc14)N3c1[nH]c3ccccc3c1[Si]2(C(C)(C)C)C(C)(C)C] | 25% |
| S116 | Steps 1, 2 & 4<br>S2<br>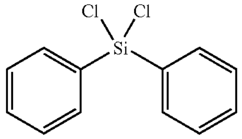<br>80-10-4 | 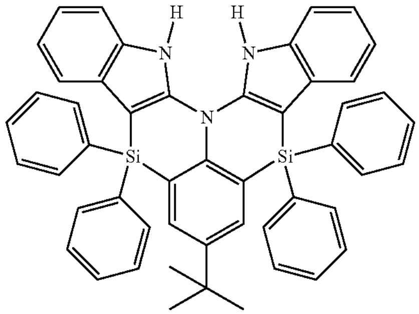 [SMILES: CC(C)(C)c1cc2c3c(c1)[Si](c1ccccc1)(c1ccccc1)c1c([nH]c4ccccc14)N3c1[nH]c3ccccc3c1[Si]2(c1ccccc1)c1ccccc1] | 27% |

Example D100

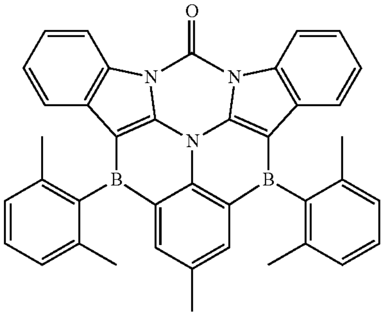 [SMILES: Cc1cc2c3c(c1)B(c1c(C)cccc1C)c1c4ccccc4n4c(=O)n5c6ccccc6c(c5n-3c14)B2c1c(C)cccc1C]

To a solution of 5.65 g (10.0 mmol) of S100 in 200 ml of THF is added in portions, with good stirring and ice cooling, 4.8 g (20.0 mmol) of sodium hydride, and then the mixture is stirred for 1 h. 10.0 ml (10.0 mmol) of a phosgene solution (1 M in toluene) is added dropwise, the mixture is stirred for 1 h, and then the solvent is removed under reduced pressure. The residue is subjected to sublimation under high vacuum (p about $10^{-4}$ mbar, T 250-300° C.), with sublimation of the product to leave the salts. The sublimate is fractionally sublimed again. Yield: 1.66 g (2.8 mmol) 28%; purity about 99.9% by $^{1}H$ NMR.

The following compounds can be prepared analogously:

| Ex.. | Reactants | Product | Yield |
|---|---|---|---|
| D101 | S101<br>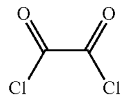<br>79-37-8 | 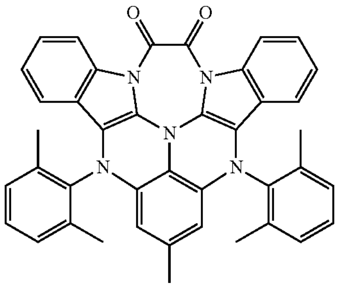 [SMILES: Cc1cc2c3c(c1)n(-c1c(C)cccc1C)c1c4ccccc4n4c(=O)c(=O)n5c6ccccc6c(c5n3c14)n2-c1c(C)cccc1C] | 46% |

Example D200

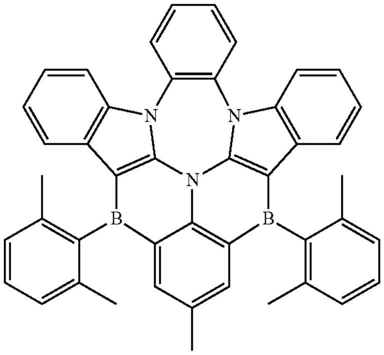 [SMILES: Cc1cc2c3c(c1)B(c1c(C)cccc1C)c1c4ccccc4n4c5ccccc5n5c6ccccc6c(c5n-3c14)B2c1c(C)cccc1C]

A mixture of 5.65 g (10.0 mmol) of D100, 2.83 g (12.0 mmol) of 1,2-dibromobenzene [583-53-9], 2.88 g (30.0 mmol) of sodium tert-butoxide, 48.6 mg (0.24 mmol) of tri-tert tributylphosphine, 44.9 mg (0.20 mmol) of palladium (II) acetate and 70 ml of o-xylene is stirred under reflux for 16 h. The mixture is left to cool to 50° C., 100 ml of water and 200 ml of ethyl acetate are added, and the organic phase is separated off and washed three times with 100 ml each time of water and twice with 100 ml of saturated sodium chloride solution and dried over magnesium sulfate. The desiccant is filtered off using a Celite bed in the form of an ethyl acetate slurry, the filtrate is concentrated to dryness and the residue is subjected to hot extraction with ethanol. Further purification is effected by flash chromatography (Torrent automated column system from A. Semrau, ethyl acetate/n-heptane gradient), by repeated hot extraction crystallization (dichloromethane/acetonitrile (1:2 vv)) and final fractional sublimation or heat treatment under high vacuum. Yield: 2.83 g (4.4 mmol) 44%; purity about 99.9% by $^{1}H$ NMR.

The following compounds can be prepared analogously:

| Ex.. | Reactants | Product | Yield |
|---|---|---|---|
| D201 | S101<br>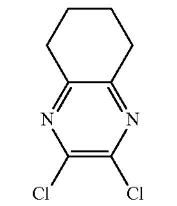<br>1135213-57-8 | 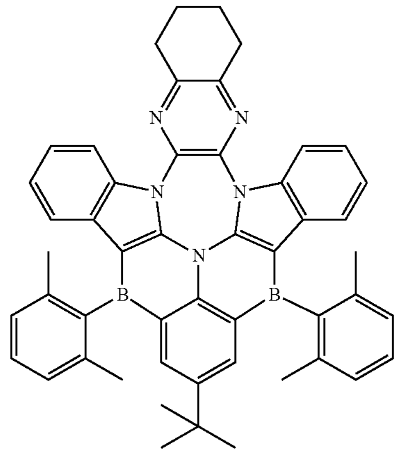 [SMILES: Cc1cccc(C)c1B1c2cc(C(C)(C)C)cc3c2-n2c4c1c1ccccc1n4c1nc4c(nc1n1c5ccccc5c(c21)B3c1c(C)cccc1C)CCCC4] | 55% |
| D202 | S101<br>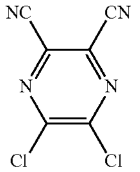<br>56413-95-7 | 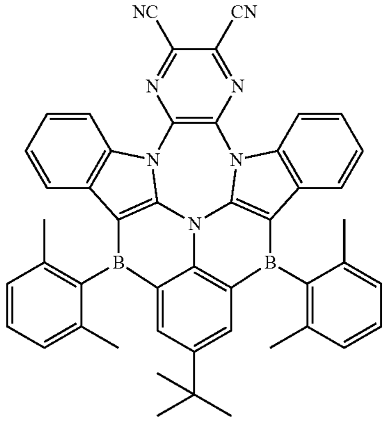 [SMILES: Cc1cccc(C)c1B1c2cc(C(C)(C)C)cc3c2-n2c4c1c1ccccc1n4c1nc(C#N)c(C#N)nc1n1c4ccccc4c(c21)B3c1c(C)cccc1C] | 51% |
| D203 | S101<br>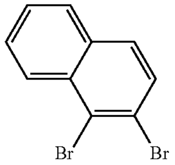<br>5438-13-1 | 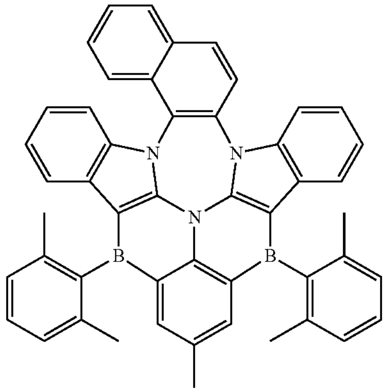 [SMILES: Cc1cc2c3c(c1)B(c1c(C)cccc1C)c1c4ccccc4n4c5c6ccccc6ccc5n5c6ccccc6c(c5n-3c14)B2c1c(C)cccc1C] | 32% |

-continued
| Ex.. | Reactants | Product | Yield |
|---|---|---|---|
| D204 | S101 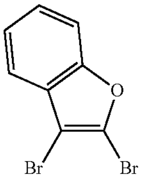 64150-61-4 | 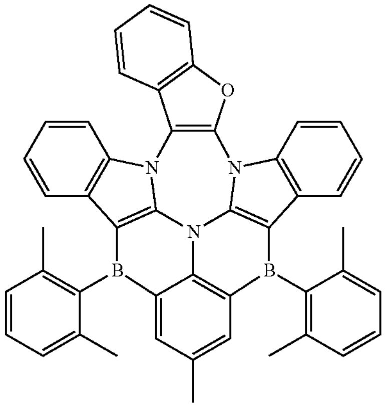 [SMILES: Cc1cc2c3c(c1)B(c1c(C)cccc1C)c1c4ccccc4n4c5c6ccccc6oc5n5c6ccccc6c(c5n-3c14)B2c1c(C)cccc1C] | 36% |
| D205 | S101 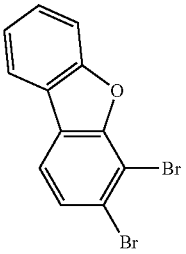 617707-32-1 | 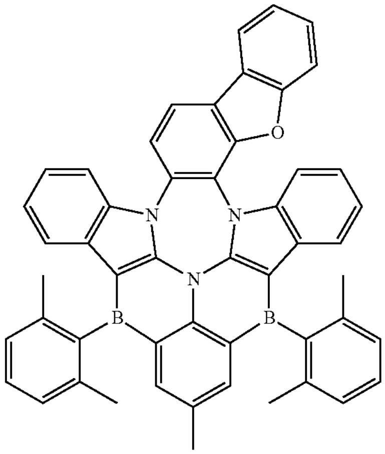 [SMILES: Cc1cc2c3c(c1)B(c1c(C)cccc1C)c1c4ccccc4n4c5c6oc7ccccc7c6ccc5n5c6ccccc6c(c5n-3c14)B2c1c(C)cccc1C] | 30% |
| D206 | S101 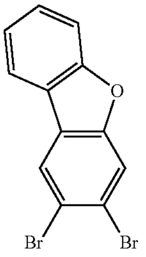 617707-30-9 | 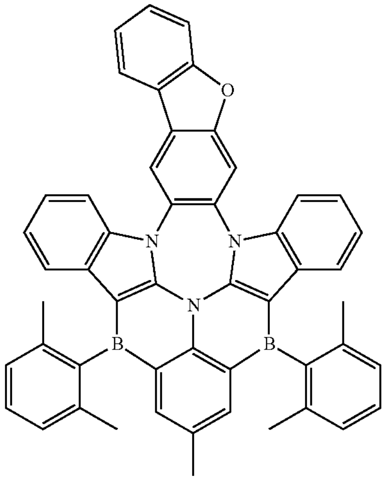 [SMILES: Cc1cc2c3c(c1)B(c1c(C)cccc1C)c1c4ccccc4n4c5cc6c(cc5n5c7ccccc7c(c5n-3c14)B2c1c(C)cccc1C)oc1ccccc16] | 38% |

-continued
| Ex.. | Reactants | Product | Yield |
| --- | --- | --- | --- |
| D207 | S101 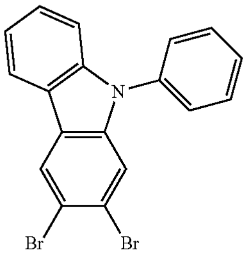 2375560-82-8 | 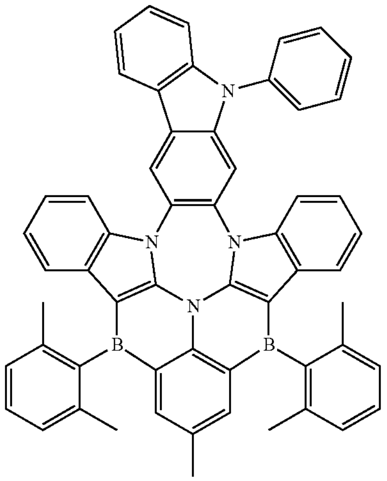 [SMILES: Cc1cc2c3c(c1)B(c1c(C)cccc1C)c1c4ccccc4n4c5cc6c(cc5n5c7ccccc7c(c5n-3c14)B2c1c(C)cccc1C)c1ccccc1n6-c1ccccc1] | 40% |
| D208 | S101 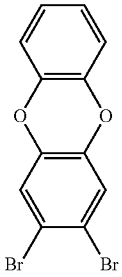 50585-37-0 | 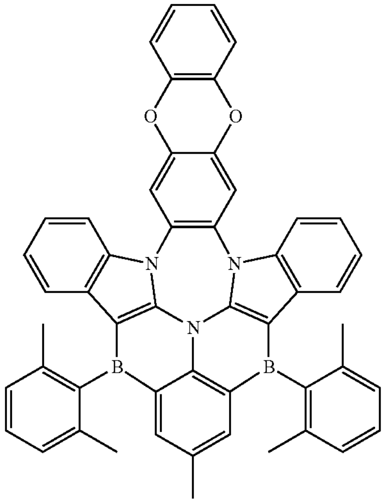 [SMILES: Cc1cc2c3c(c1)B(c1c(C)cccc1C)c1c4ccccc4n4c5cc6oc7ccccc7oc6cc5n5c6ccccc6c(c5n-3c14)B2c1c(C)cccc1C] | 45% |
| D209 | S102 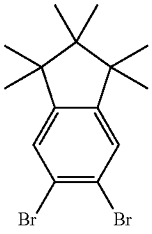 1541101-19-2 | 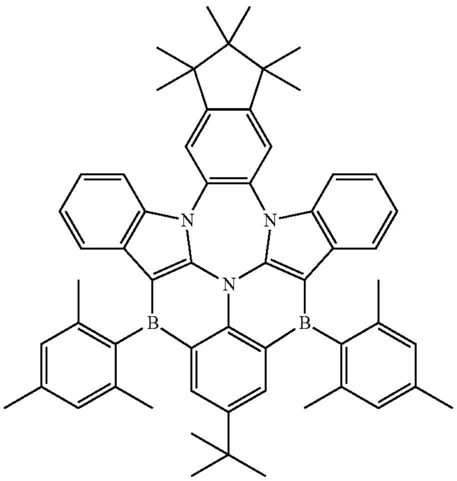 | 43% |

-continued
| Ex.. | Reactants | Product | Yield |
|---|---|---|---|
| D210 | S103<br>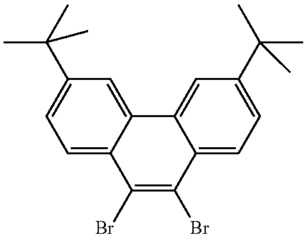<br>2265893-37-4 | 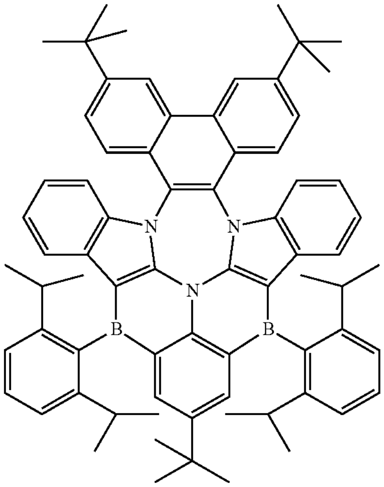 [SMILES: CC(C)c1cccc(C(C)C)c1B1c2cc(C(C)(C)C)cc3c2-n2c4c1c1ccccc1n4c1c4ccc(C(C)(C)C)cc4c4cc(C(C)(C)C)ccc4c1n1c4ccccc4c(c21)B3c1c(C(C)C)cccc1C(C)C] | 40% |
| D211 | S104<br>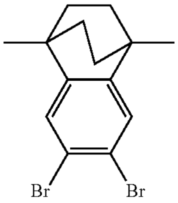<br>1801624-64-5 | 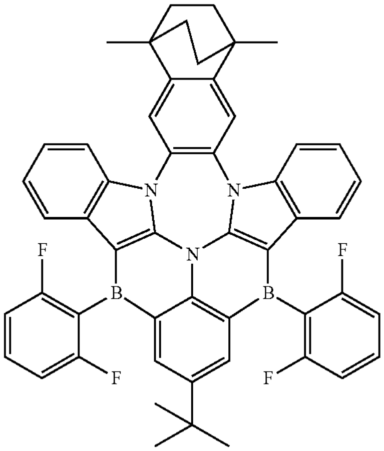 [SMILES: CC(C)(C)c1cc2c3c(c1)B(c1c(F)cccc1F)c1c4ccccc4n4c5cc6c(cc5n5c7ccccc7c(c5n-3c14)B2c1c(F)cccc1F)C1(C)CCC6(C)CC1] | 37% |
| D212 | S105<br>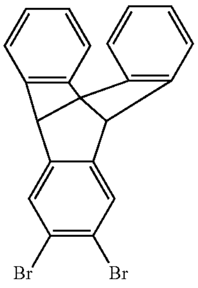<br>52776-05-3 | 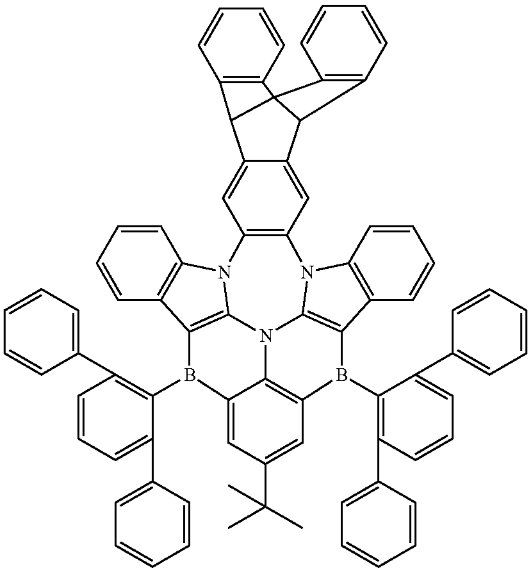 [SMILES: CC(C)(C)c1cc2c3c(c1)B(c1c(-c4ccccc4)cccc1-c1ccccc1)c1c4ccccc4n4c5cc6c(cc5n5c7ccccc7c(c5n-3c14)B2c1c(-c2ccccc2)cccc1-c1ccccc1)C1c2ccccc2C12c1ccccc1C62] | 39% |

-continued
| Ex.. | Reactants | Product | Yield |
| --- | --- | --- | --- |
| D213 | S106 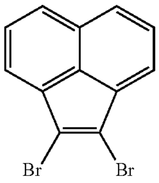 13019-33-5 | 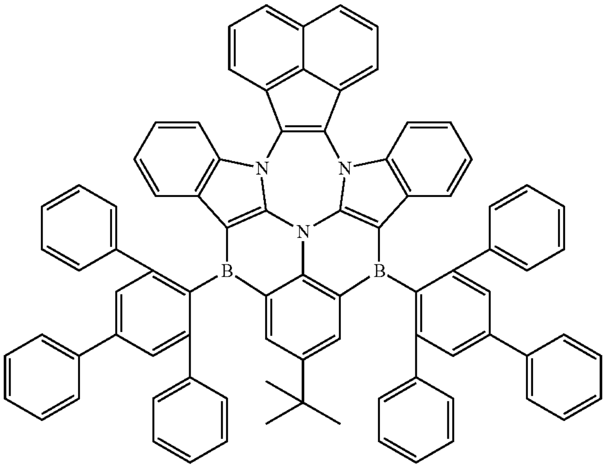 [SMILES: CC(C)(C)c1cc2c3c(c1)B(c1c(-c4ccccc4)cc(-c4ccccc4)cc1-c1ccccc1)c1c4ccccc4n4c5c6cccc7cccc(c76)c5n5c6ccccc6c(c5n-3c14)B2c1c(-c2ccccc2)cc(-c2ccccc2)cc1-c1ccccc1] | 33% |
| D214 | S107 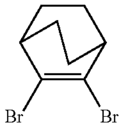 112439-97-1 | 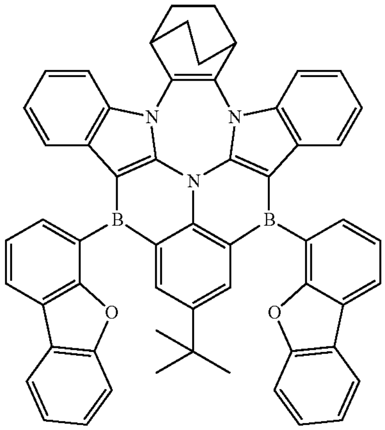 [SMILES: CC(C)(C)c1cc2c3c(c1)B(c1cccc4c1oc1ccccc14)c1c4ccccc4n4c5c(n6c7ccccc7c(c6n-3c14)B2c1cccc2c1oc1ccccc12)C1CCC5CC1] | 40% |
| D215 | S108 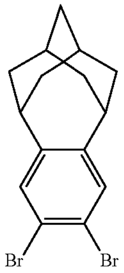 1801624-66-7 | 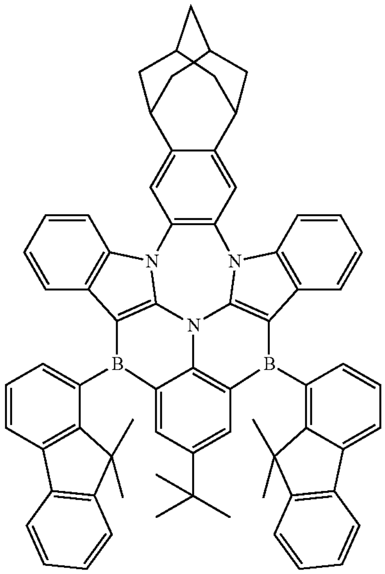 [SMILES: CC(C)(C)c1cc2c3c(c1)B(c1cccc4c1C(C)(C)c1ccccc1-4)c1c4ccccc4n4c5cc6c(cc5n5c7ccccc7c(c5n-3c14)B2c1cccc2c1C(C)(C)c1ccccc1-2)C1CC2CC3CC6CC23C1] | 38% |

-continued
| Ex.. | Reactants | Product | Yield |
|---|---|---|---|
| D216 | S109 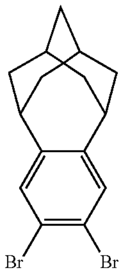 1801624-66-7 | 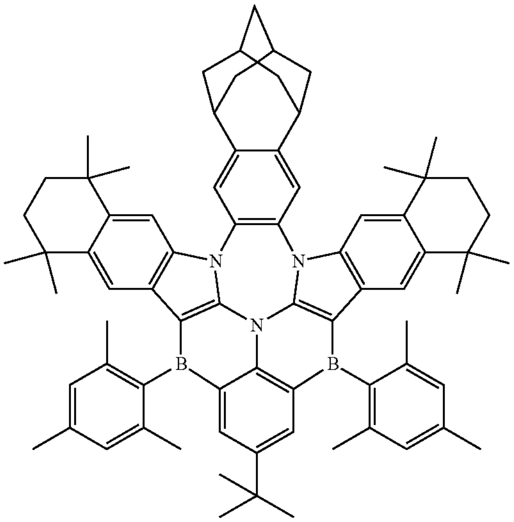 | 40% |
| D217 | S110 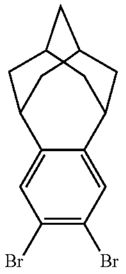 1801624-66-7 | 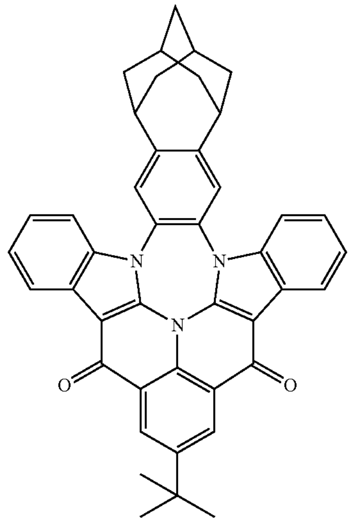 [SMILES: CC(C)(C)c1cc2c(=O)c3c4ccccc4n4c5cc6c(cc5n5c7ccccc7c7c(=O)c(c1)c2n(c34)c75)C1CC2CC3CC6CC32C1] | 40% |
| D218 | S111 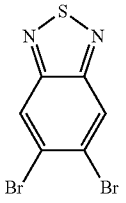 18392-81-9 | 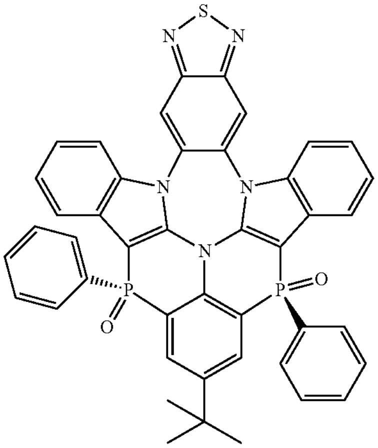 Racemate | 30% |

-continued
| Ex.. | Reactants | Product | Yield |
|---|---|---|---|
| D219 | S112<br>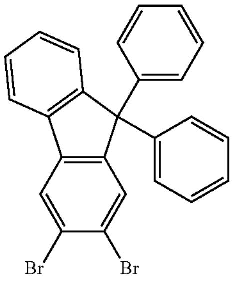<br>2174966-41-5 | 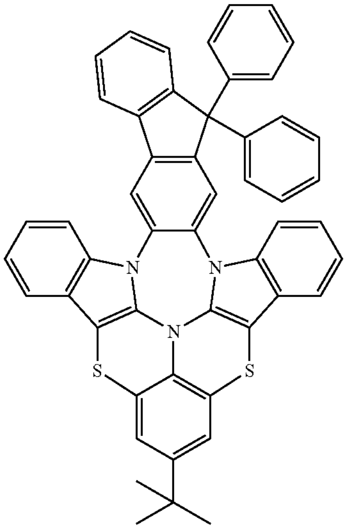 [SMILES: CC(C)(C)c1cc2sc3c4ccccc4n4c5cc6c(cc5n5c7ccccc7c7sc(c1)c2n(c34)c75)C(c1ccccc1)(c1ccccc1)c1ccccc1-6] | 37% |
| D220 | S113<br>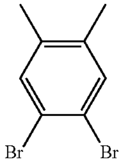<br>24932-48-7 | 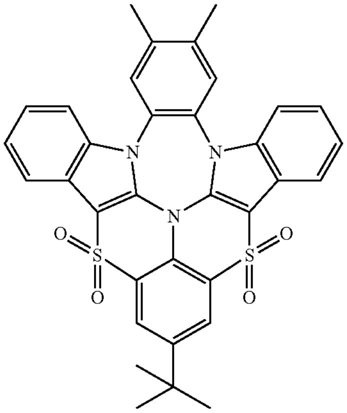 [SMILES: Cc1cc2c(cc1C)n1c3ccccc3c3c1n1c4c(c5ccccc5n24)S(=O)(=O)c2cc(C(C)(C)C)cc(c2-1)S3(=O)=O] | 42% |
| D221 | S114<br>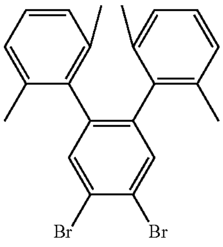<br>2135796-06-2 | 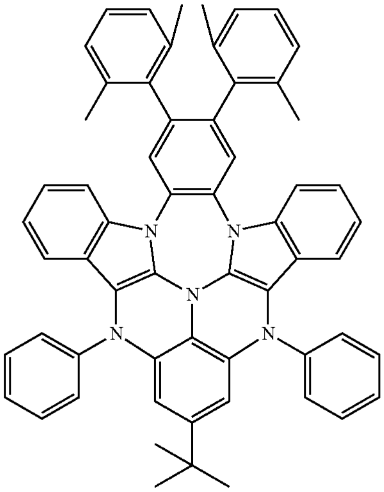 [SMILES: Cc1cccc(C)c1-c1cc2c(cc1-c1c(C)cccc1C)n1c3ccccc3c3c1n1c4c(cc(C(C)(C)C)cc4n3-c3ccccc3)n(-c3ccccc3)c3c4ccccc4n2c31] | 19% |

-continued
| Ex.. | Reactants | Product | Yield |
|---|---|---|---|
| S222 | S115 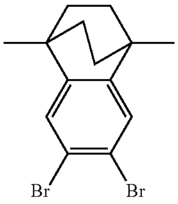 1801624-64-5 | 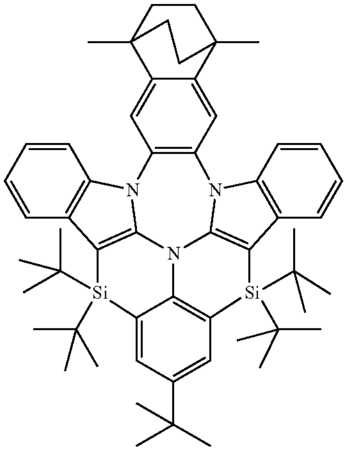 [SMILES: CC(C)(C)c1cc2c3c(c1)[Si](C(C)(C)C)(C(C)(C)C)c1c4ccccc4n4c5cc6c(cc5n5c7ccccc7c(c5n-3c14)[Si]2(C(C)(C)C)C(C)(C)C)C1(C)CCC6(C)CC1] | 42% |
| D223 | S116 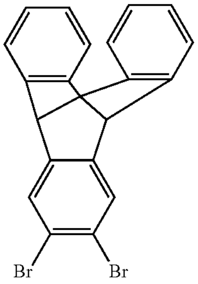 52776-05-3 | 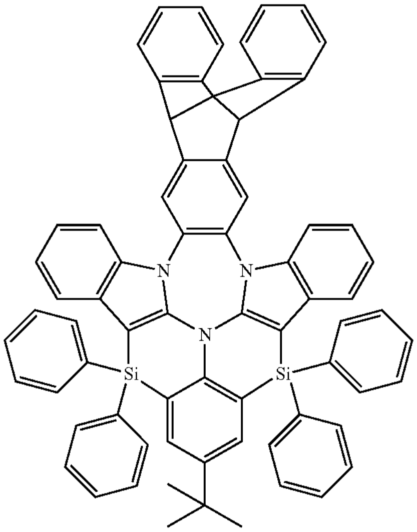 [SMILES: CC(C)(C)c1cc2c3c(c1)[Si](c1ccccc1)(c1ccccc1)c1c4ccccc4n4c5cc6c(cc5n5c7ccccc7c(c5n-3c14)[Si]2(c1ccccc1)c1ccccc1)C1c2ccccc2C12c1ccccc1C62] | 36% |
Example, Dopant D203P
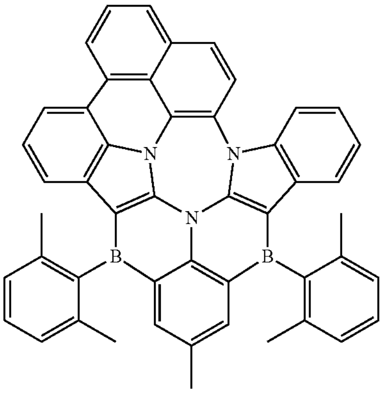 [SMILES: Cc1cc2c3c(c1)B(c1c(C)cccc1C)c1c4cccc5c6cccc7ccc8c(c76)n(c45)c1n-3c1c(c3ccccc3n81)B2c1c(C)cccc1C]
Preparation from D203 by flash vacuum pyrolysis, carrier gas: argon, reduced pressure about $10^{-2}$ torr, pyrolysis zone temperature 550° C., catalyst: 5% PdO on alumina. Chromatography separation, DCM/n-heptane, silica gel. Yield: 22%.
In an analogous manner, it is possible to prepare D204P from D204; yield: 16%.
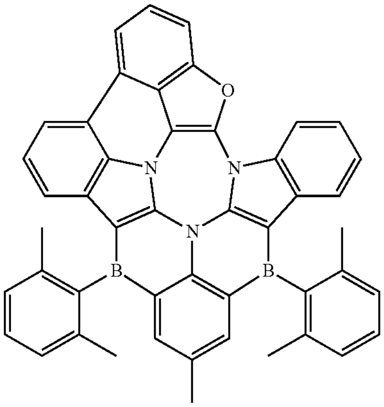 [SMILES: Cc1cc2c3c(c1)B(c1c(C)cccc1C)c1c4cccc5c6cccc7oc8c(c76)n(c45)c1n-3c1c(c3ccccc3n81)B2c1c(C)cccc1C]

Production of OLED Components

1) Vacuum-Processed Components

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plates (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly(styrenesulfonate), purchased as CLEVIOS™ P VP AI 4083 from Heraeus Precious Metals GmbH Germany, spun on from aqueous solution) and then baked at 180° C. for 10 min. These coated glass plates form the substrates to which the OLEDs are applied.

The OLEDs basically have the following layer structure: Substrate/hole injection layer 1 (HIL1) consisting of Ref-HTM1 doped with 5% NDP-9 (commercially available from Novaled), 20 nm/hole transport layer 1 (HTL1) composed of: 160 nm HTM1 for UV & blue OLEDs; 50 nm for green and yellow OLEDs; 110 nm for red OLEDs/hole transport layer 2 (HTL2) composed of: 10 nm for blue OLEDs; 20 nm for green & yellow OLEDs; 10 nm for red OLEDs/emission layer (EML): 25 nm for blue OLEDs; 40 nm for green & yellow OLEDs; 35 nm for red OLEDs/hole blocker layer (HBL) 10 nm/electron transport layer (ETL) 30 nm/electron injection layer (EIL) composed of 1 nm ETM2/and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as SMB1: D1 (95:5%) mean here that the material SEB1 is present in the layer in a proportion by volume of 95% and D1 in a proportion of 5%. Analogously, the electron transport layer may also consist of a mixture of two materials. The exact structure of the OLEDs can be found in table 1. The materials used for production of the OLEDs are shown in table 4.

The OLEDs are characterized in a standard manner. For this purpose, the electroluminescence spectra, the current efficiency (measured in cd/A), the power efficiency (measured in lm/W) and the external quantum efficiency (EQE, measured in percent) are, as a function of luminance, calculated from current-voltage-luminance characteristics (IUL characteristics) assuming Lambertian radiation characteristics. The electroluminescence spectra are determined at a luminance of 1000 cd/m$^2$.

Use of compounds of the invention as materials in OLEDs: One use of the compounds of the invention is as dopant in the emission layer and as transport or blocker materials (HBL) in OLEDs. The compounds D-Ref.1 according to table 4 are used as a comparison according to the prior art. The results for the OLEDs are collated in table 2.

Table 1: Structure of the OLEDs

TABLE 1

Structure of the OLEDs

| Ex. | EML | HBL | ETL |
|---|---|---|---|
| Blue OLEDs (400-499 nm) | | | |
| D-Ref. 1 | SMB1:D-Ref. 1 (95%:5%) | ETM1 | ETM1:ETM2 (50%:50%) |
| D-D100 | SMB1:D100 (95%:5%) | ETM1 | ETM1:ETM2 (50%:50%) |
| D-D101 | SMB1:D101 (95%:5%) | ETM1 | ETM1:ETM2 (50%:50%) |
| D-D200 | SMB1:D200 (95%:5%) | ETM1 | ETM1:ETM2 (50%:50%) |
| D-D201 | SMB1:D201 (95%:5%) | ETM1 | ETM1:ETM2 (50%:50%) |
| D-D203 | SMB1:D203 (95%:5%) | ETM1 | ETM1:ETM2 (50%:50%) |
| D-D204 | SMB1:D204 (95%:5%) | ETM1 | ETM1:ETM2 (50%:50%) |
| D-D205 | SMB1:D205 (95%:5%) | ETM1 | ETM1:ETM2 (50%:50%) |
| D-D206 | SMB1:D206 (95%:5%) | ETM1 | ETM1:ETM2 (50%:50%) |
| D-D209 | SMB3:D209 (95%:5%) | ETM1 | ETM1:ETM2 (50%:50%) |
| D-D211 | SMB1:D211 (97%:3%) | ETM1 | ETM1:ETM2 (50%:50%) |
| D-D216 | SMB1:D216 (92%:8%) | ETM1 | ETM1:ETM2 (50%:50%) |
| Green OLEDs (500-549 nm) Yellow OLEDs (550-600 nm) | | | |
| D-D202 | SMB2:D202 (95%:5%) | ETM1 | ETM1:ETM2 (50%:50%) |
| D-D217 | SMB1:D217 (95%:5%) | ETM1 | ETM1:ETM2 (50%:50%) |

TABLE 2

Results for the vacuum-processed OLEDs

| Ex. | EQE (%) 1000 cd/m$^2$ | Voltage (V) 1000 cd/m$^2$ | Color |
|---|---|---|---|
| Blue OLEDs (430-499 nm) | | | |
| Ref. 1 | 6.0 | 4.7 | blue |
| D-D100 | 6.4 | 4.3 | blue |
| D-D101 | 6.0 | 4.3 | blue |
| D-D200 | 6.5 | 4.3 | blue |
| D-D201 | 6.4 | 4.2 | blue |
| D-D203 | 6.7 | 4.4 | blue |
| D-D204 | 6.5 | 4.4 | blue |
| D-D205 | 6.4 | 4.5 | blue |
| D-D206 | 6.8 | 4.3 | blue |
| D-D209 | 6.6 | 4.3 | blue |
| D-D211 | 6.5 | 4.2 | blue |
| D-D216 | 6.5 | 4.4 | blue |
| Green OLEDs (500-549 nm) Yellow OLEDs (550-600 nm) | | | |
| D-D217 | 6.7 | 3.6 | green |
| D-D202 | 6.8 | 3.4 | yellow |

2) Solution-Processed Components:

The production of solution-based OLEDs is fundamentally described in the literature, for example in WO 2004/037887 and WO 2010/097155. The examples that follow combined the two production processes (application from the gas phase and solution processing), such that layers up to and including emission layer were processed from solution and the subsequent layers (hole blocker layer/electron transport layer) were applied by vapor deposition under reduced pressure. For this purpose, the previously described general methods are matched to the circumstances described here (layer thickness variation, materials) and combined as follows.

The construction used is thus as follows:

substrate,
ITO (50 nm),
PEDOT (20 nm),
hole transport layer (HIL2) (20 nm),
emission layer (92% host H1, 8% dopant) (60 nm),
electron transport layer (ETM1 50%+ETM2 50%) (20 nm),
cathode (Al).

Substrates used are glass plates coated with structured ITO (indium tin oxide) of thickness 50 nm. For better processing, these are coated with the buffer (PEDOT) Clevios P VP AI 4083 (Heraeus Clevios GmbH, Leverkusen); PEDOT is at the top. Spin-coating is effected under air from water. The layer is subsequently baked at 180° C. for 10 minutes. The hole transport layer and the emission layer are applied to the glass plates thus coated. The hole transport layer is the polymer of the structure shown in table 4, which was synthesized according to WO 2010/097155. The polymer is dissolved in toluene, such that the solution typically has a solids content of about 5 g/l when, as is the case here, the layer thickness of 20 nm typical of a device is to be achieved by means of spin-coating. The layers are spun on in an inert gas atmosphere, argon in the present case, and baked at 180° C. for 60 min.

The emission layer is always composed of at least one matrix material (host material) and an emitting dopant (emitter). Details given in such a form as H1 (92%):D (8%) mean here that the material H1 is present in the emission layer in a proportion by weight of 92% and the dopant in a proportion by weight of 8%. The mixture for the emission layer is dissolved in toluene or chlorobenzene. The typical solids content of such solutions is about 18 g/l when, as here, the layer thickness of 60 nm which is typical of a device is to be achieved by means of spin-coating. The layers are spun on in an inert gas atmosphere, argon in the present case, and baked at 140 to 160° C. for 10 minutes. The materials used are shown in table 4.

The materials for the electron transport layer and for the cathode are applied by thermal vapor deposition in a vacuum chamber. The electron transport layer, for example, may consist of more than one material, the materials being added to one another by co-evaporation in a particular proportion by volume. Details given in such a form as ETM1:ETM2 (50%:50%) mean here that the ETM1 and ETM2 materials are present in the layer in a proportion by volume of 50% each. The materials used in the present case are shown in table 4.

TABLE 3

Results for the solution-processed OLEDs at 1000 cd/m$^2$

| Ex. | Dopant | EQE (%) | Voltage (V) | Color |
|---|---|---|---|---|
| Blue OLEDs (430-499 nm) | | | | |
| Ref.-Sol. | Ref.-D1 | 4.4 | 4.9 | blue |
| Sol.-D207 | D207 | 4.9 | 4.5 | blue |
| Sol.-D208 | D208 | 5.0 | 4.4 | blue |
| Sol.-D212 | D212 | 5.2 | 4.5 | blue |
| Sol.-D213 | D213 | 5.3 | 4.6 | blue |
| Sol.-D215 | D215 | 4.9 | 4.4 | blue |
| Green OLEDs (500-549 nm) Yellow OLEDs (550-600 nm) | | | | |
| Sol.-D210 | D210 | 6.7 | 4.0 | yellow |
| Sol. D219 | D219 | 6.3 | 4.2 | green |

TABLE 4

Structural formulae of the materials used

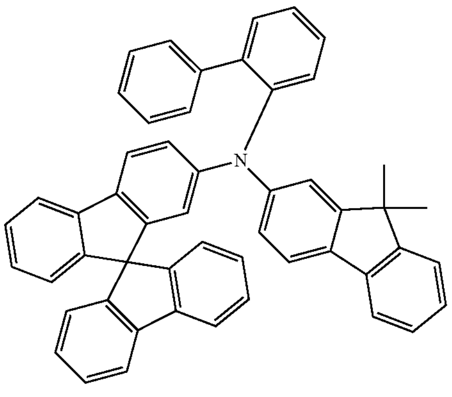

HTM1
[136463-07-5]

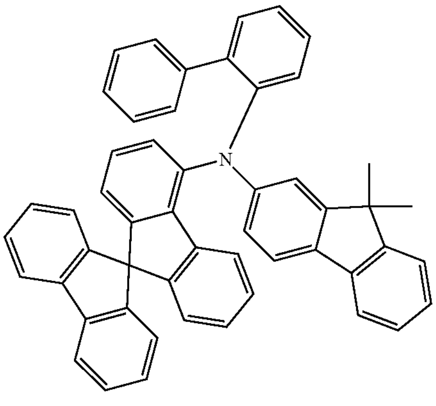

HTM2
[1450933-44-4]

TABLE 4-continued
| Structural formulae of the materials used |
| --- |
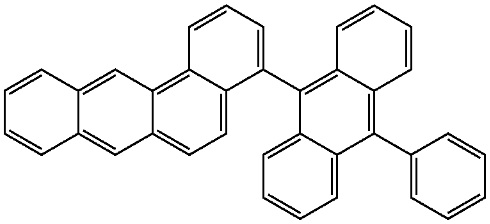
SMB1
[1087346-88-0]
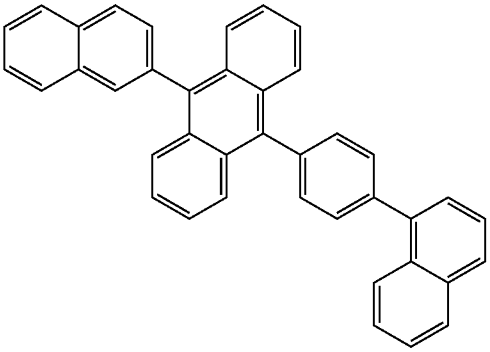
SMB2
[667940-34-3]
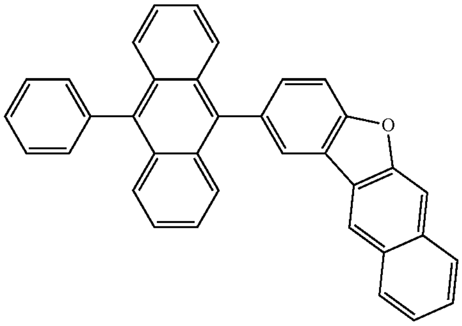
SMB3
[1627916-48-6]
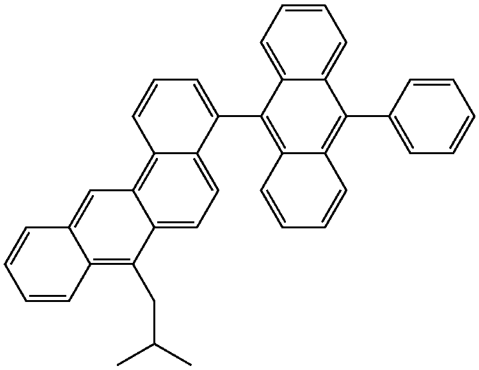
H1
[1818872-85-3]
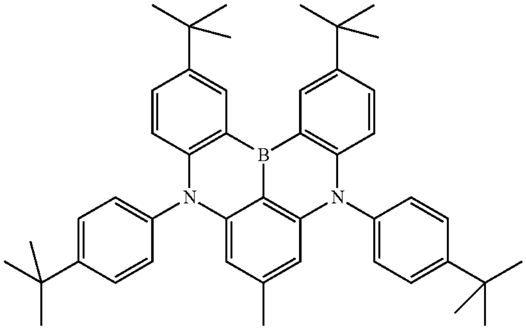
[1805802-42-9]
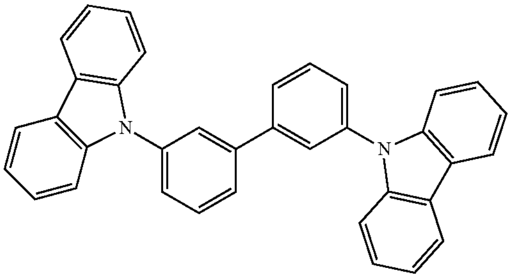
SMB4
[342638-54-4]

TABLE 4-continued

Structural formulae of the materials used

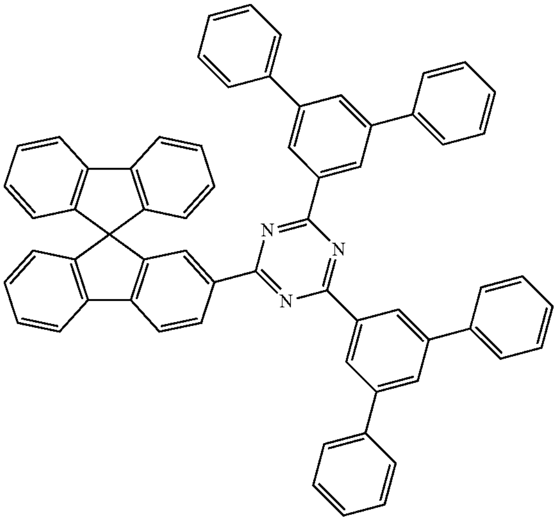

ETM1
[1233200-52-6]

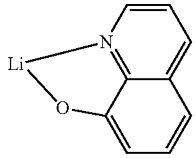

ETM2
[25387-93-3]

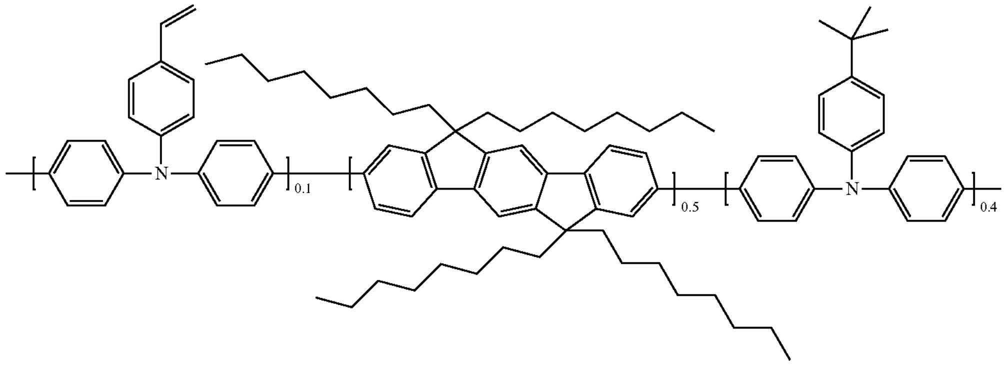

HIL2

The compounds of the invention show higher EQE values (External Quantum Efficiencies) at reduced operating voltages compared to the reference, which leads to a distinct improvement in power efficiencies of the device and hence to lower power consumption.

The invention claimed is:

1. A compound comprising at least one structure of the formula (I)

Formula (I)

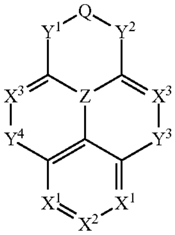

where the symbols and indices used are as follows:

Z is the same or different at each instance and is N or B;

Q is the same or different at each instance and is C═O, C(═O)—C(═O), $(R^d)_2C—C(R^d)_2$, $(R^d)C═C(R^d)$ or an aromatic or heteroaromatic ring system which has 5 to 60 aromatic ring atoms and binds to the $Y^1$ and $Y^2$ groups via two adjacent and mutually bonded carbon atoms and may be substituted in each case by one or more $R^d$ radicals;

$Y^1$, $Y^2$ is the same or different at each instance and is N(Ar), N(R), B(Ar), B(R), Al(Ar) or Al(R);

$Y^3$, $Y^4$ is the same or different at each instance and is N(Ar), N(R), P(Ar), P(R), P(═O)Ar, P(═O)R, P(═S)Ar, P(═S)R, B(Ar), B(R), Al(Ar), Al(R), Ga(Ar), Ga(R), C═O, $C(R)_2$, $Si(R)_2$, C═NR, C═NAr, C═C$(R)_2$, O, S, Se, S═O, or $SO_2$;

Ar is the same or different at each instance and is an aromatic or heteroaromatic ring system which has 5 to 60 aromatic ring atoms and may be substituted by one or more R radicals; the Ar group here may form a ring system with an Ar or R radical;

$X^1$ is the same or different at each instance and is N, $CR^a$, CAr, or C if a ring system is formed by a bond to an Ar or R radical, with the proviso that not more than two of the $X^1$, $X^2$ groups in one cycle are N;

$X^2$ is the same or different at each instance and is N, $CR^b$ or CAr, with the proviso that not more than two of the $X^1$, $X^2$ groups in one cycle are N;

$X^3$ is the same or different at each instance and is N, $CR^c$, CAr, or C if a ring system is formed by a bond to an Ar or R radical;

R, $R^a$, $R^b$, $R^c$, $R^d$ is the same or different at each instance and is H, D, OH, F, Cl, Br, I, CN, $NO_2$, $N(Ar')_2$, $N(R^1)_2$, C(=O)OAr', $C(=O)OR^1$, $C(=O)N(Ar')_2$, $C(=O)N(R^1)_2$, $C(Ar')_3$, $C(R^1)_3$, $Si(Ar')_3$, $Si(R^1)_3$, $B(Ar')_2$, $B(R^1)_2$, C(=O)Ar', $C(=O)R^1$, $P(=O)(Ar')_2$, $P(=O)(R^1)_2$, $P(Ar')_2$, $P(R^1)_2$, S(=O)Ar', $S(=O)R^1$, $S(=O)_2Ar'$, $S(=O)_2R^1$, $OSO_2Ar'$, $OSOR^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C{=}CR^1$, C≡C, $Si(R^1)_2$, C=O, C=S, C=Se, $C{=}NR^1$, —C(=O)O—, $—C(=O)NR^1—$, $NR^1$, $P(=O)(R^1)$, —O—, —Se—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R, $R^a$, $R^b$, $R^c$, $R^d$ radicals may also form a ring system together;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge wherein said bridge is selected from the group consisting of a single bond, $B(R^1)$, $C(R^1)_2$, $Si(R^1)_2$, C=O, $C{=}NR^1$, $C{=}C(R^1)_2$, O, S, S=O, $SO_2$, $N(R^1)$, $P(R^1)$ and $P(=O)R^1$;

$R^1$ is the same or different at each instance and is H, D, F, Cl, Br, I, CN, $NO_2$, $N(Ar'')_2$, $N(R^2)_2$, C(=O)OAr'', $C(=O)OR_2$, C(=O)Ar'', $C(=O)R^2$, $P(=O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $—R^2C{=}CR^2—$, —C≡C—, $Si(R^2)_2$, C=O, C=S, C=Se, $C{=}NR^2$, —C(=O)O—, $—C(=O)NR^2—$, $NR^2$, $P(=O)(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals; at the same time, two or more $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C=O, $C{=}NR^2$, $C{=}C(R^2)_2$, O, S, S=O, $SO_2$, $N(R^2)$, $P(R^2)$ and $P(=O)R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more substituents $R^2$ together may form a ring system.

2. The compound as claimed in claim 1, comprising at least one structure of the formula (II)

Formula (II)

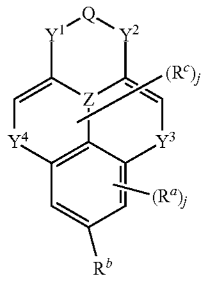

where $Y^1$, $Y^2$, $Y^3$, $Y^4$, Z, Q, $R^a$, $R^b$ and $R^c$ have the definitions given in claim 1 and the index j is 0, 1 or 2.

3. The compound of claim 1, comprising at least one structure of the formulae (IIIa) to (IIIk):

Formula (IIIa)

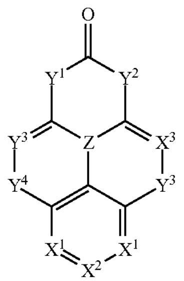

-continued
Formula (IIIb)
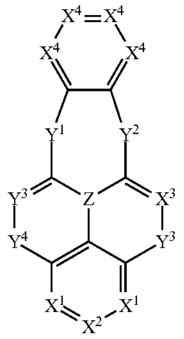
Formula (IIIc)
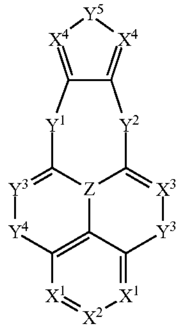
Formula (IIId)
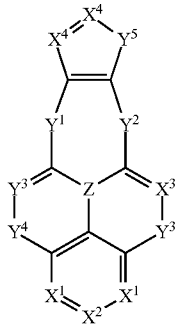
Formula (IIIe)
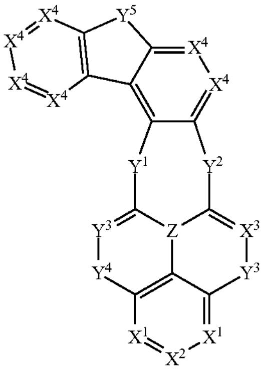
-continued
Formula (IIIf)
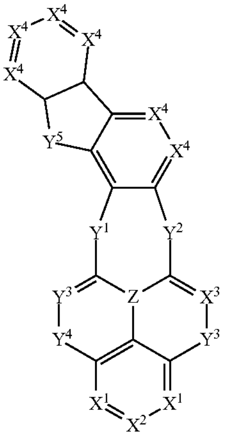
Formula (IIIg)
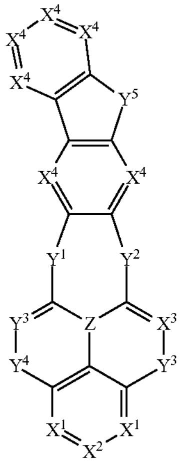
Formula (IIIh)
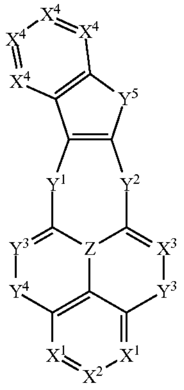
Formula (IIIi)
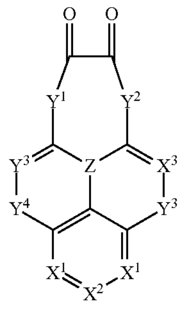

-continued

Formula (IIIj)

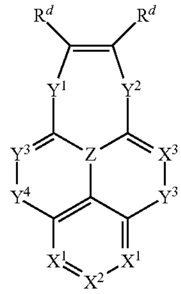

Formula (IIIk)

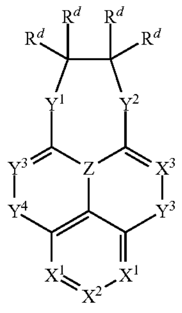

where $Y^1$, $Y^2$, $Y^3$, $Y^4$, $X^1$, $X^2$, $X^3$, $R^d$ and Z have the definitions given in claim 1, $X^4$ is the same or different at each instance and is N, $CR^d$, or C if a ring system is formed by a bond to an Ar or R radical, and $Y^5$ is $C(R)_2$, NR, NAr', BR, BAr', O or S, where R and Ar' have the definitions given in claim 1.

4. The compound as claimed in claim 1, comprising at least one structure of the formula (IVa) to (IVn):

Formula (IVa)

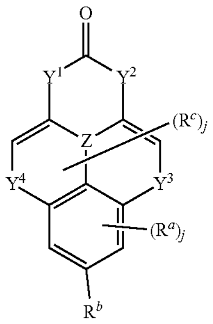

Formula (IVb)

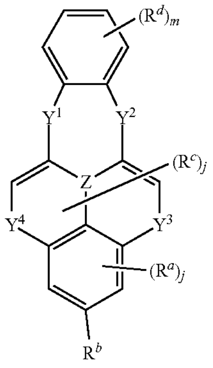

-continued

Formula (IVc)

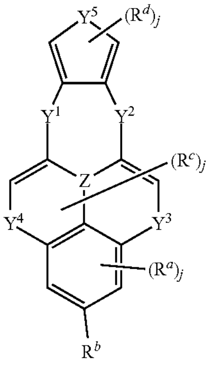

Formula (IVd)

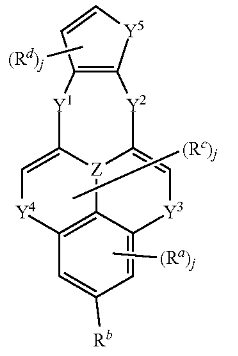

Formula (IVe)

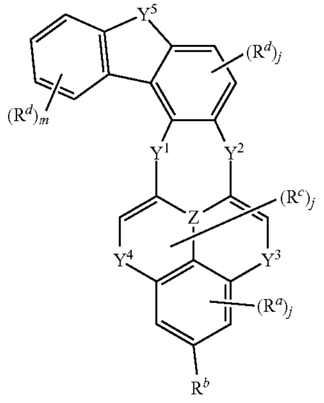

Formula (IVf)

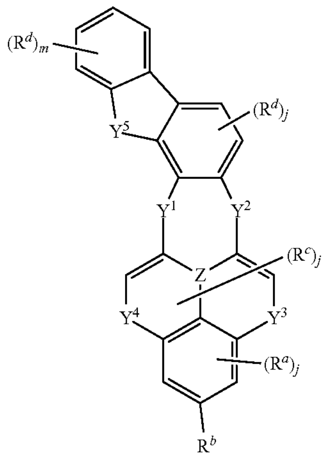

-continued
Formula (IVg)
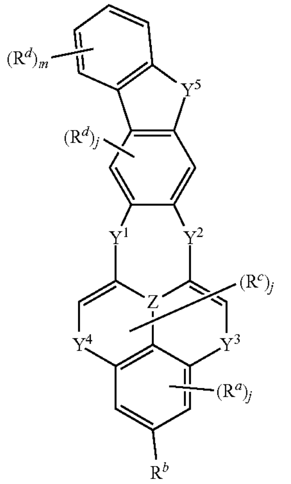
Formula (IVh)
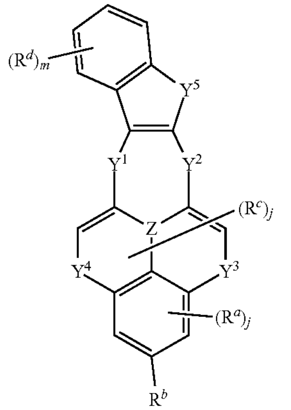
Formula (IVi)
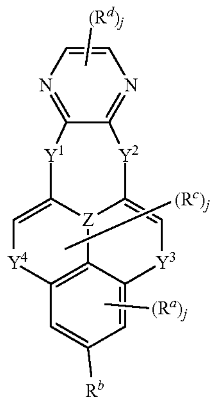
-continued
Formula (IVj)
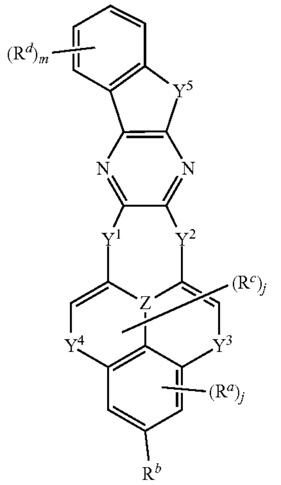
Formula (IVk)
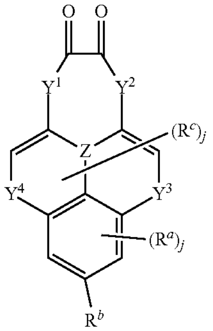
Formula (IVm)
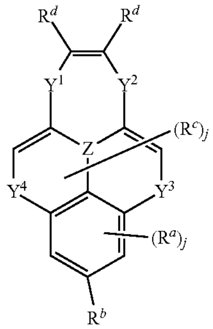
Formula (IVn)
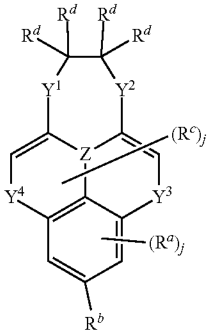
where $Y^1$, $Y^2$, $Y^3$, $Y^4$, Z, $R^a$, $R^b$, $R^c$ and $R^d$ have the definitions given in claim 1, the index j is 0, 1 or 2, the index m is 0, 1, 2, 3 or 4, and $Y^5$ is $C(R)_2$, NR, NAr', BR, BAr', O or S, where R and Ar' have the definitions given in claim 1.

5. The compound as claimed in claim 1, wherein Z is N and at least one of the $Y^1$, $Y^2$ groups is B(Ar), B(R), Al(Ar), or Al(R).

6. The compound as claimed in claim 1, wherein Z is N and at least one of the $Y^1$, $Y^2$ groups is N(Ar) or N(R).

7. The compound as claimed in claim 1, wherein at least one of the $Y^1$, $Y^2$ groups represent(s) N(Ar) or N(R) and at least one of the $Y^3$, $Y^4$ groups is B(Ar), B(R), Al(Ar), Al(R), Ga(Ar), Ga(R), P(=O)Ar, P(=O)R, C=O, S=O or $SO_2$.

8. The compound as claimed in claim 1, wherein Z is B and at least one of the $Y^1$, $Y^2$ groups is N(Ar) or N(R).

9. The compound as claimed in claim 1, wherein Z is B and at least one of the $Y^1$, $Y^2$ groups is B(Ar), B(R), Al(Ar), or Al(R).

10. The compound as claimed in claim 1, wherein at least one of the $Y^1$, $Y^2$ groups represents B(Ar), B(R), Al(Ar) or Al(R) and at least one of the $Y^3$, $Y^4$ groups is N(Ar), N(R), P(Ar), P(R), O, S or Se.

11. The compound as claimed in claim 1, comprising at least one structure of the formulae (Va) to (Vk):

Formula (Va)

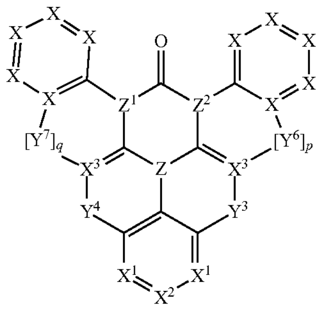

Formula (Vb)

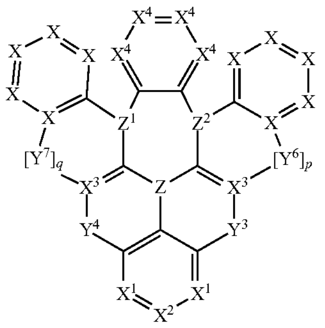

Formula (Vc)

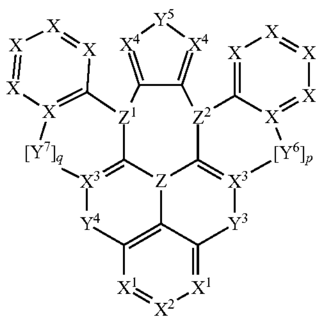

-continued

Formula (Vd)

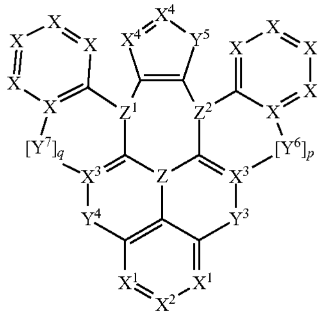

Formula (Ve)

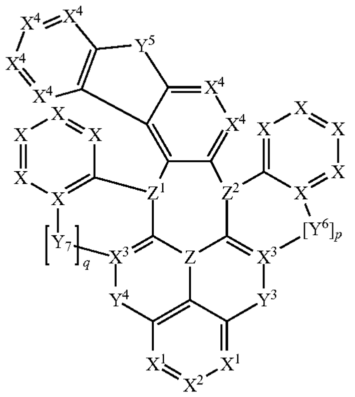

Formula (Vf)

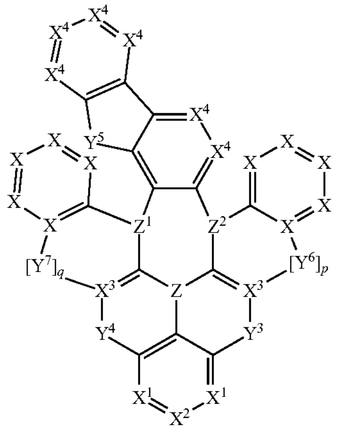

Formula (Vg)

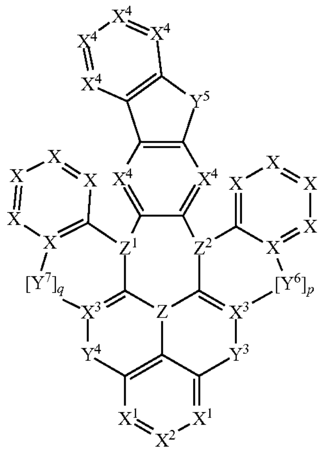

-continued

Formula (Vh)

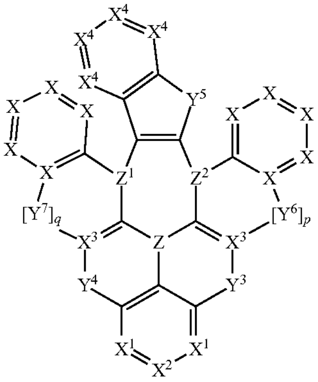

Formula (Vi)

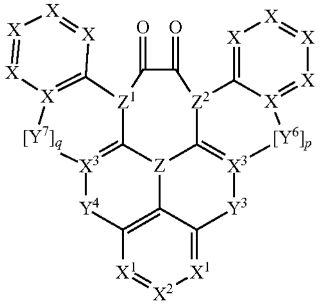

Formula (Vj)

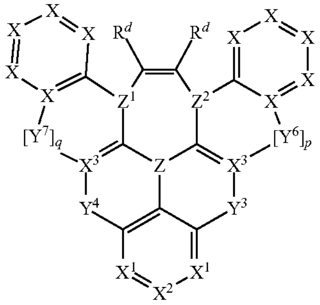

Formula (Vk)

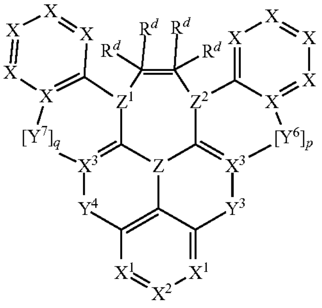

where $Y^3$, $Y^4$, $X^1$, $X^2$, $X^3$ and Z have the definitions given in claim 1, $X^4$ is the same or different at each instance and is N, $CR^d$, or C if a ring system is formed by a bond to an Ar or R radical, $Y^5$ is $C(R)_2$, NR, NAr', BR, BAr', O or S, where R and Ar' have the definitions given in claim 1:

$Z^1$, $Z^2$ is the same or different at each instance and is N, B or Al;

X is the same or different at each instance and is N, CR, or C if a ring system is formed by a bond to an $X^3$ radical, with the proviso that not more than two of the X groups in one cycle are N, where R is as defined in claim 1;

$Y^6$, $Y^7$ is the same or different at each instance and is a bond, N(Ar'), N(R), P(Ar'), P(R), P(=O)Ar', P(=O)R, P(=S)Ar', P(=S)R, B(Ar'), B(R), Al(Ar'), Al(R), Ga(Ar'), Ga(R), C=O, $C(R)_2$, $Si(R)_2$, C=NR, C=NAr', $C{=}C(R)_2$, O, S, Se, S=O, or $SO_2$, where R and Ar' have the definitions given in claim 1;

p, q is the same or different at each instance and is 0 or 1, where 0 means that the corresponding group is absent.

12. The compound as claimed in claim 1, comprising at least one structure of the formulae (VI-1) to (VI-39):

Formula (VI-1)

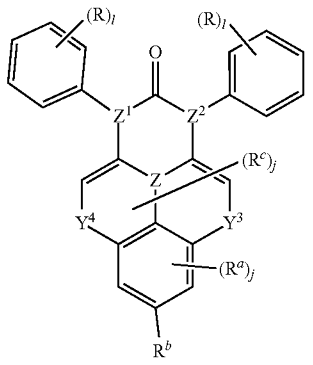

Formula (VI-2)

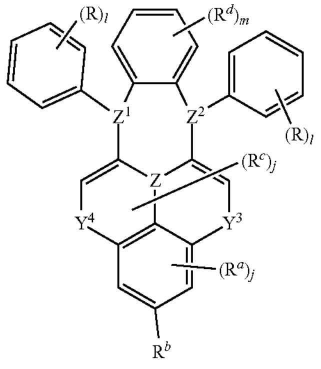

Formula (VI-3)

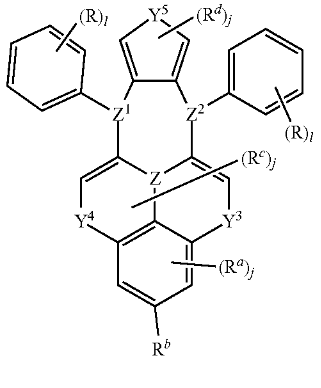

-continued
Formula (VI-4)
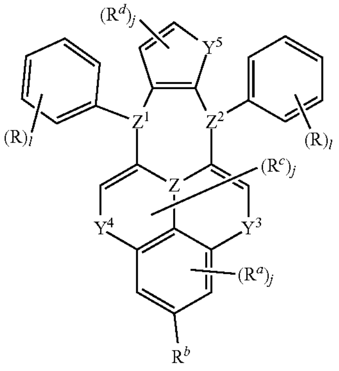
Formula (VI-5)
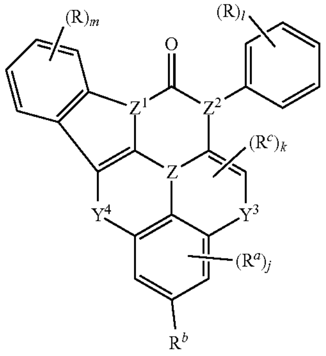
Formula (VI-6)
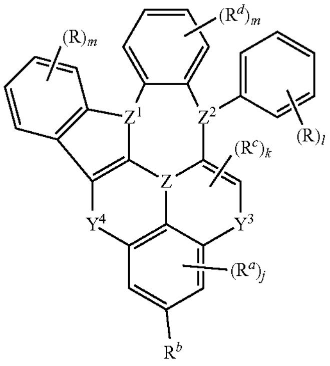
Formula (VI-7)
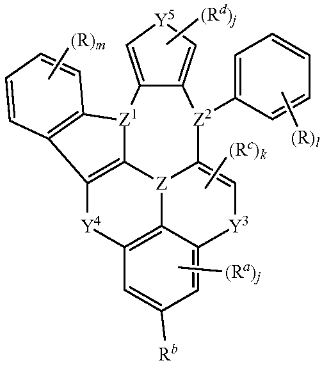
-continued
Formula (VI-8)
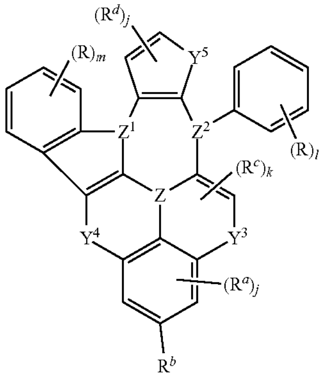
Formula (VI-9)
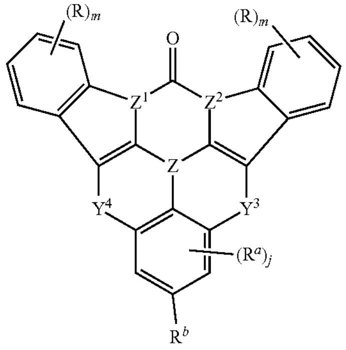
Formula (VI-10)
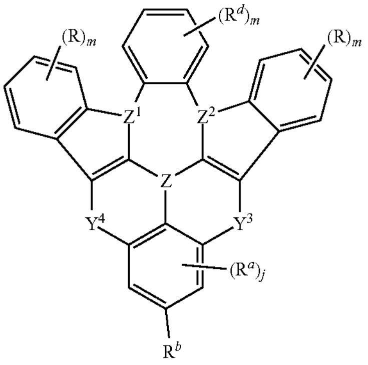
Formula (VI-11)
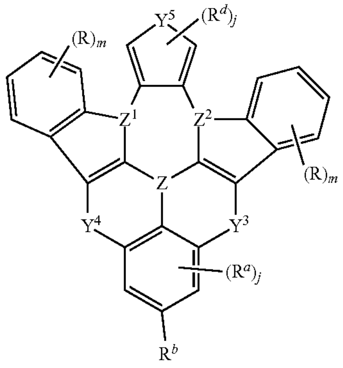

-continued
Formula (VI-12)
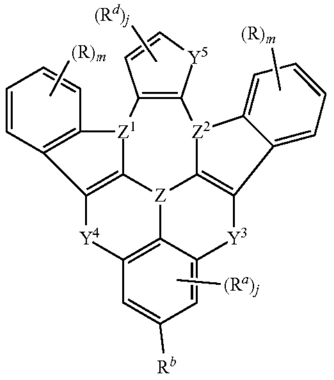
Formula (VI-13)
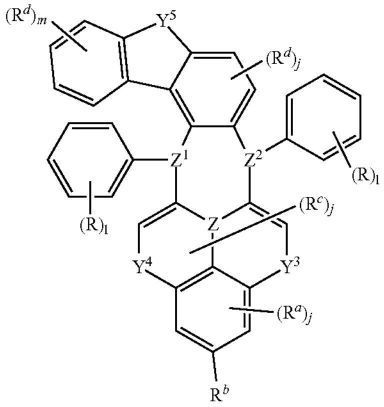
Formula (VI-14)
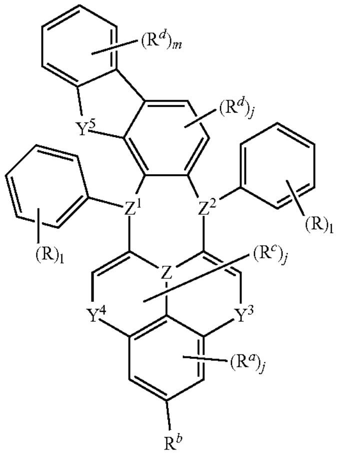
-continued
Formula (VI-15)
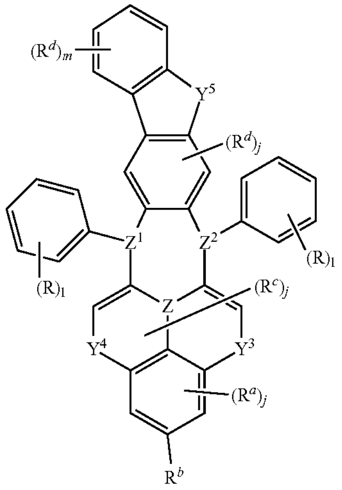
Formula (VI-16)
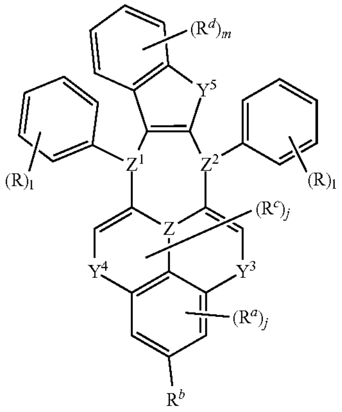
Formula (VI-17)
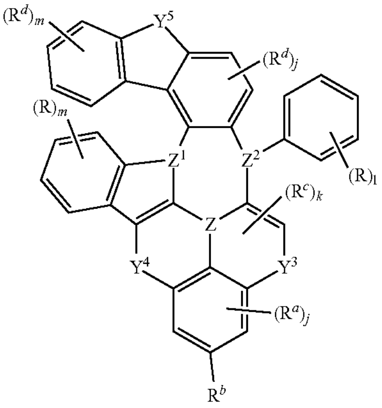

-continued
Formula (VI-18)
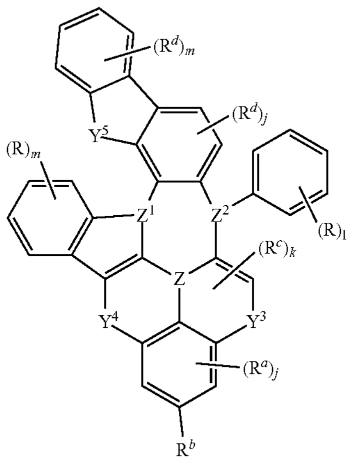
Formula (VI-19)
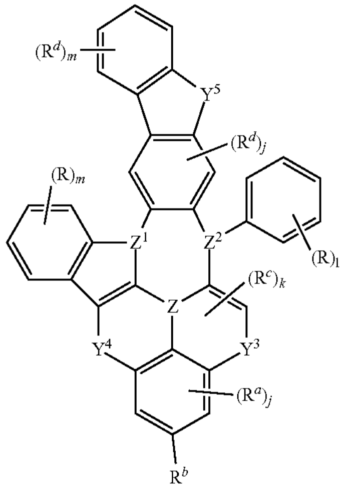
Formula (VI-20)
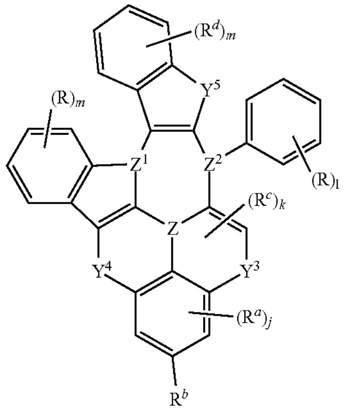
-continued
Formula (VI-21)
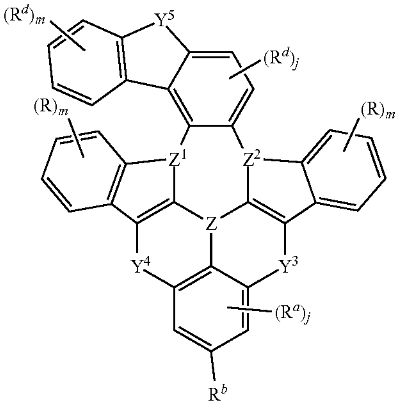
Formula (VI-22)
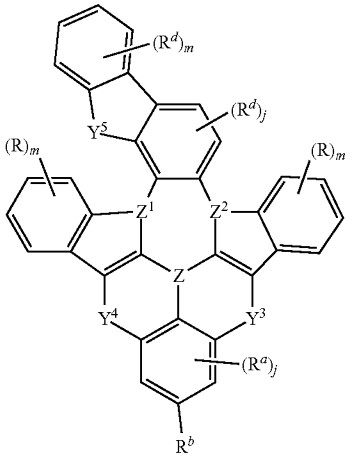
Formula (VI-23)
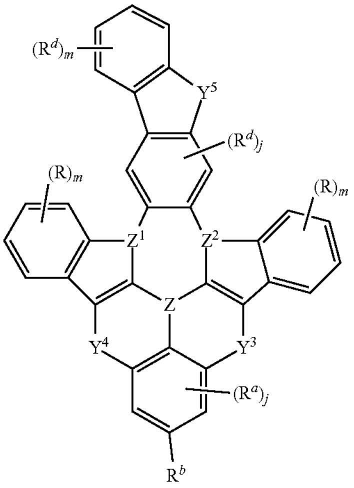

-continued
Formula (VI-24)
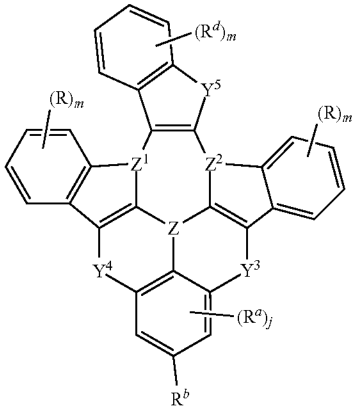
Formula (VI-25)
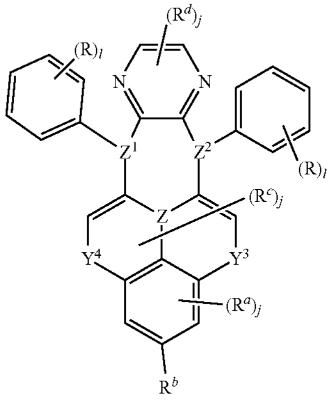
Formula (VI-26)
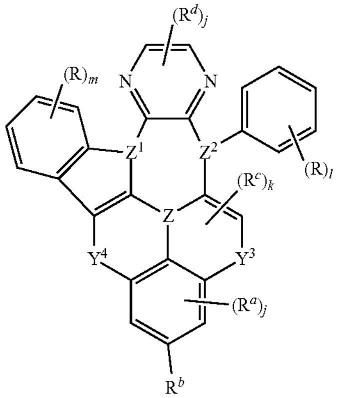
Formula (VI-27)
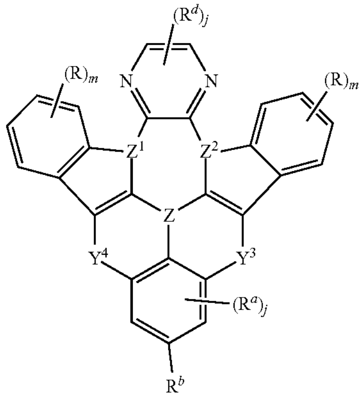
-continued
Formula (VI-28)
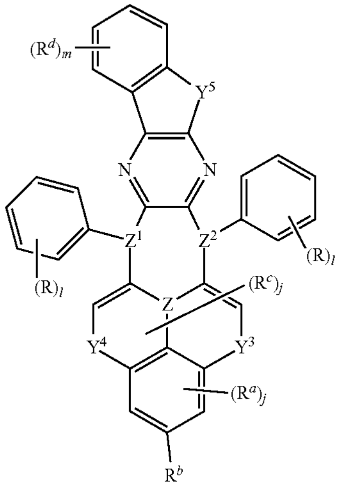
Formula (VI-29)
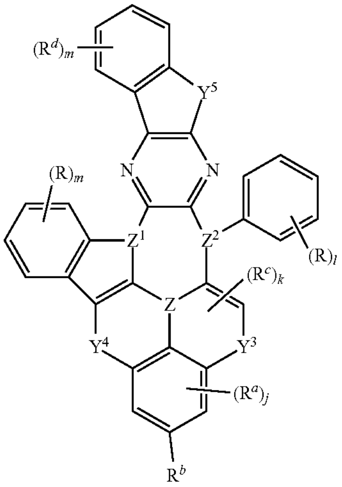
Formula (VI-30)
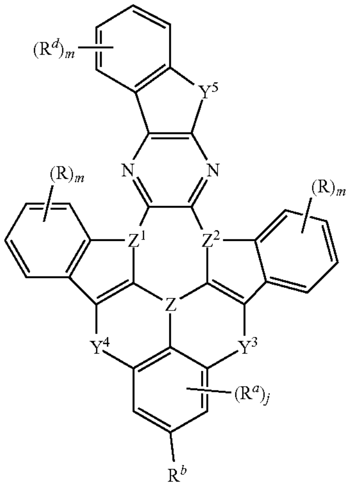

-continued
Formula (VI-31)
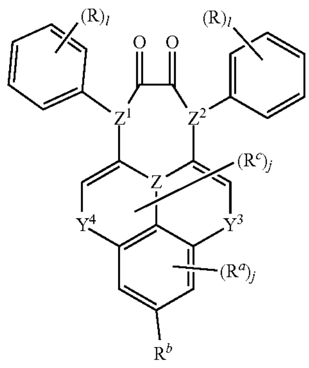
Formula (VI-32)
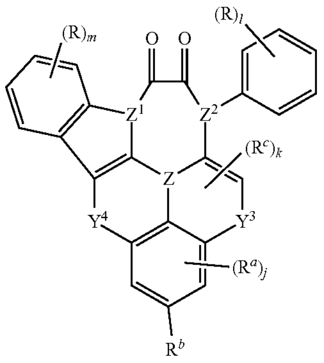
Formula (VI-33)
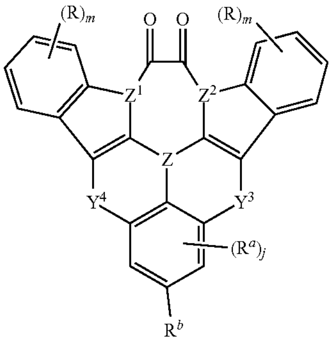
Formula (VI-34)
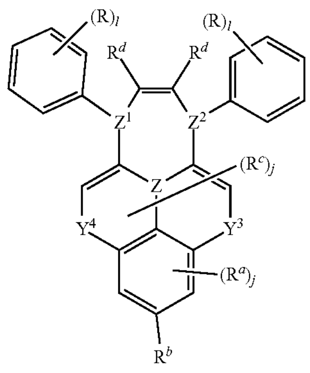
-continued
Formula (VI-35)
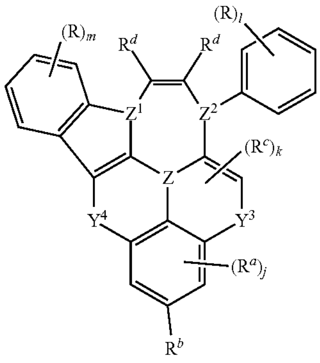
Formula (VI-36)
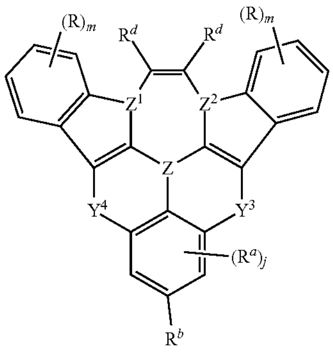
Formula (VI-37)
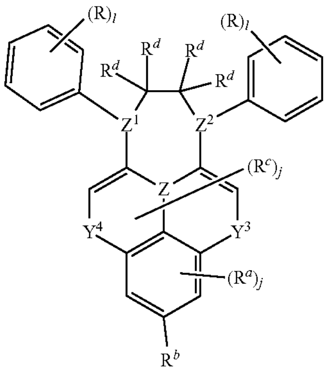
Formula (VI-38)
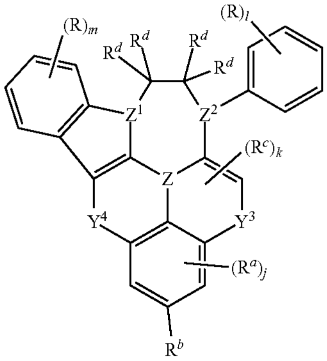

-continued

Formula (VI-39)

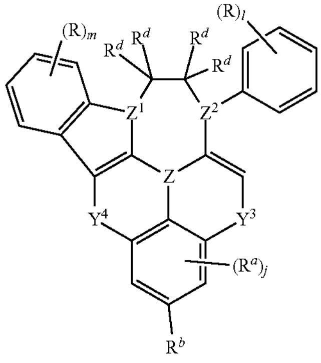

where $Y^3$, $Y^4$, Z, R, $R^a$, $R^b$, $R^c$ and $R^d$ have the definitions given in claim 1, and the further symbols have the following definition:

$Z^1$, $Z^2$ is the same or different at each instance and is N, B or Al;

l is 0, 1, 2, 3, 4 or 5;

m is 0, 1, 2, 3 or 4;

j is 0, 1 or 2;

k is 0 or 1; and $Y^5$ is $C(R)_2$, NR, NAr', BR, BAr', O or S, where R and Ar' have the definitions given in claim 1.

13. The compound as claimed in claim 1, comprising at least one structure of the formulae (VII-1) to (VII-18):

Formula (VII-1)

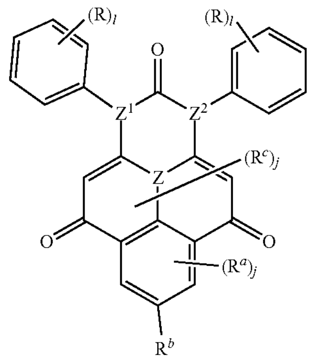

Formula (VII-2)

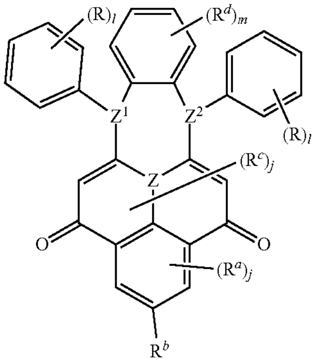

-continued

Formula (VII-3)

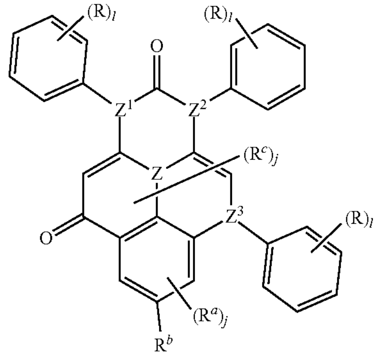

Formula (VII-4)

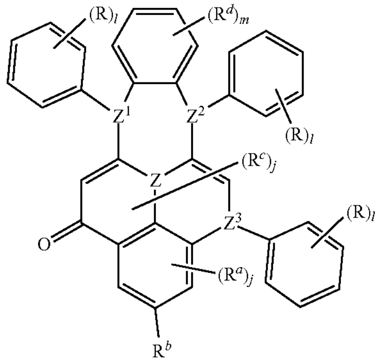

Formula (VII-5)

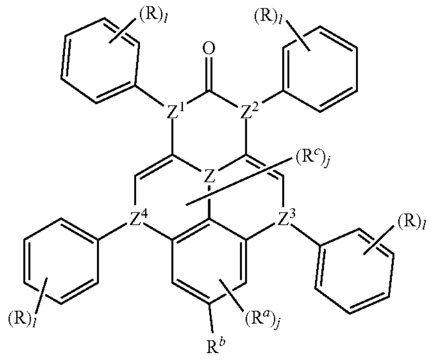

Formula (VII-6)

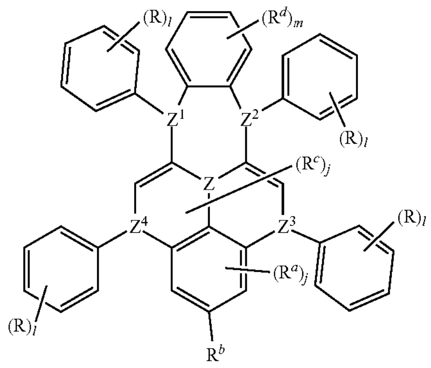

-continued
Formula (VII-7)
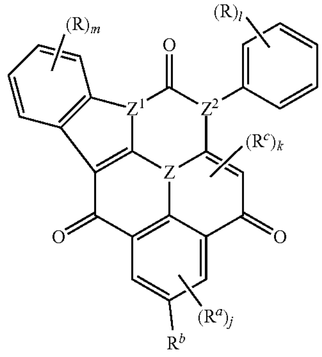
Formula (VII-8)
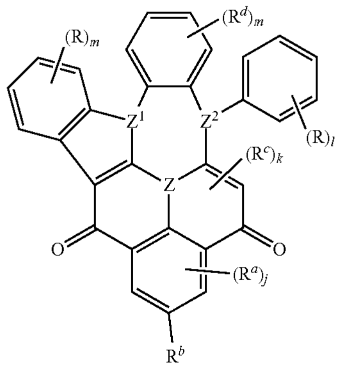
Formula (VII-9)
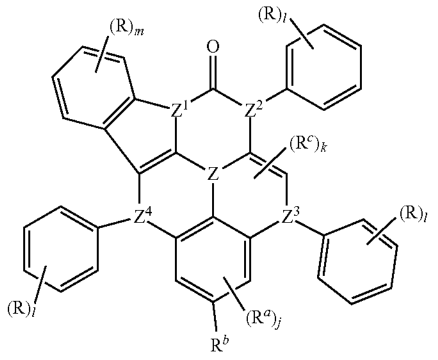
Formula (VII-10)
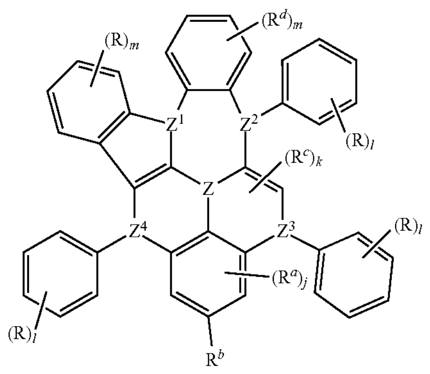
-continued
Formula (VII-11)
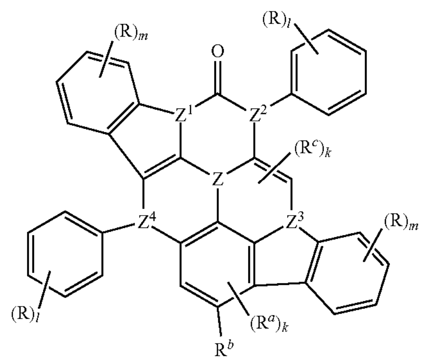
Formula (VII-12)
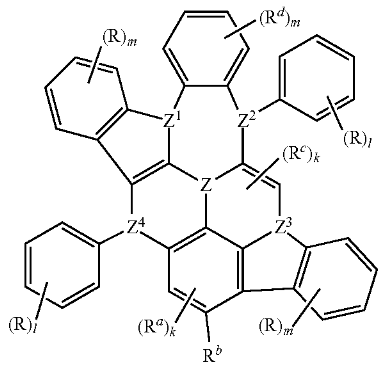
Formula (VII-13)
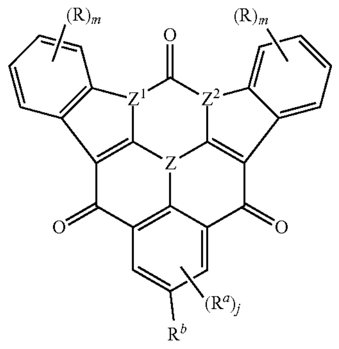
Formula (VII-14)
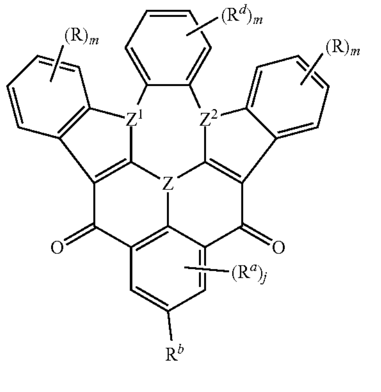

-continued

Formula (VII-15)

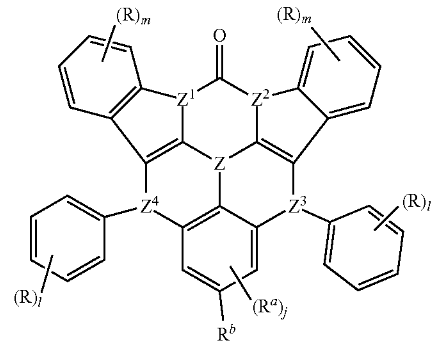

Formula (VII-16)

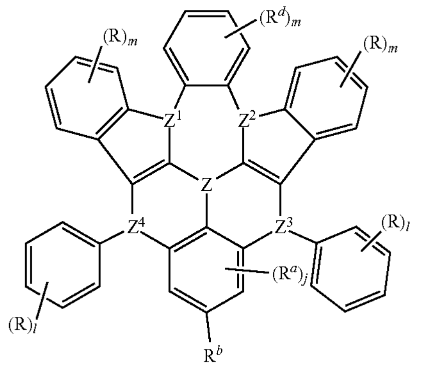

Formula (VII-17)

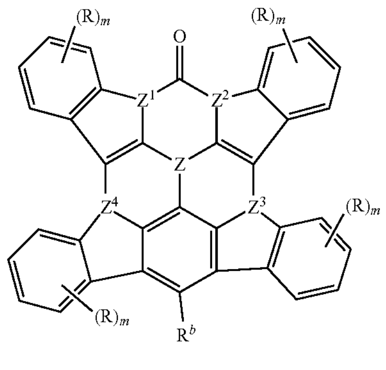

Formula (VII-18)

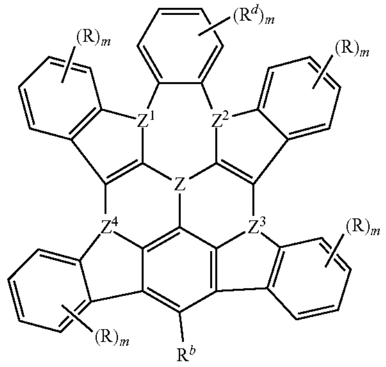

where Z, R, $R^a$, $R^b$, $R^c$ and $R^d$ have the definitions given in claim 1, and the further symbols have the following definition:

$Z^1$, $Z^2$, $Z^3$, $Z^4$ is the same or different at each instance and is N, B or Al;

l is 0, 1, 2, 3, 4 or 5;

m is 0, 1, 2, 3 or 4;

j is 0, 1 or 2;

k is 0 or 1.

14. The compound as claimed in claim 1, wherein at least two R, $R^a$, $R^b$, $R^c$, $R^d$ radicals to which the two R, $R^a$, $R^b$, $R^c$, $R^d$ radicals bind form a fused ring, where the two R, $R^a$, $R^b$, $R^c$, $R^d$ radicals form at least one structure of the formulae (RA-1) to (RA-12):

Formula RA-1

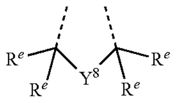

Formula RA-2

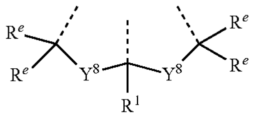

Formula RA-3

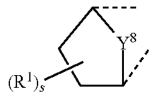

Formula RA-4

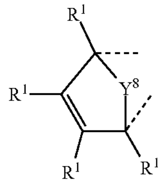

Formula RA-5

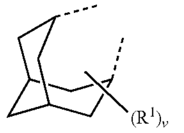

Formula RA-6

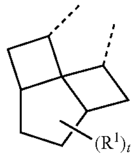

Formula RA-7

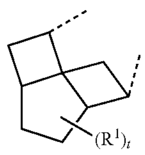

Formula RA-8

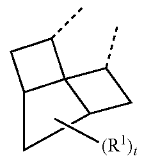

Formula RA-9

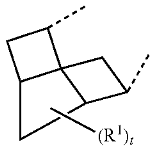

-continued

Formula RA-10

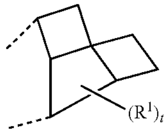

Formula RA-11

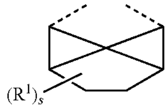

Formula RA-12

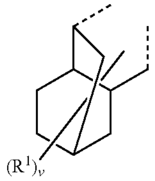

where $R^1$ has the definition set out above, the dotted bonds represent the sites of attachment via which the two R, $R^a$, $R^b$, $R^c$, $R^d$ radicals bind, and the further symbols have the following definition:

$Y^8$ is the same or different at each instance and is $C(R^1)_2$, $(R^1)_2C—C(R^1)_2$, $(R^1)C{=}C(R^1)$, $NR^1$, NAr', O or S;

$R^e$ is the same or different at each instance and is F, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^2$ radicals, where one or more nonadjacent $CH_2$ groups may be replaced by $R^2C{=}CR^2$, C≡C, $Si(R^2)_2$, C═O, C═S, C═Se, $C{=}NR^2$, —C(═O)O—, $—C(=O)NR^2—$, $NR^2$, $P(=O)(R^1)$, —O—, —S—, SO or $SO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals; at the same time, two $R^e$ radicals, or one $R^e$ radical with an $R^1$ radical, may also form a ring system, where $R^1$ and $R^2$ have the definitions given in claim 1;

s is 0, 1, 2, 3, 4, 5 or 6;

t is 0, 1, 2, 3, 4, 5, 6, 7 or 8;

v is 0, 1, 2, 3, 4, 5, 6, 7, 8 or 9.

15. An oligomer, polymer or dendrimer containing one or more compounds as claimed in claim 1, wherein, in place of a hydrogen atom or a substituent, there are one or more bonds of the compounds to the polymer, oligomer or dendrimer.

16. A formulation comprising at least one compound as claimed in claim 1 and at least one further compound.

17. A composition comprising at least one compound as claimed in claim 1 and at least one further compound selected from the group consisting of fluorescent emitters, phosphorescent emitters, emitters that exhibit TADF, host materials, electron transport materials, electron injection materials, hole conductor materials, hole injection materials, electron blocker materials and hole blocker materials.

18. A process for preparing a compound as claimed in claim 1, comprising synthesizing a base skeleton having a Z group or a precursor of the Z group, and introducing at least one of the $Y^1$, $Y^2$, $Y^3$, $Y^4$ groups by means of a nucleophilic aromatic substitution reaction or a coupling reaction.

19. A method comprising providing at least one compound as claimed in claim 1 and including the compound in an electronic device.

20. An electronic device comprising at least one compound as claimed in claim 1.

* * * * *